(12) United States Patent
Kim et al.

(10) Patent No.: US 9,831,438 B2
(45) Date of Patent: Nov. 28, 2017

(54) COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Se-Hun Kim, Yongin (KR); Seong-Jin Jeong, Seoul (KR); Jong-In Hong, Seoul (KR); Mi-Kyung Kim, Yongin (KR); Chang-Woong Chu, Yongin (KR)

(73) Assignees: SAMSUNG DISPLAY CO., LTD., Yongin, Gyeonggi-Do (KR); SEOUL NATIONAL UNIVERSITY INDUSTRY-UNIVERSITY R & DB FOUNDATION, Seoul (KR)

( * ) Notice: Subject to any disclaimer, the term of this patent is extended or adjusted under 35 U.S.C. 154(b) by 275 days.

(21) Appl. No.: 14/564,248

(22) Filed: Dec. 9, 2014

(65) Prior Publication Data

US 2016/0020400 A1 Jan. 21, 2016

(30) Foreign Application Priority Data

Jul. 16, 2014 (KR) .................. 10-2014-0089799

(51) Int. Cl.
| | |
|---|---|
| H01L 51/00 | (2006.01) |
| H01L 27/32 | (2006.01) |
| H01L 51/50 | (2006.01) |
| C07C 255/50 | (2006.01) |
| C07D 215/06 | (2006.01) |

(Continued)

(52) U.S. Cl.
CPC ........ *H01L 51/0054* (2013.01); *C07C 255/50* (2013.01); *C07D 209/08* (2013.01);
(Continued)

(58) Field of Classification Search
None
See application file for complete search history.

(56) References Cited

U.S. PATENT DOCUMENTS

| | | | |
|---|---|---|---|
| 5,635,308 A | 6/1997 | Inoue et al. | |
| 2004/0076853 A1* | 4/2004 | Jarikov | C09K 11/06 428/690 |

(Continued)

FOREIGN PATENT DOCUMENTS

| | | |
|---|---|---|
| JP | 07-138561 A | 5/1995 |
| JP | 08-12600 A | 1/1996 |

(Continued)

OTHER PUBLICATIONS

Tang et al., Organic Electroluminescent Diodes, Applied Physics Letters, Sep. 21, 1987, pp. 913-915, vol. No. 51, AIP Publishing LLC., New York.

(Continued)

*Primary Examiner* — J. L. Yang
(74) *Attorney, Agent, or Firm* — Lee & Morse, P.C.

(57) ABSTRACT

A compound, an organic light-emitting device, and a flat display apparatus, the compound being represented by Formula 1, below:

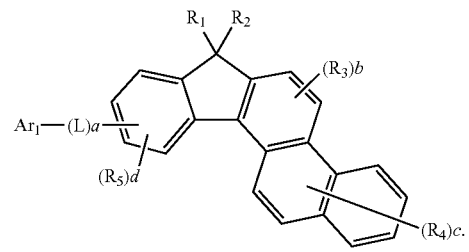

21 Claims, 1 Drawing Sheet

(51) Int. Cl.
  *C07D 219/14* (2006.01)
  *C07D 209/08* (2006.01)
  *C07D 209/56* (2006.01)
  *C07D 209/86* (2006.01)
(52) U.S. Cl.
  CPC ......... *C07D 209/56* (2013.01); *C07D 209/86* (2013.01); *C07D 215/06* (2013.01); *C07D 219/14* (2013.01); *H01L 51/0052* (2013.01); *H01L 51/0058* (2013.01); *H01L 51/0059* (2013.01); *H01L 51/5012* (2013.01)

(56) References Cited

U.S. PATENT DOCUMENTS

2007/0231503 A1* 10/2007 Hwang .................. C09K 11/06 428/1.1
2008/0160347 A1 7/2008 Wang et al.
2014/0374717 A1* 12/2014 Kim ....................... C07C 255/58 257/40

FOREIGN PATENT DOCUMENTS

| | | |
|---|---|---|
| JP | 08-239655 A | 9/1996 |
| JP | 2658463 B2 | 6/1997 |
| JP | 2011-37838 A | 2/2011 |
| KR | 10-2008-0031808 A | 4/2008 |
| KR | 10-2011-0070258 A | 6/2011 |
| KR | 10-2012-0117676 A | 10/2012 |

OTHER PUBLICATIONS 192-87-0 9H-indeno[2,1-c]phenanthrene, p. 1, ChemNet.com.

* cited by examiner

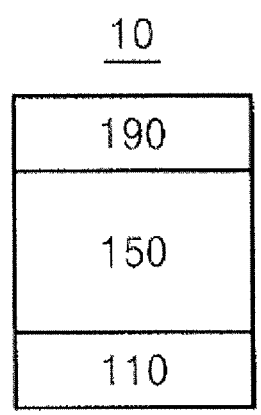

COMPOUND AND ORGANIC LIGHT-EMITTING DEVICE INCLUDING THE SAME

CROSS-REFERENCE TO RELATED APPLICATION

Korean Patent Application No. 10-2014-0089799, filed on Jul. 16, 2014, in the Korean Intellectual Property Office, and entitled: "Compound and Organic Light-Emitting Device Including The Same," is incorporated by reference herein in its entirety.

BACKGROUND

1. Field

Embodiments relate to a compound and an organic light-emitting device including the compound.

2. Description of the Related Art

Organic light-emitting devices (OLEDs), which are self-emitting devices, may have advantages such as wide viewing angles, excellent contrast, quick response, high brightness, excellent driving voltage characteristics, and may provide multicolored images.

An organic light-emitting device may have a structure of a first electrode, a hole transport region, an emission, an electron transport region, and a second electrode that are sequentially stacked on a substrate. Holes injected from the first electrode may move to the emission layer via the hole transport region, and electrons injected from the second electrode may move to the emission layer via the electron transport region. Carriers, such as the holes and electrons, may recombine in the emission layer to generate excitons. When the exitons drop from an excited state to a ground state, light may be emitted.

SUMMARY

Embodiments are directed to a compound and an organic light-emitting device including the compound.

Additional aspects will be set forth in part in the description which follows and, in part, will be apparent from the description, or may be learned by practice of the presented embodiments.

According to one or more embodiments, an organic light-emitting device includes a compound represented by Formula 1 below:

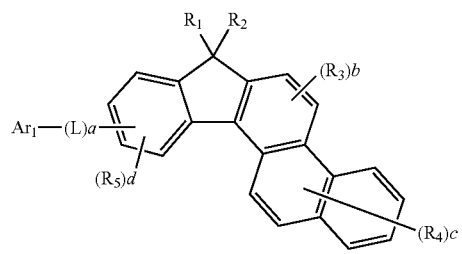

<Formula 1> wherein, in Formula 1,

L is selected from a single bond, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

$R_1$ to $R_5$ and $Ar_1$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

a, b, c, and d are each independently an integer selected from 0 to 6;

at least one substituent selected from the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group is selected from, a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, $C_1$-$C_{60}$ alkyl group, $C_2$-$C_{60}$ alkenyl group, $C_2$-$C_{60}$ alkynyl group, $C_1$-$C_{60}$ alkoxy group, $C_3$-$C_{10}$ cycloalkyl group, $C_2$-$C_{10}$ heterocycloalkyl group, $C_3$-$C_{10}$ cycloalkenyl group, $C_2$-$C_{10}$ heterocycloalkenyl group, $C_6$-$C_{60}$ aryl group, $C_6$-$C_{60}$ aryloxy group, $C_6$-$C_{60}$ arylthio group, $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

According to one or more embodiments, an organic light-emitting device includes a first electrode; a second electrode facing the first electrode; and an organic layer that is disposed between the first electrode and the second electrode and includes an emission layer, wherein the organic layer includes the compound.

According to one or more embodiments, a flat display apparatus includes the organic light-emitting device, wherein a first electrode of the organic light-emitting device is electrically connected with a source electrode or a drain electrode of a thin film transistor.

BRIEF DESCRIPTION OF THE DRAWING

Features will be apparent to those of skill in the art by describing in detail exemplary embodiments with reference to the attached drawing in which:

The FIGURE illustrates a schematic view of a structure of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an embodiment, a compound may be represented by Formula 1 below:

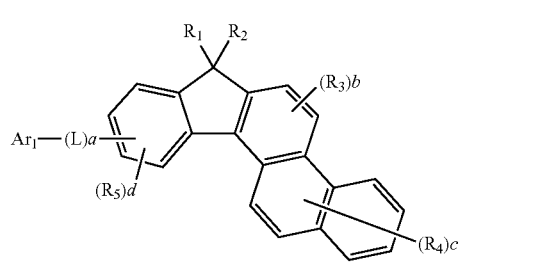

<Formula 1>

In Formula 1,

L may be selected from a single bond, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

$R_1$ to $R_5$ and $Ar_1$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_{3-10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

a, b, c, and d may be each independently an integer selected from 0 to 6. In an implementation, when L is a single bond, a is 1, or when a is 0, a single bond may connect Ar1 to a carbon atom of the fluorene moiety of Formula 1.

At least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

Hereinafter, the substituents of Formula 1 will be described in detail.

According to one embodiment, in Formula 1, $R_1$ and $R_2$ may be each independently selected from a substituted or unsubstituted $C_1$-$C_{60}$ alkyl group and a substituted or unsubstituted $C_6$-$C_{60}$ aryl group.

According to another embodiment, in Formula 1, $R_1$ and $R_2$ may be each independently a methyl group or a phenyl group.

According to another embodiment, in Formula 1, $R_3$ to $R_5$ may be each independently a hydrogen or a deuterium.

According to another embodiment, in Formula 1, $Ar_1$ may be selected from a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group.

According to another embodiment, in Formula 1, $Ar_1$ may be a group represented by one of the following Formulae 7a to 7f:

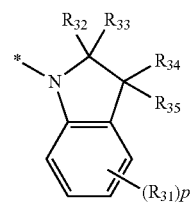

7a

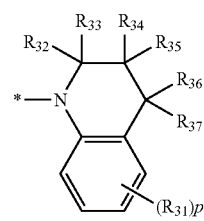

7b

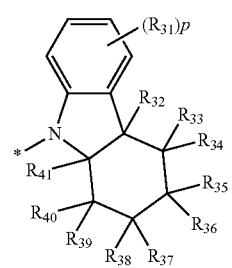

7c

-continued

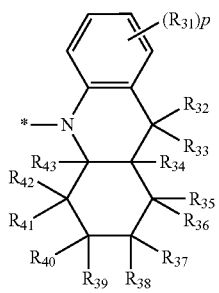
7d

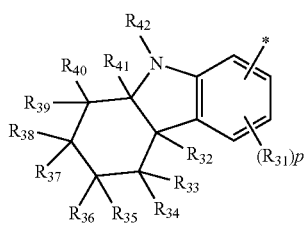
7e

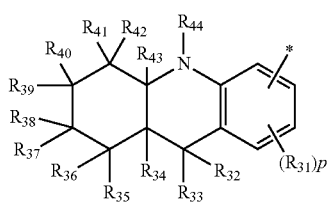
7f

In Formulae 7a to 7f, $R_{31}$ to $R_{44}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

p may be an integer selected from 1 to 4, and when p is 2 or greater, each $R_{31}$ may be identical to or different from each another; and

* is a binding site to a neighboring atom.

According to another embodiment, adjacent substituents or ones of the plurality of $R_{31}$ may be linked to each other and form a ring.

According to another embodiment, in Formula 1, a and d may be each independently an integer selected from 0 to 4, and a sum of a and d may be 4.

According to another embodiment, in Formula 1, b may be 1 or 2, and c may be an integer selected from 1 to 6.

According to another embodiment, the compound represented by Formula 1 may be represented by Formula 2 below:

<Formula 2>

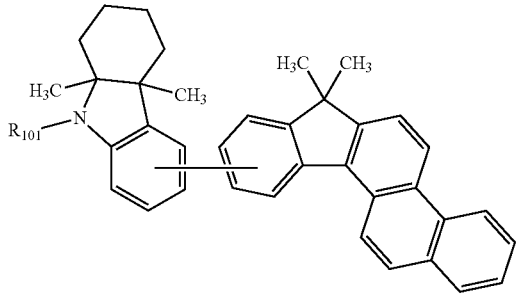

In Formula 2, $R_{101}$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

According to another embodiment, the compound represented by Formula 1 may be represented by Formula 3:

<Formula 3>

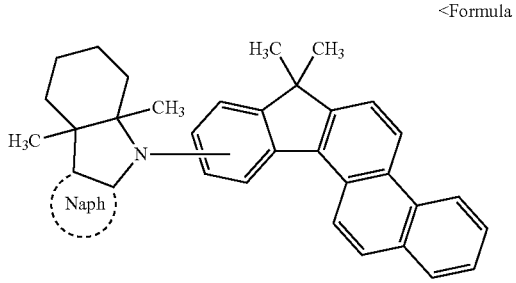

In Formula 3, Naph denotes a naphthyl group.
According to another embodiment, the

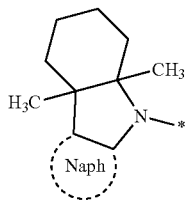

moiety in Formula 3 may be

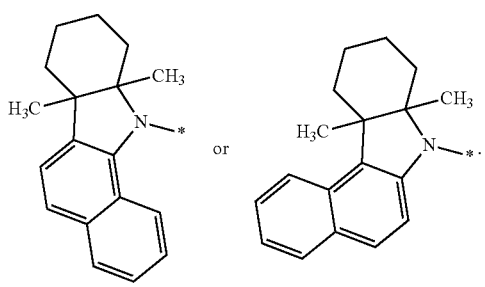 [SMILES: *N1c2c(ccc3ccccc23)C2(C)CCCCC12C ; *N1c2ccc3ccccc3c2C2(C)CCCCC12C]

In formulae of the moiety above, * denotes a binding site to a neighboring atom.
According to another embodiment, the compound represented by Formula 1 may be one of Compounds 1 to 88, below.
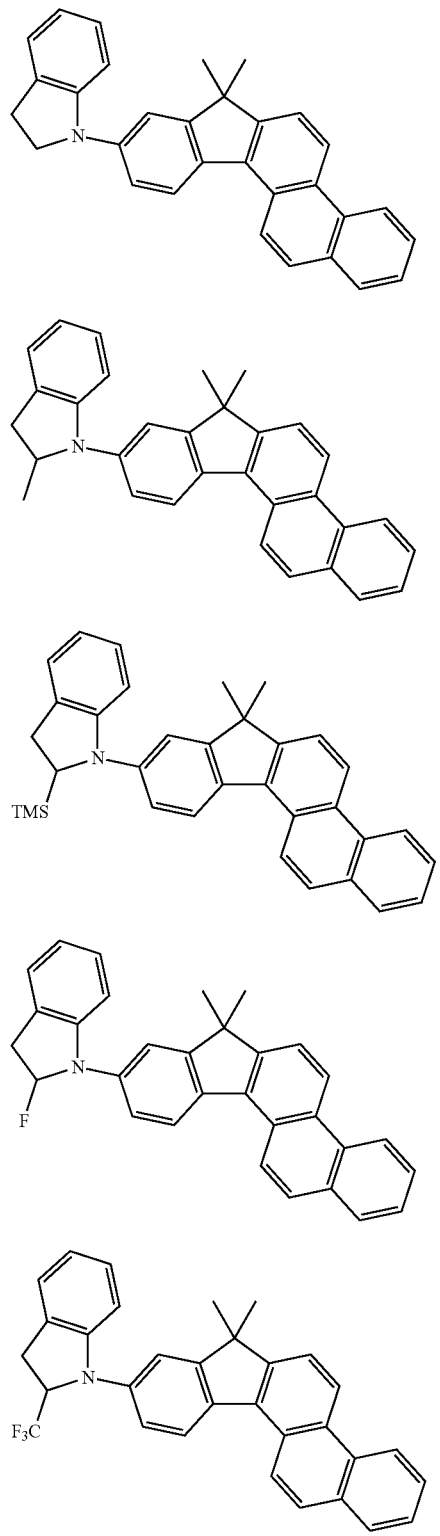
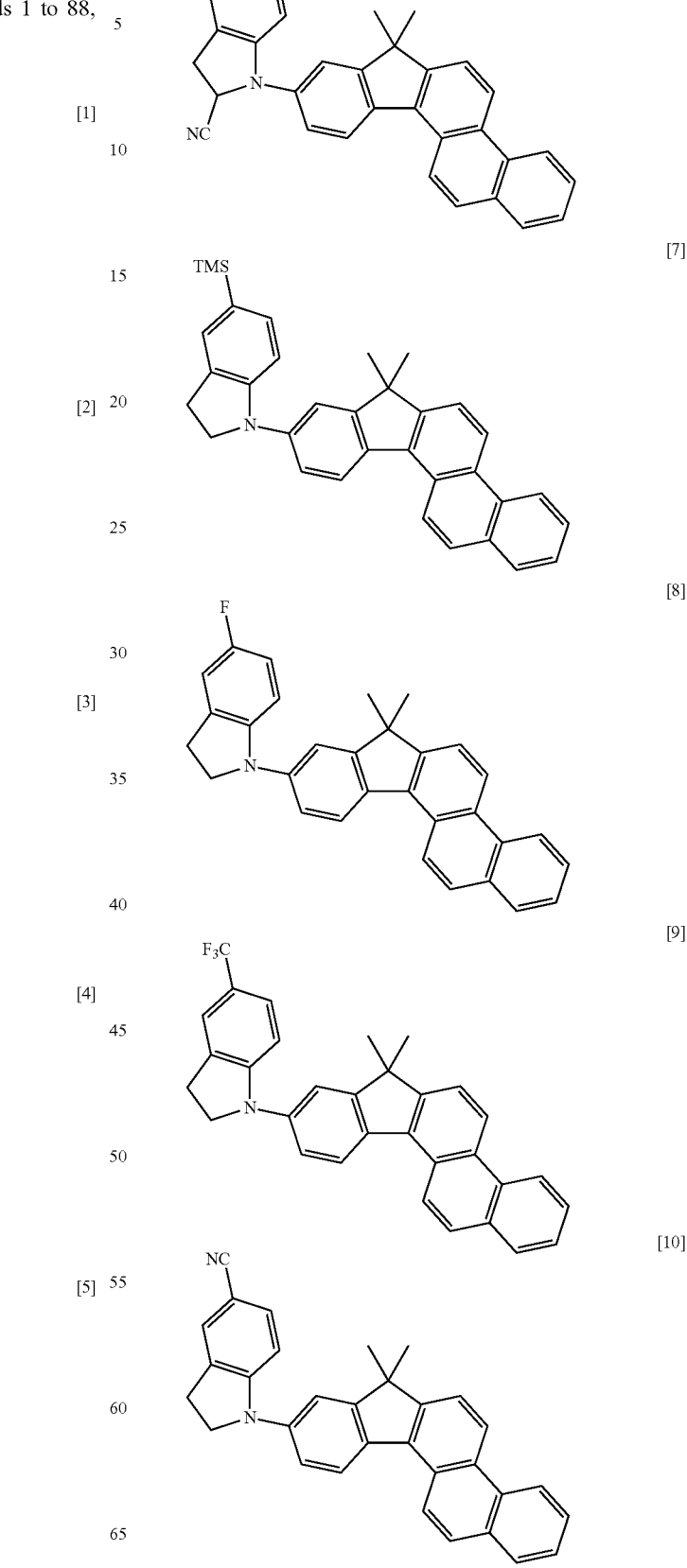

[11]
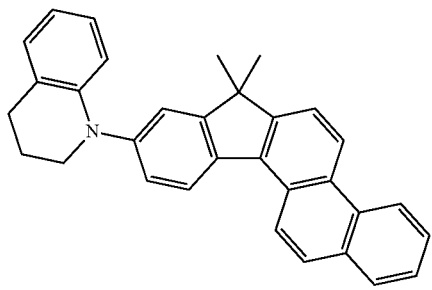
[12]
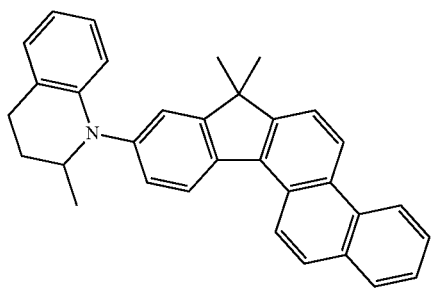
[13]
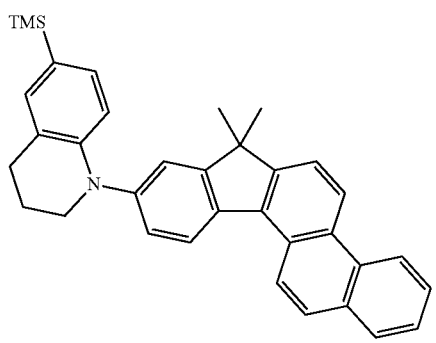
[14]
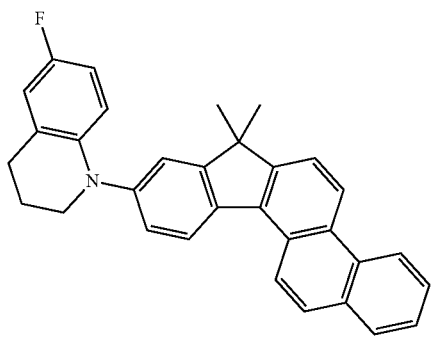
[15]
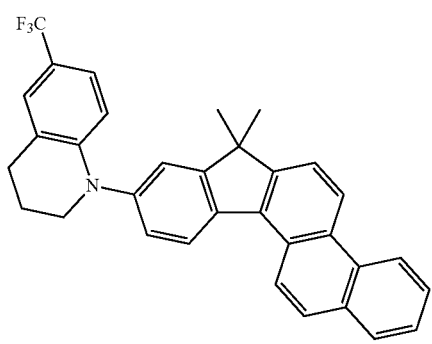
[16]
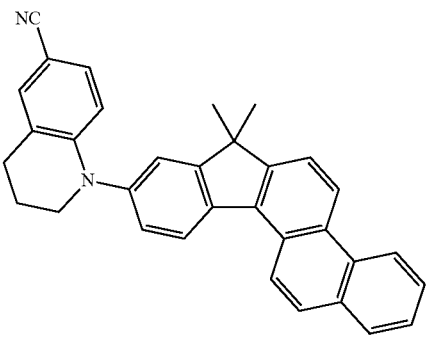
[17]
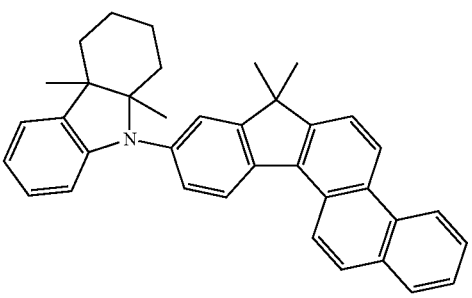
[18]
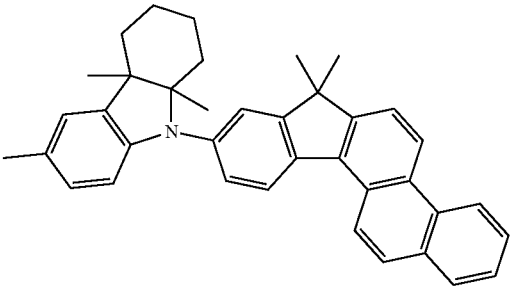
[19]
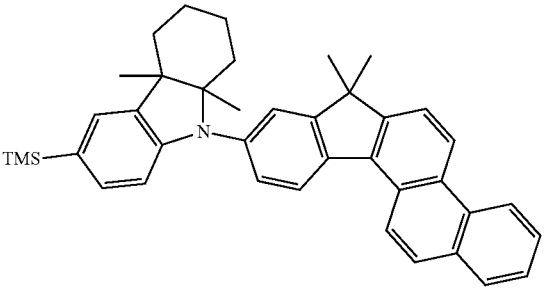
[20]
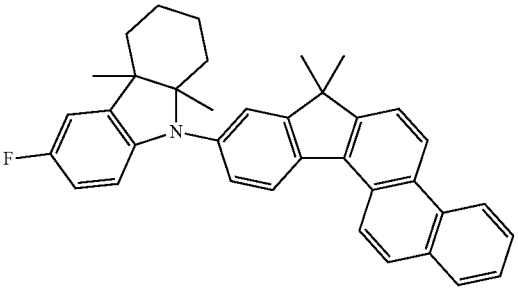

[21]
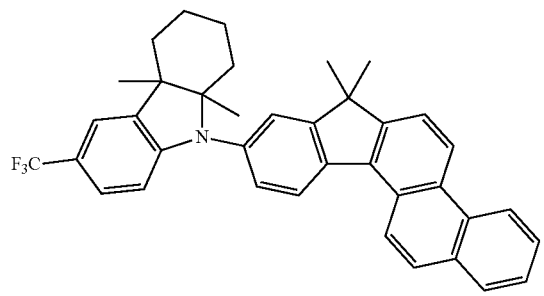
[22]
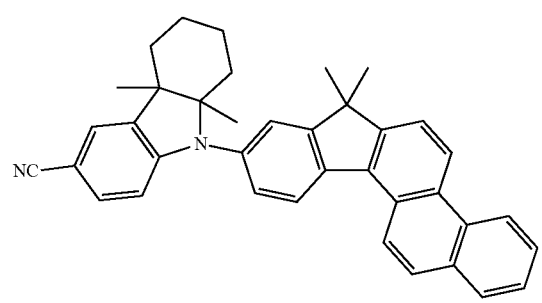
[23]
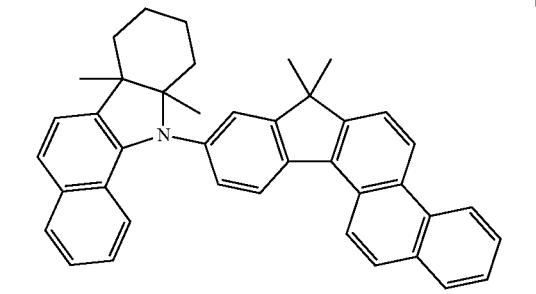
[24]
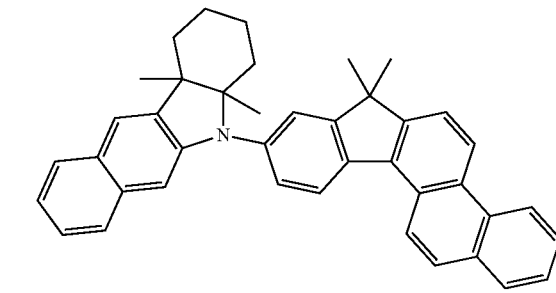
[25]
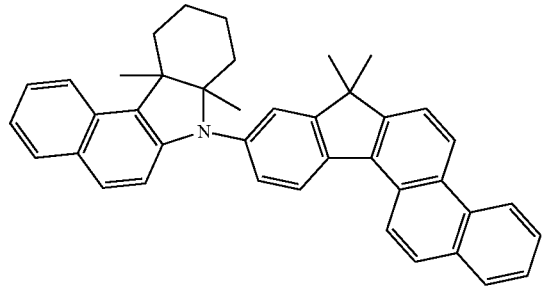
[26]
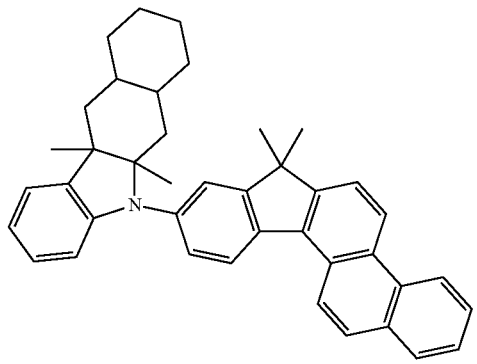
[27]
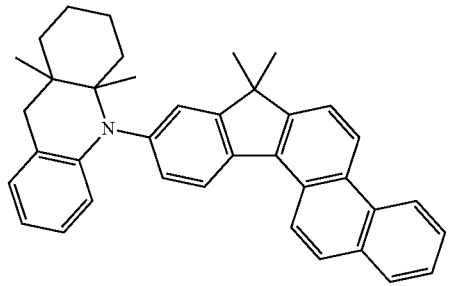
[28]
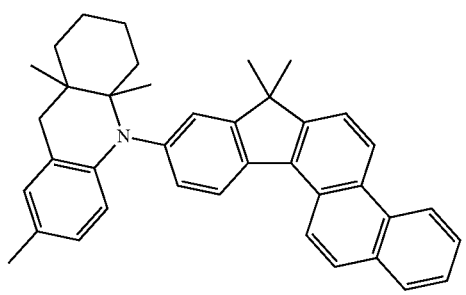
[29]
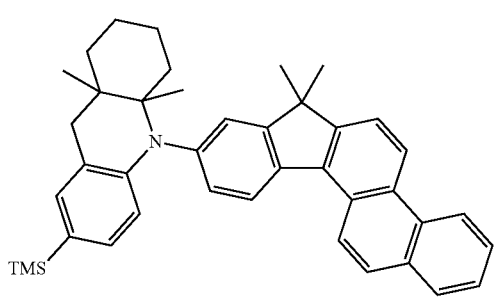
[30]
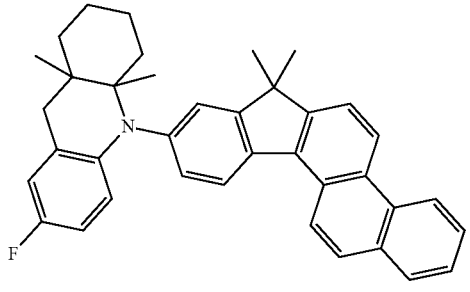

[31]
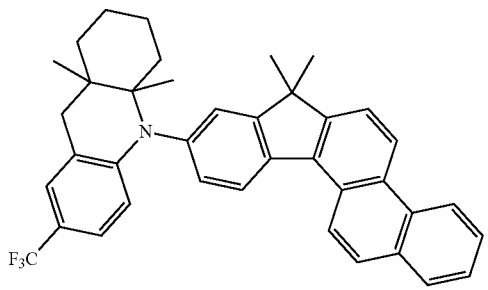
[32]
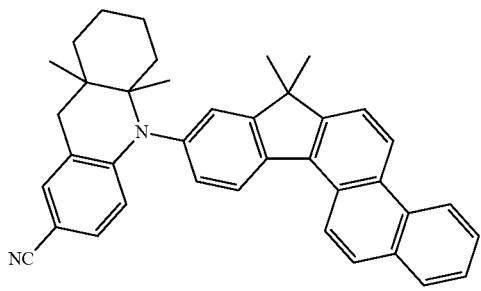
[33]
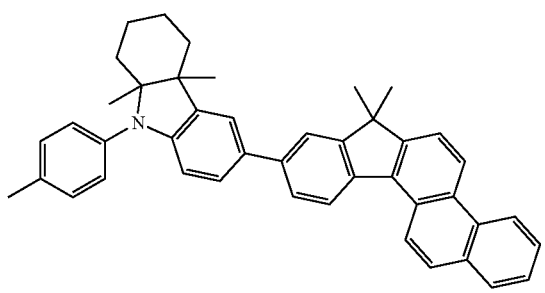
[34]
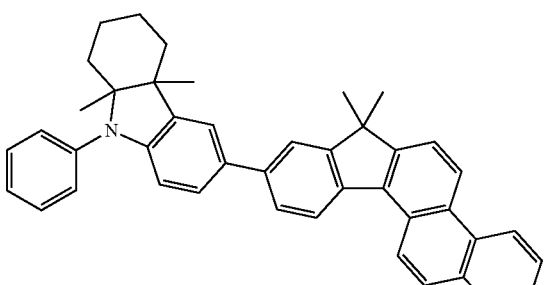
[35]
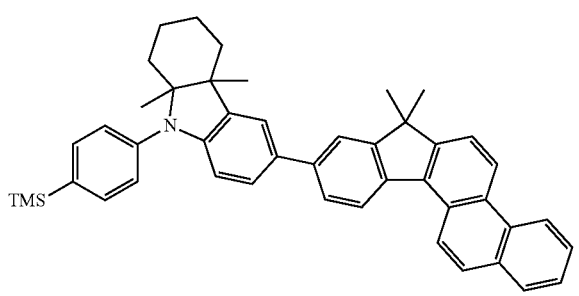
[36]
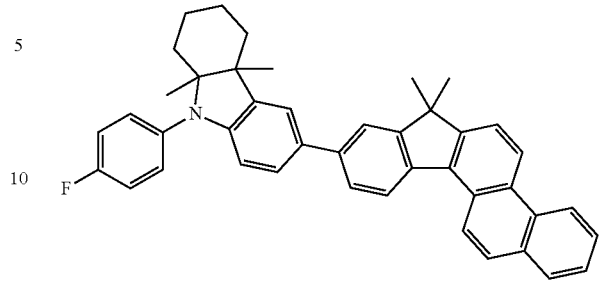
[37]
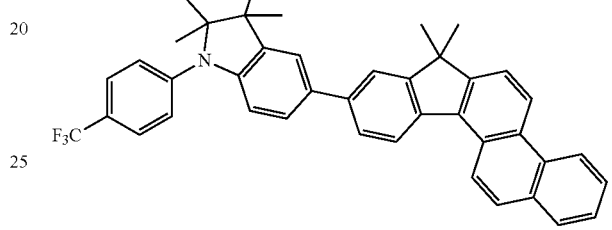
[38]
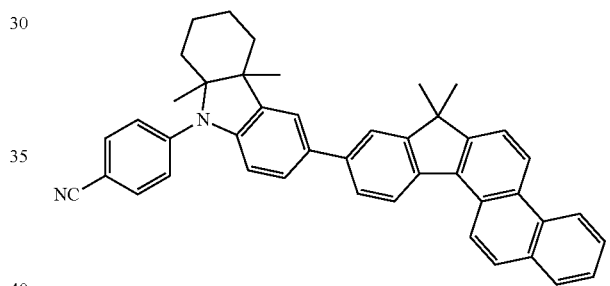
[39]
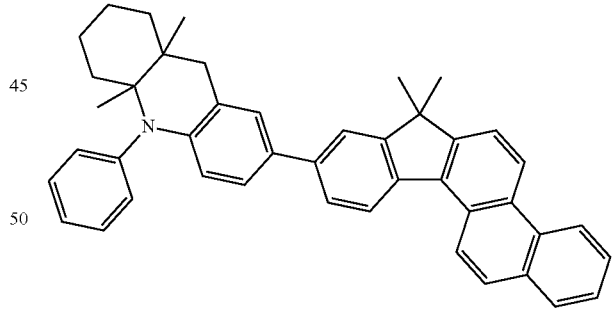
[40]
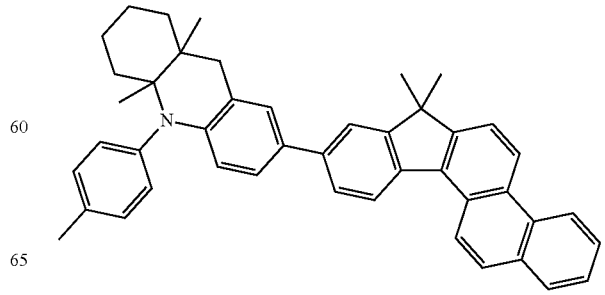

17
-continued
[41]
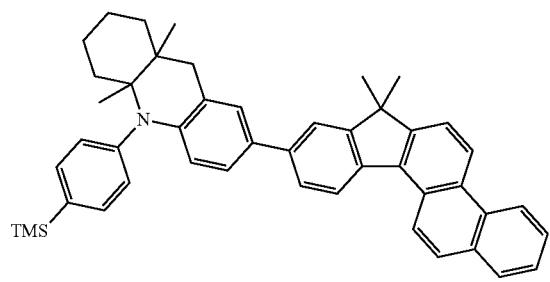
[42]
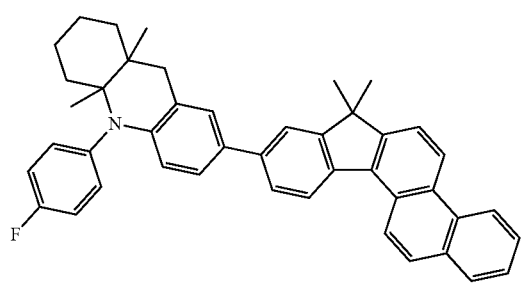
[43]
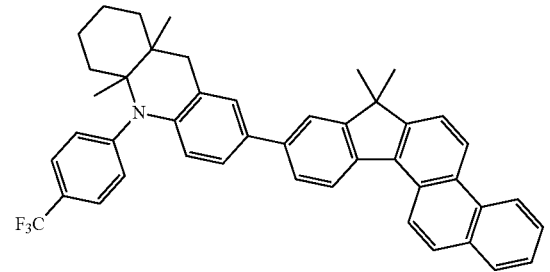
[44]
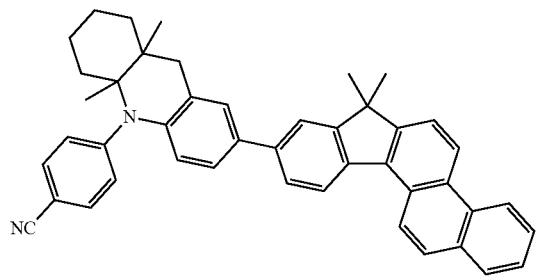
[45]
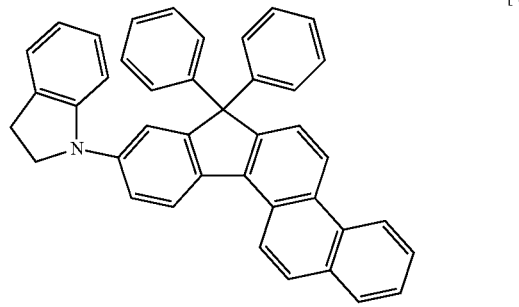
18
-continued
[46]
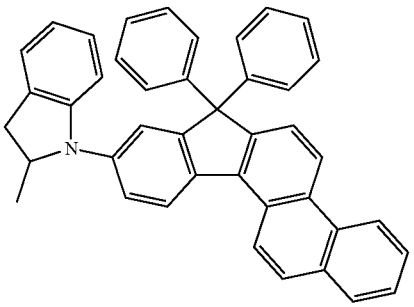
[47]
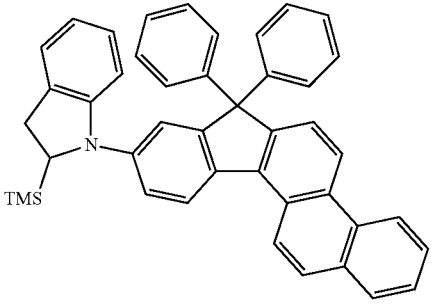
[48]
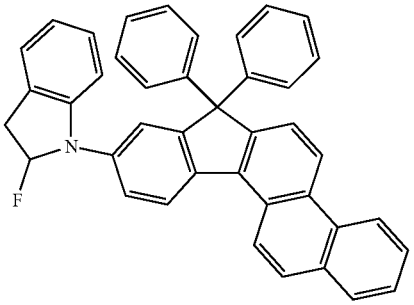
[49]
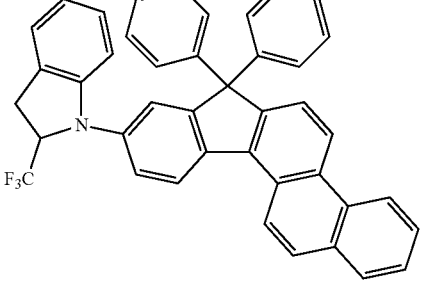
[50]
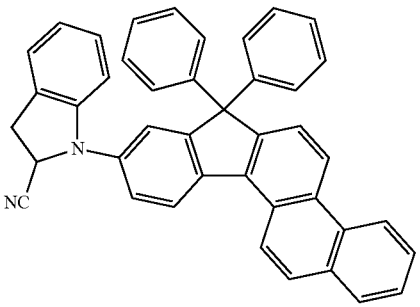

[51]
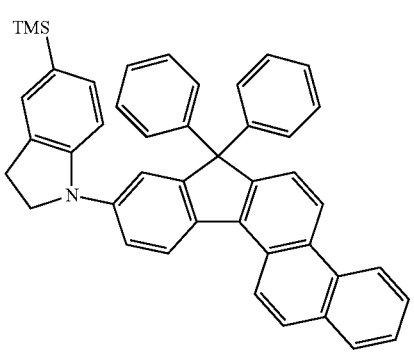
[52]
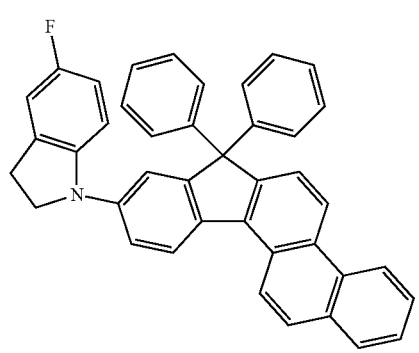
[53]
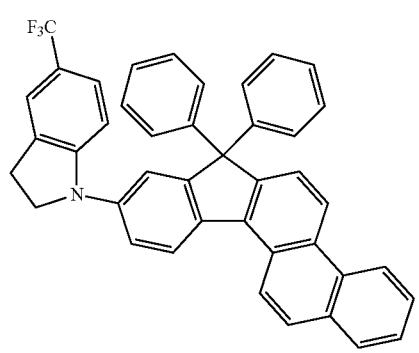
[54]
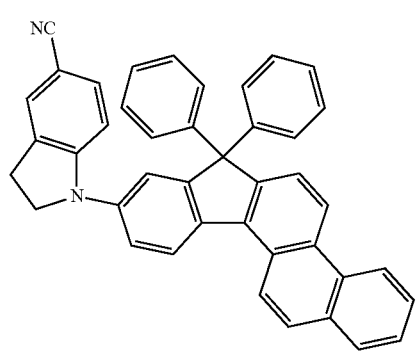
[55]
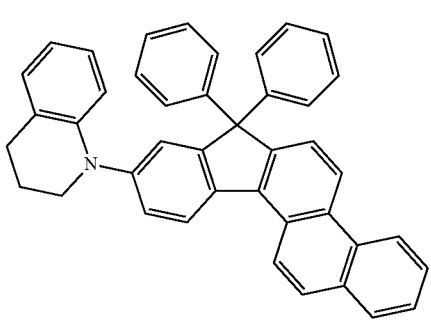
[56]
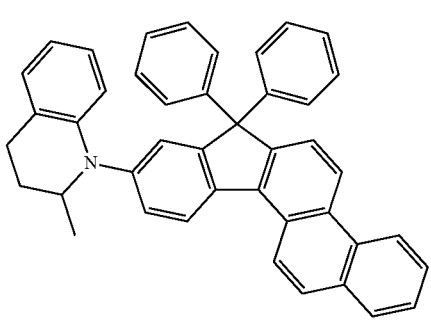
[57]
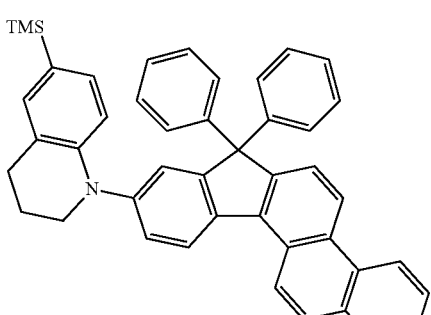
[58]
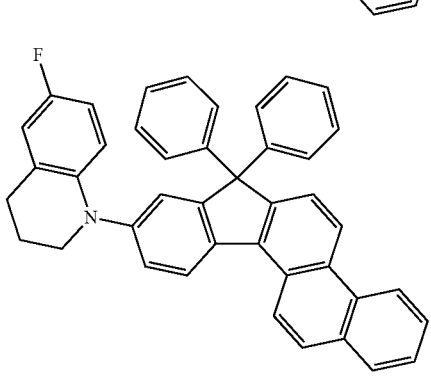
[59]
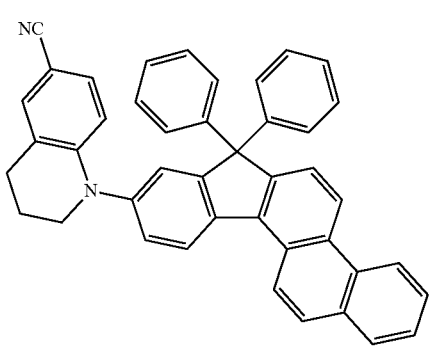

[60]
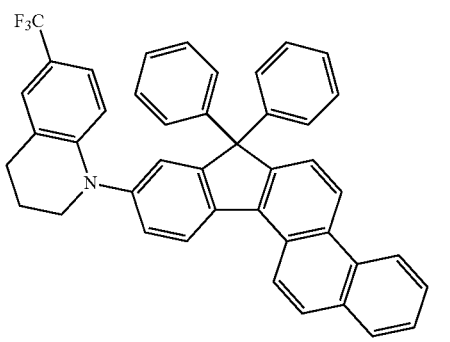
[61]
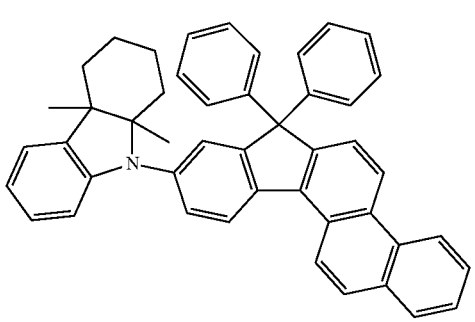
[62]
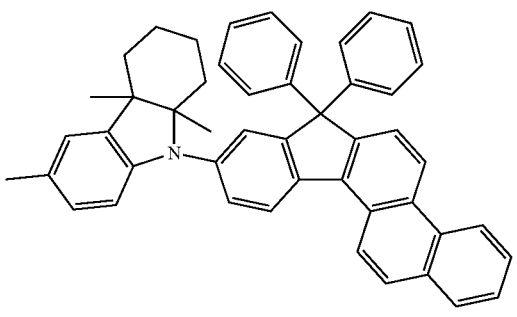
[63]
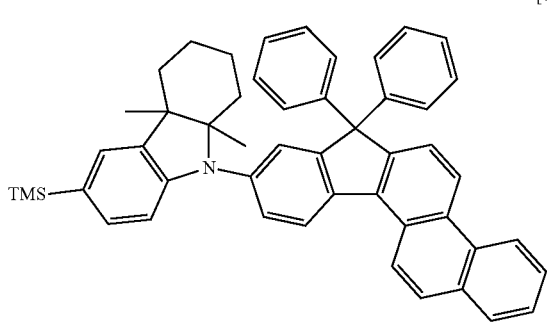
[64]
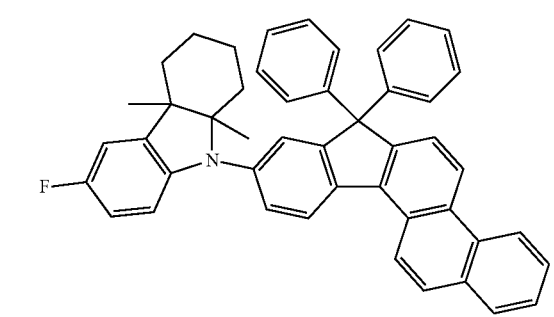
[65]
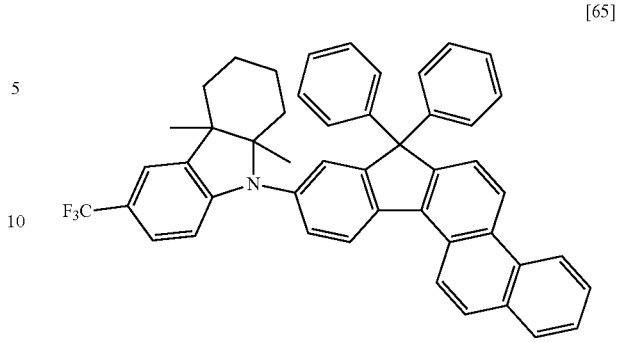
[66]
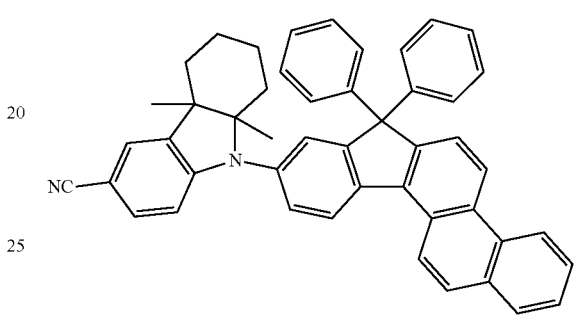
[67]
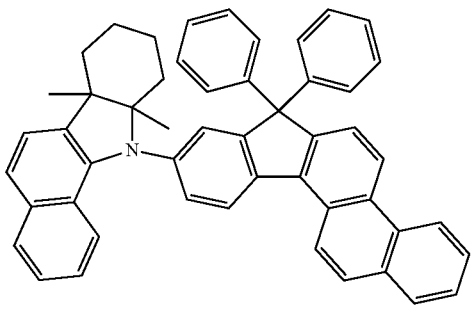
[68]
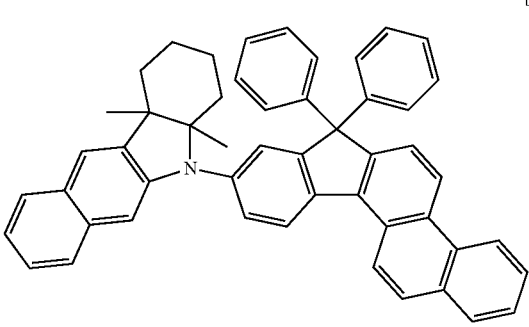
[69]
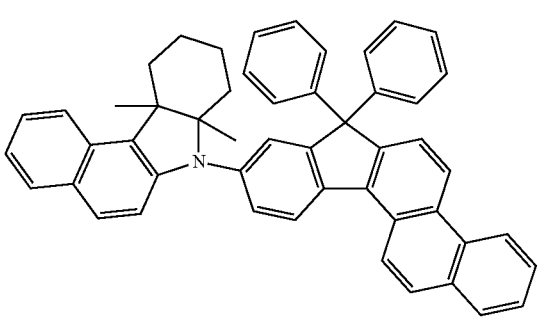

[70]
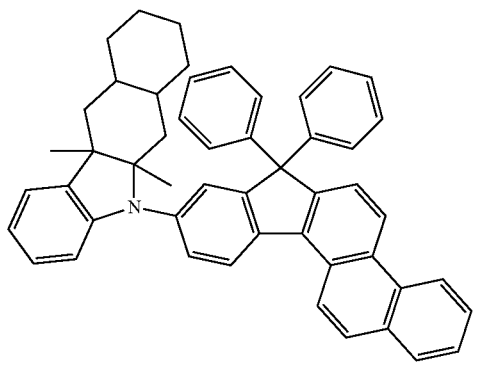
[71]
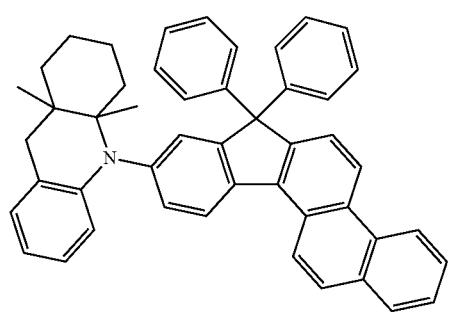
[72]
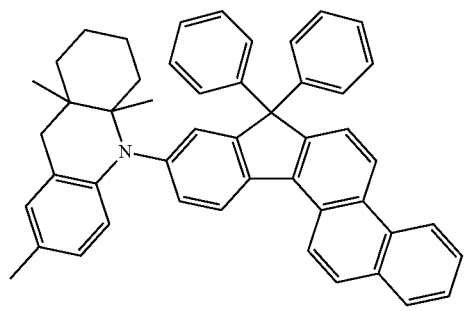
[73]
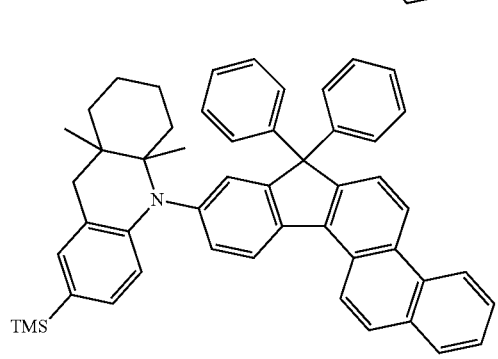
[74]
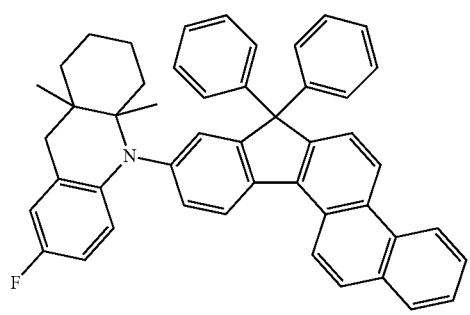
[75]
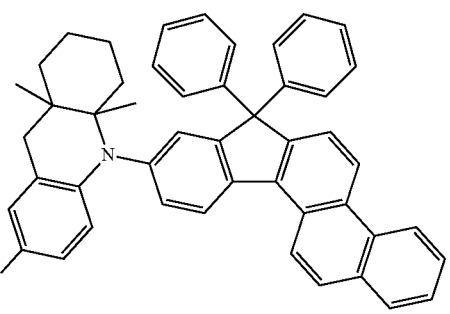
[76]
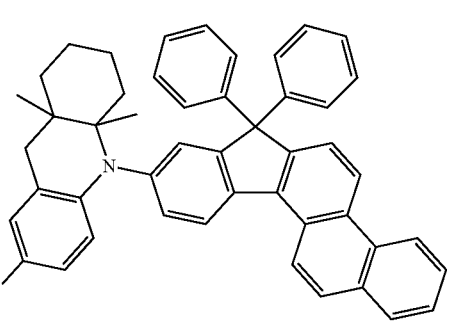
[77]
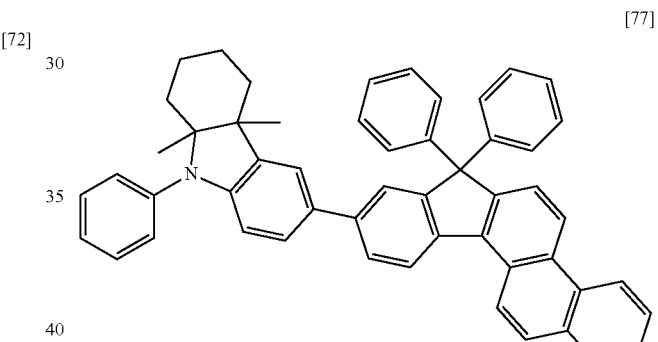
[78]
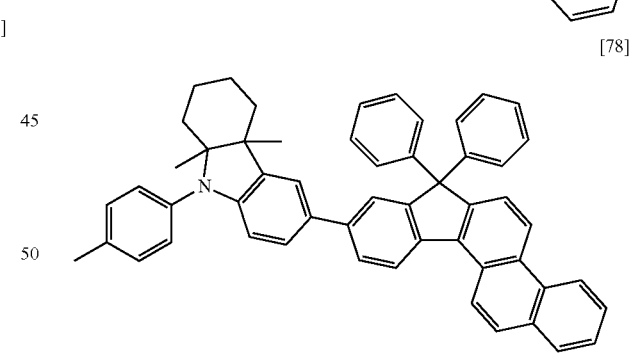
[79]
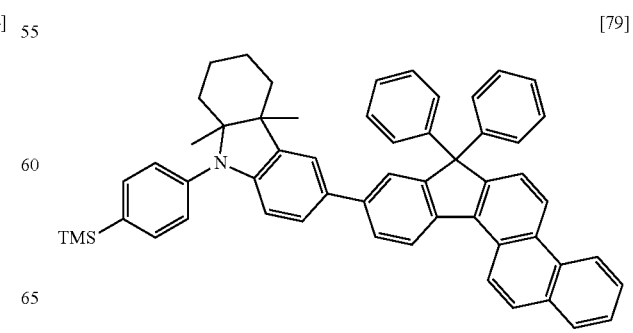

[80]
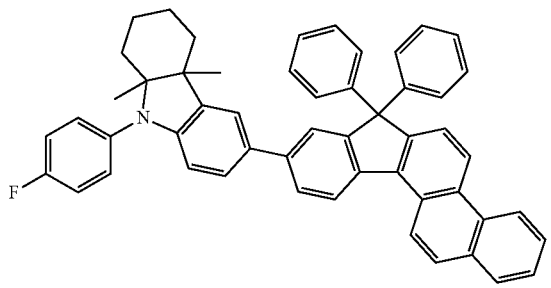

[81]
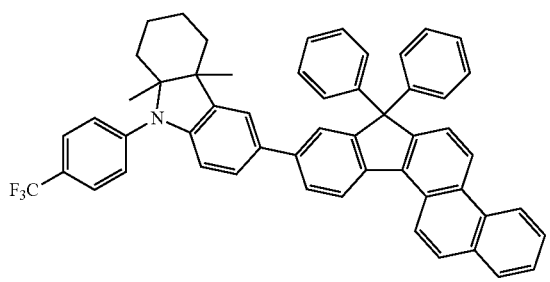

[82]
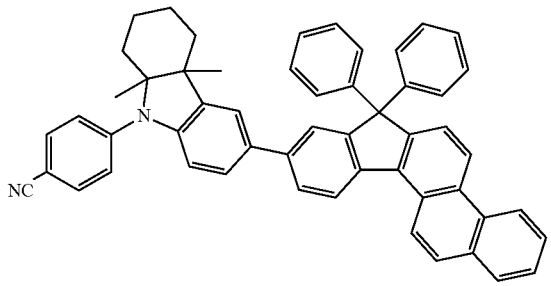

[83]
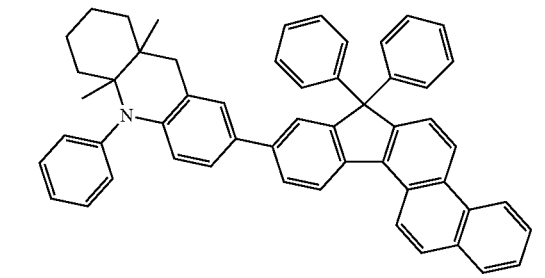

[84]
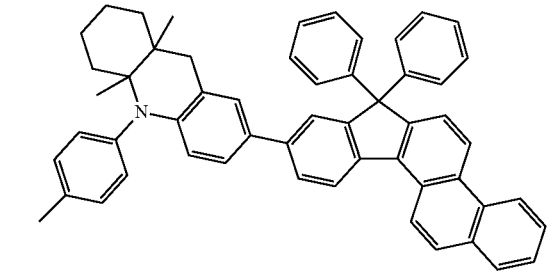

[85]
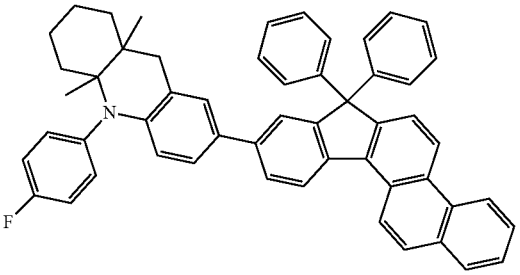

[86]
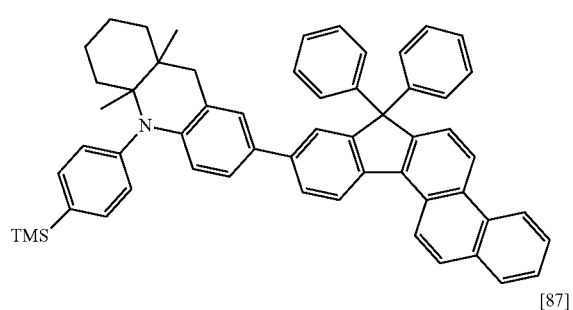

[87]
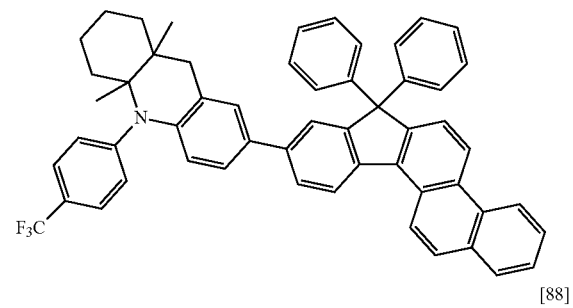

[88]
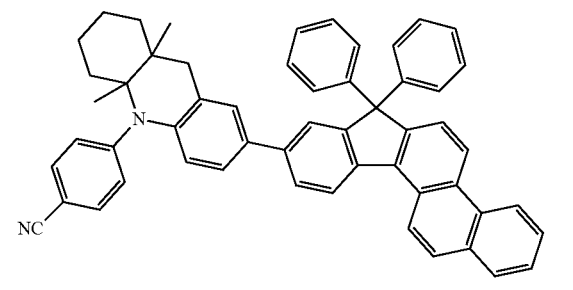

The compound represented by Formula 1 may be synthesized by using a suitable organic synthesis method. The synthesis method may be understood by referring to examples described below.

The compound represented by Formula 1 may be included between a pair of electrodes of an OLED. In an implementation, the compound may be included in an emission layer (EML). Thus, provided is an OLED including a first electrode, a second electrode facing the first electrode, and an organic layer between the first electrode and the second electrode and includes an EML, wherein the organic layer includes the compound represented by Formula 1.

As used herein, the expression "(an organic layer) may include at least one condensed cyclic compound" may be understood as "(an organic layer) may include one condensed cyclic compound represented by Formula 1 or at least two different compounds selected from condensed cyclic compounds represented by Formula 1".

The organic layer may include, e.g., i) a hole transport region that is disposed between the first electrode (an anode) and the EML and includes at least one of a hole injection layer (HIL), a hole transport layer (HTL), a buffer layer, and an electron blocking layer (EBL) and ii) an electron transport region that is disposed between the EML and the second electrode (a cathode) and includes at least one of a hole blocking layer (HBL), an electron transport layer (ETL), and an electron injection layer (EIL). For example, the EML may include the compound represented by Formula 1.

As used herein, the expression "organic layer" refers to a single layer and/or multiple layers disposed between the first electrode and the second electrode of the OLED. However, a material included in the "organic layer" is not limited to an organic material.

The FIGURE illustrates a schematic cross-sectional view of an OLED 10 according to an embodiment. The OLED 10 may include a first electrode 110, an organic layer 150, and a second electrode 190.

Hereinafter, a structure of the OLED 10 and a method of manufacturing the OLED 10 according to an embodiment will be described in detail by referring to the FIGURE.

A substrate may be additionally disposed on a lower part of the first electrode 110 or an upper part of the second electrode 190 of the organic light-emitting device 10 shown in the FIGURE. The substrate may be a glass substrate or a transparent plastic substrate having excellent mechanical strength, thermal stability, transparency, surface smoothness, ease of handling, and water resistance.

The first electrode 110 may be formed by applying a first electrode material on the substrate by deposition or sputtering. When the first electrode 110 is an anode, the first electrode material may be selected from materials having a high work function so that holes may be easily injected. The first electrode 110 may be a reflective electrode, a semi-transparent electrode, or a transparent electrode. Examples of the first electrode material may include indium-tin oxide (ITO), indium-zinc-oxide (IZO), tin oxide ($SnO_2$), and zinc oxide (ZnO). Also, at least one selected from magnesium (Mg), aluminum (Al), aluminum-lithium (Al—Li), a Calcium (Ca), magnesium-indium (Mg—In), and magnesium-silver (Mg—Ag) may be selected as the first electrode material to form the first electrode 110 as a semi-transparent electrode or a reflective electrode.

The first electrode 110 may have a single-layered structure or a multi-layered structure including at least two layers. For example, the first electrode 110 may have a three-layered structure, for example, ITO/Ag/ITO, but a structure of the first electrode 110 is not limited thereto.

The organic layer 150 is disposed on the first electrode 110. The organic layer 150 includes an EML.

The organic layer 150 may further include a hole transport region that is disposed between the first electrode 110 and the EML, and/or an electron transport region that is disposed between the EML and the second electrode 190.

The hole transport region may include at least one selected from an HIL, an HTL, a buffer layer, and an EBL, and the electron transport region may include at least one selected from an HBL, an ETL, and an EIL, but the hole transport region and the electron transport region are not limited thereto.

The hole transport region may have a single layer structure formed of one material, a single layer formed of multiple different materials, or multiple layers formed of multiple different materials.

For example, the hole transport region may have a single layer structure formed of multiple different materials or a structure of HIL/HTL, HIL/HTL/buffer layer, HIL/buffer layer, HTL/buffer layer, or HIL/HTL/EBL sequentially stacked on the first electrode 110, but a structure of the hole transport region is not limited thereto.

When the hole transport region includes an HIL, the HIL may be formed on the first electrode 110 by using various methods such as vacuum deposition, spin coating, casting, Langmuir-Blodgett (LB) deposition, inkjet printing, laser printing, or laser induced thermal imaging (LITI).

When the HIL is formed by vacuum deposition, the deposition conditions may be selected from ranges of, for example, a deposition temperature of about 100 to about 500° C., a degree of vacuum of about $10^{-8}$ to about $10^{-3}$ torr, and a deposition speed of about 0.01 to about 100 Å/sec, in consideration of a desired compound for the HIL and a desired structure of the HIL.

When the HIL is formed by spin coating, the deposition conditions may be selected from ranges of, e.g., a coating speed of about 2,000 rpm to about 5,000 rpm and a heat treatment temperature of about 80° C. to about 200° C. in consideration of a desired compound for the HIL and a desired structure of the HIL.

When the hole transport region includes the HTL, the HTL may be formed on the first electrode 110 or on the HIL by using various methods such as vacuum deposition, spin coating, casting, LB deposition, inkjet printing, laser printing, or LITI. When the HTL is formed by vacuum deposition and spin coating, the deposition conditions and the coating conditions of the HTL may be referred to the deposition conditions and the coating conditions of the HIL.

The hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine) (TCTA), polyaniline/Dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), polyaniline)/poly(4-styrenesulfonate (PANI/PSS), a compound represented by Formula 201, and a compound represented by Formula 202:

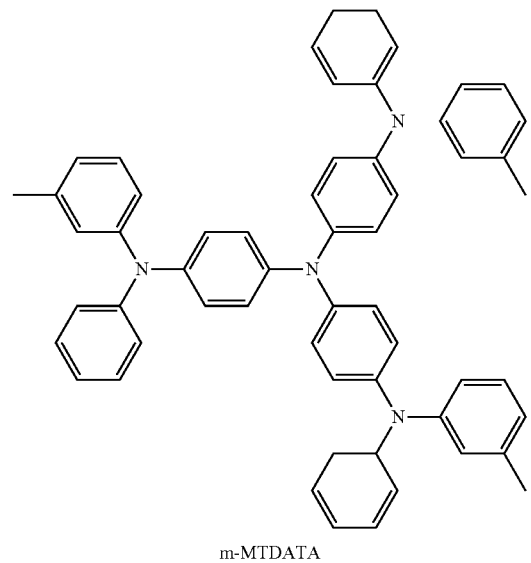

m-MTDATA

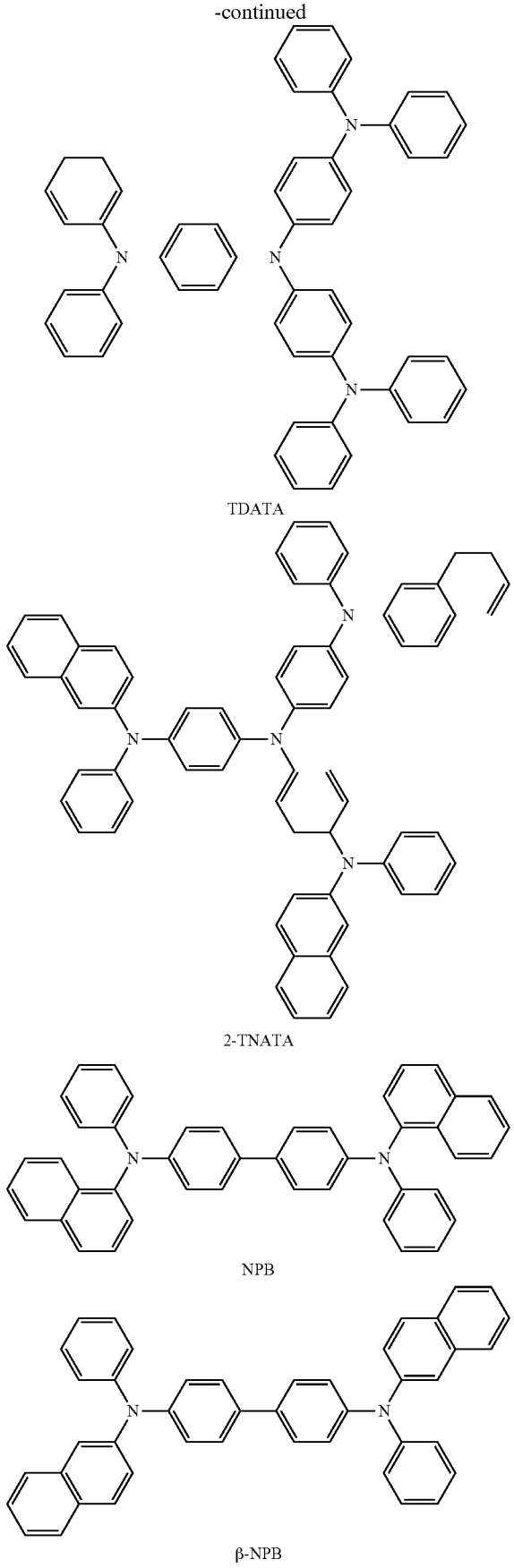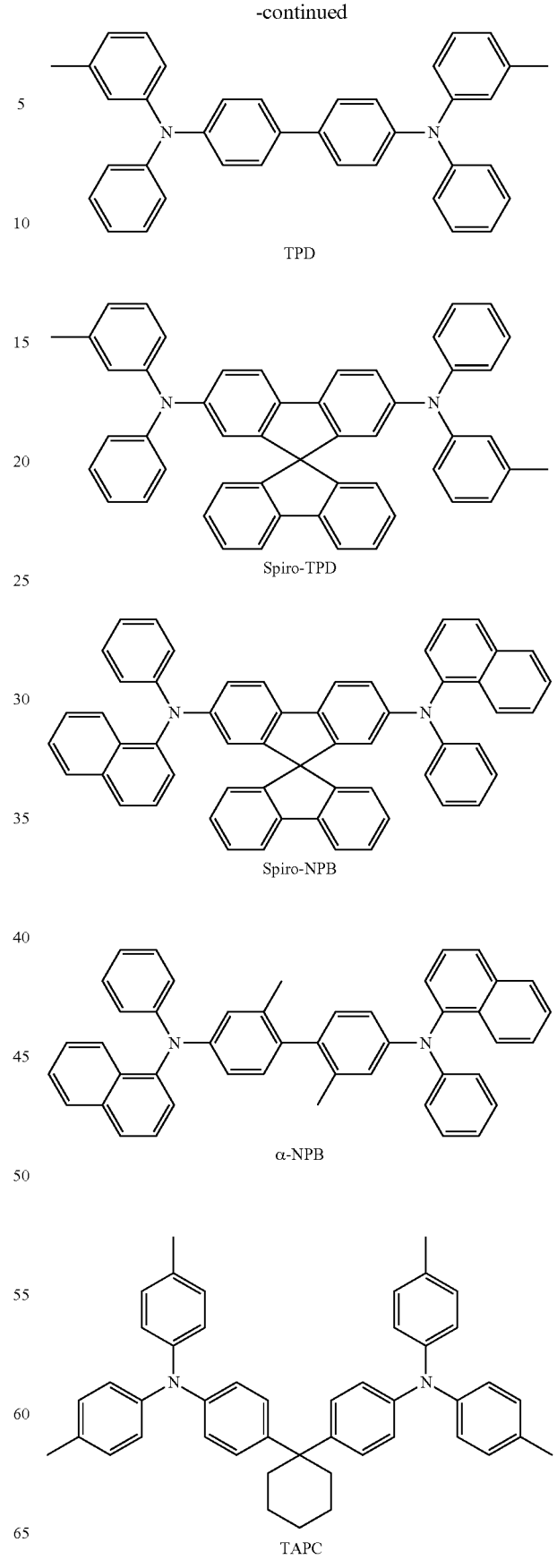

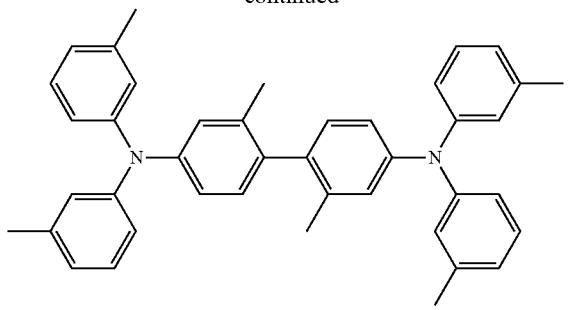

HMTPD

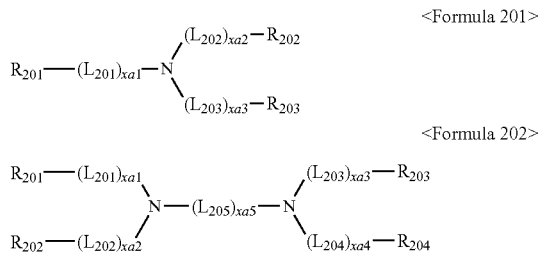

<Formula 201>

<Formula 202>

In Formulae 201 and 202, descriptions of $L_{201}$ to $L_{205}$ may be each independently referred to the description of L of Formula 1 in the present specification;

xa1 to xa4 may be each independently an integer selected from 0, 1, 2, and 3;

xa5 may be an integer selected from 1, 2, 3, 4, and 5; and;

$R_{201}$ to $R_{204}$ may be each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic heterocondensed polycyclic group.

For example, in Formulae 201 and 202, $L_{201}$ to $L_{205}$ may be each independently selected from, a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently an integer selected from 0, 1, and 2;

xa5 may be an integer selected from 1, 2, and 3;

$R_{201}$ to $R_{204}$ may be each independently selected from, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A below, but the compound is not limited thereto.

<Formula 201A>

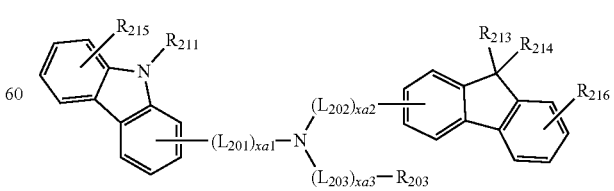

For example, the compound represented by Formula 201 may be represented by Formula 201A-1:

<Formula 201A-1>

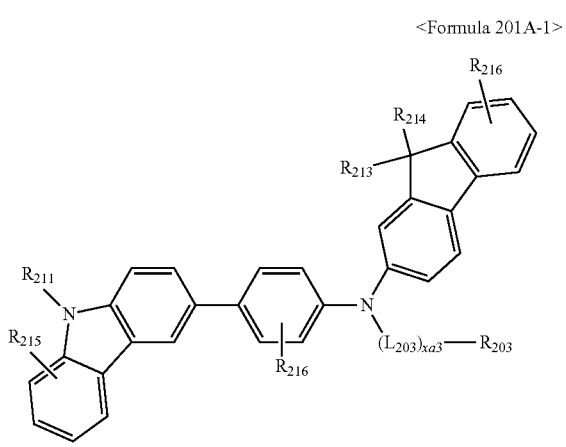

The compound represented by Formula 202 may be represented by Formula 202A, but the compound is not limited thereto.

<Formula 202A>

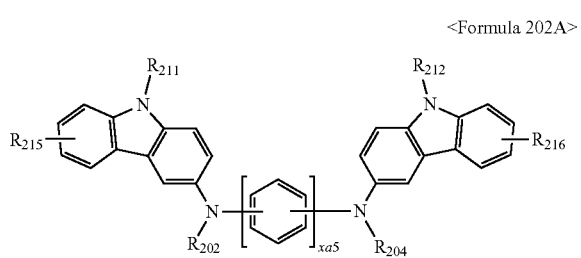

In Formulae 201A, 201A-1, and 202A, descriptions of $L_{201}$ to $L_{203}$, xa1 to xa3, xa5, and $R_{202}$ to $R_{204}$ may be referred to the descriptions defined in the present specification, description of $R_{211}$ may be referred to the description of $R_{203}$, $R_{213}$ to $R_{216}$ may be each independently selected from, but are not limited to, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic heterocondensed polycyclic group.

For example, in Formula 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently an integer selected from 0 and 1;

$R_{203}$, $R_{211}$, and $R_{212}$ may be each independently selected from, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In an implementation, in Formulae 201A and 201A-1, $R_{213}$ and $R_{214}$ may link to each other and form a saturated or unsaturated ring.

The compound represented by Formula 201 and the compound represented by Formula 202 may each independently include Compounds HT1 to HT20 below, but the compounds are not limited thereto:

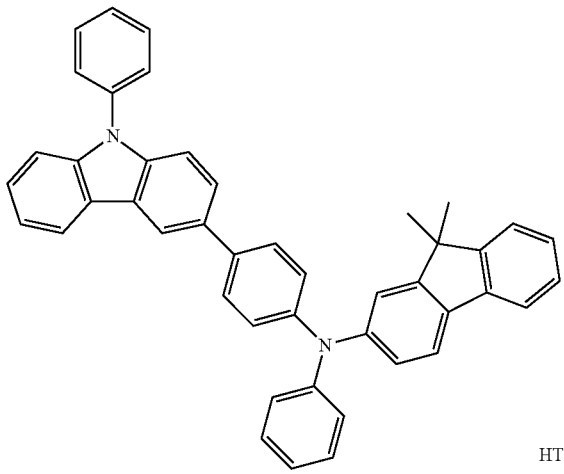

HT1

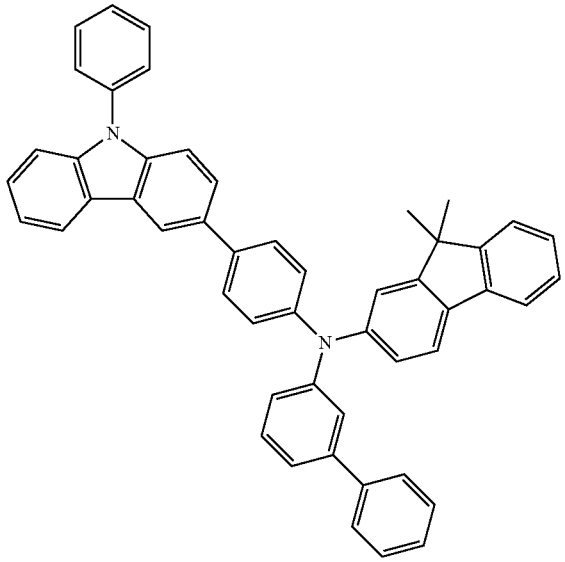

HT2

HT3
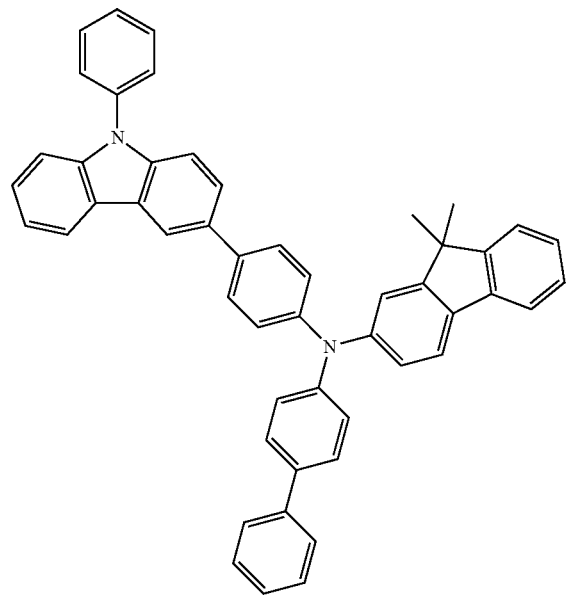
HT5
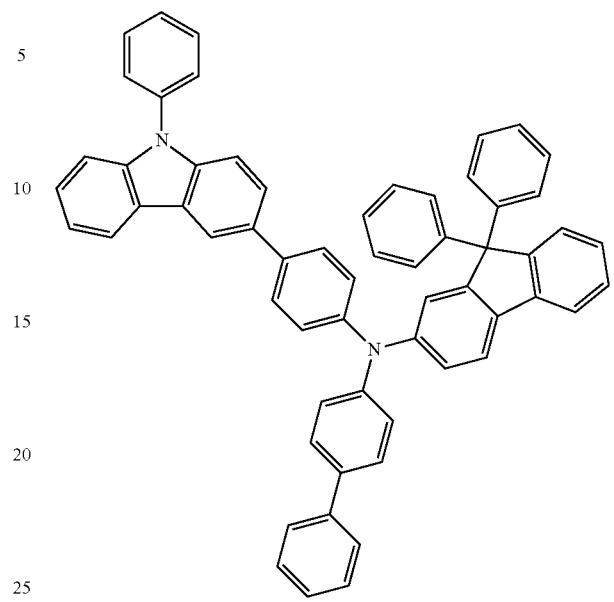
HT4
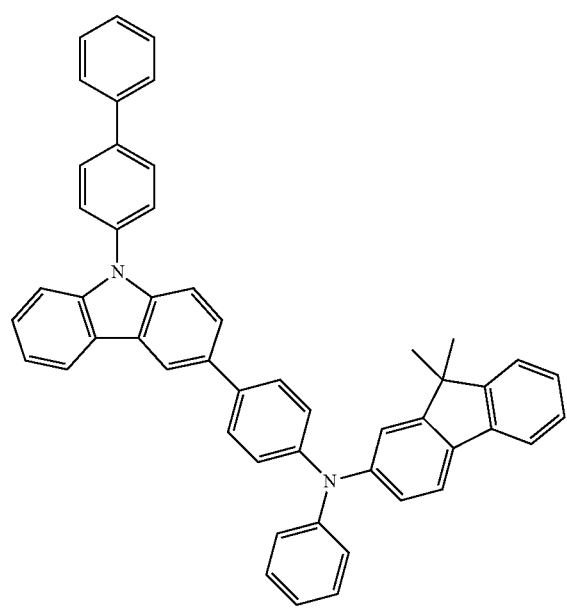
HT6
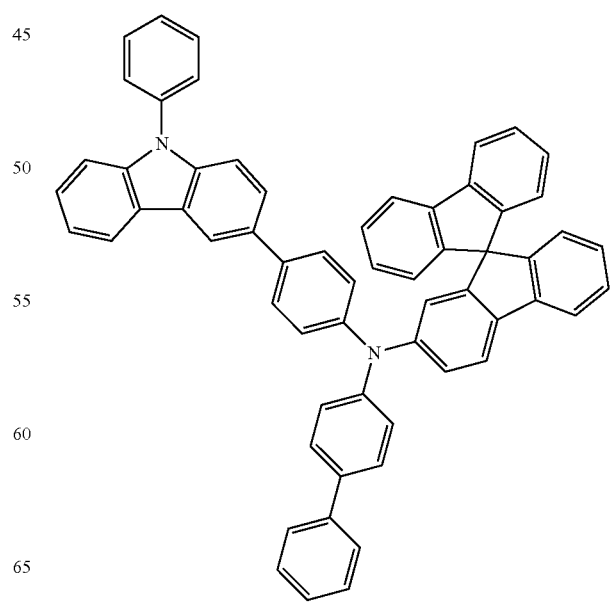

HT7
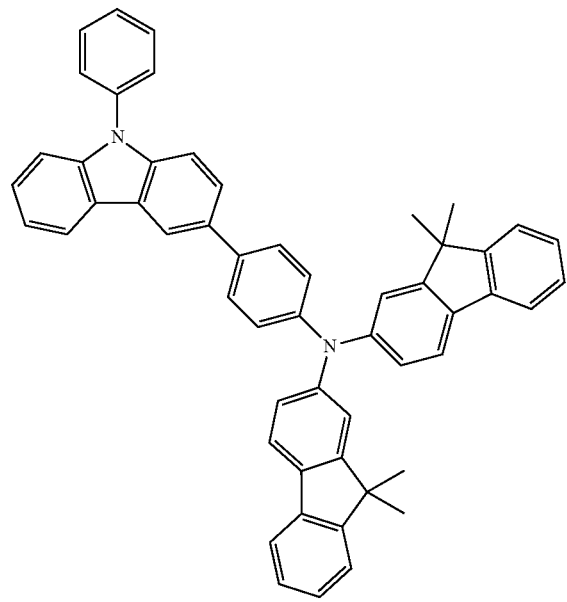
HT9
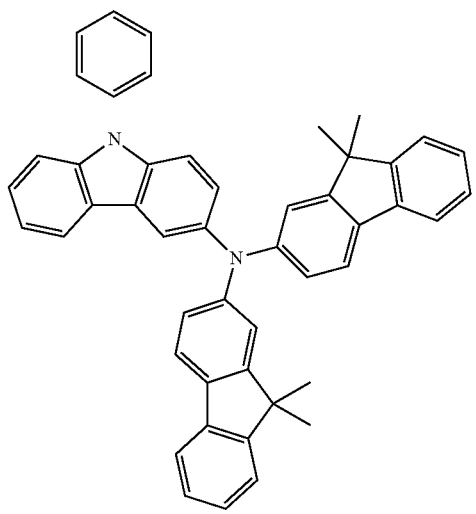
HT8
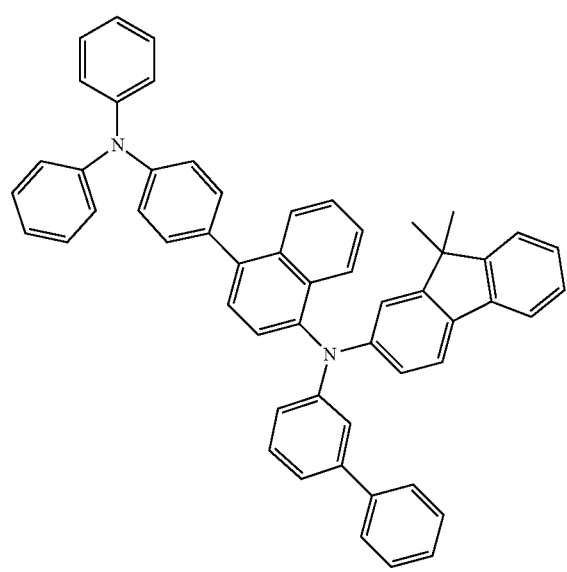
HT10
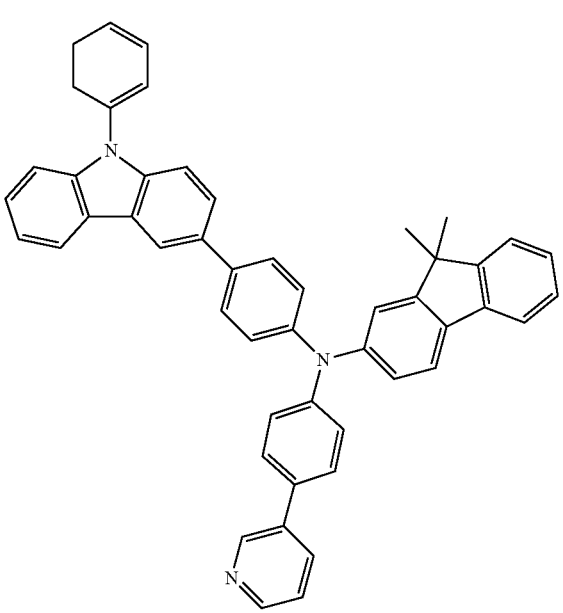

HT11
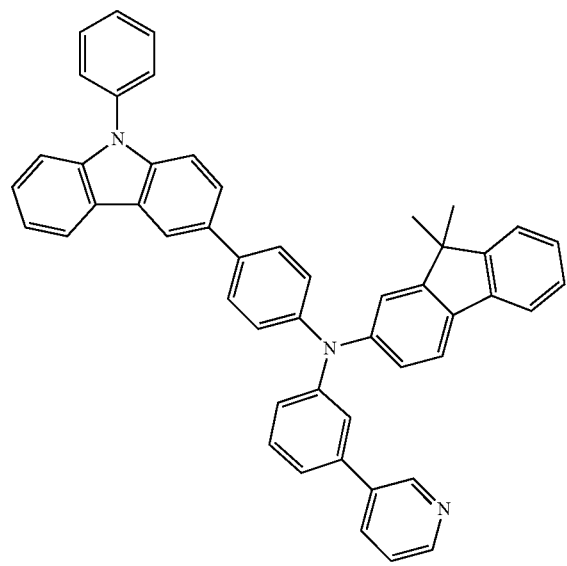
HT14
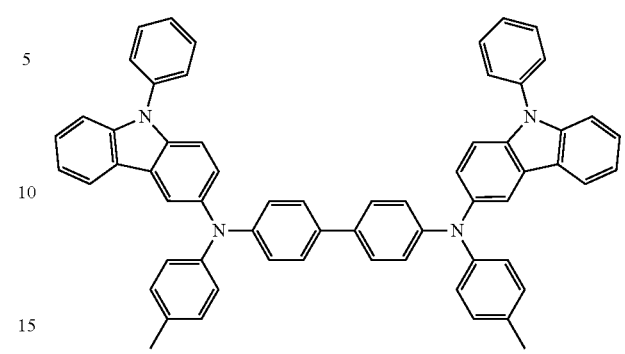
HT15
HT12
HT16
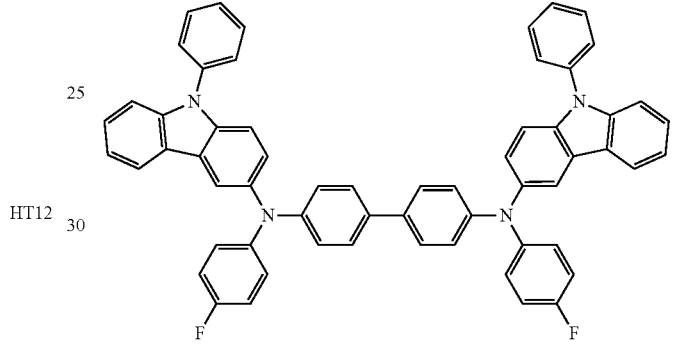
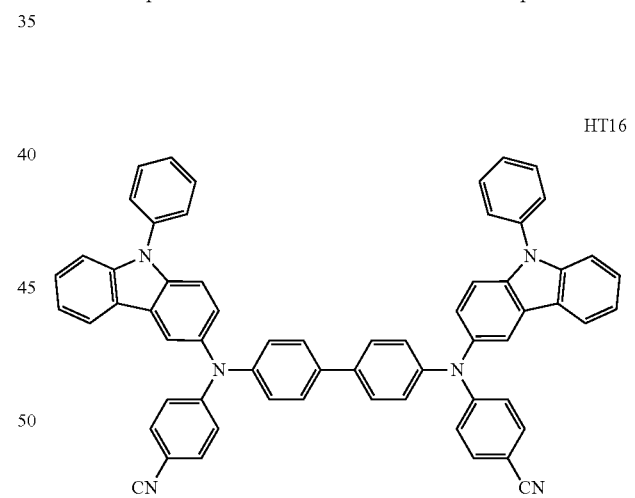
HT13
HT17
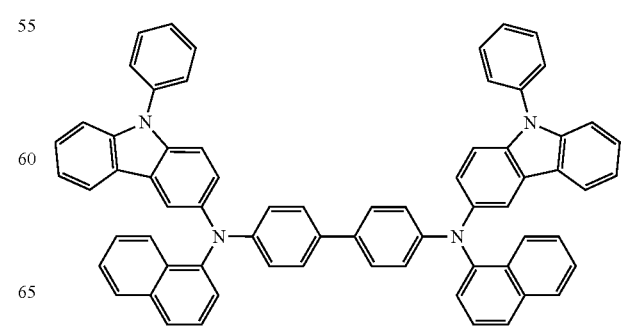

HT18

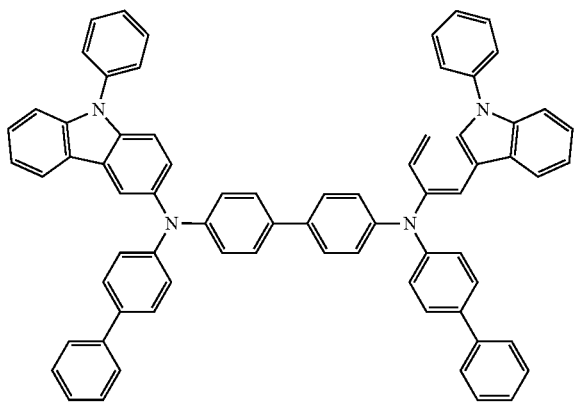

HT19

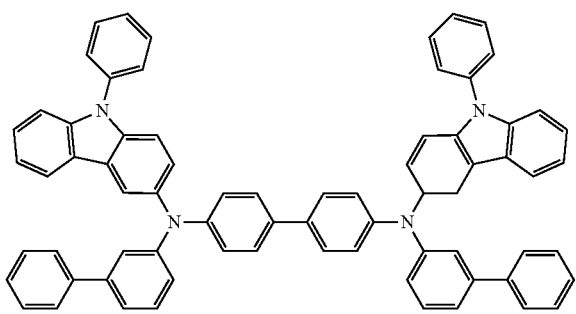

HT20

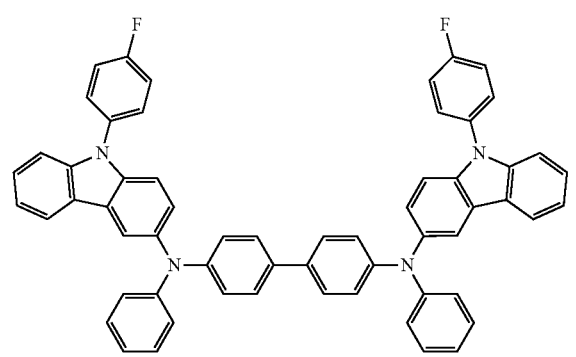

A thickness of the hole transport region may be in a range of about 100 Å to about 10,000 Å, e.g., about 100 Å to about 1,000 Å. When the hole transport region includes both the HIL and the HTL, a thickness of the HIL may be in a range of about 100 Å to about 10,000 Å, e.g., about 100 Å to about 1,000 Å, and a thickness of the HTL may be in a range of about 50 Å to about 2,000 Å, e.g., about 100 Å to about 1,500 Å. When thicknesses of the hole transport region, the HIL, and the HTL are within these ranges, hole transporting properties of the organic light-emitting device may be satisfactory without substantial increase in driving voltage.

The hole transport region may further include a charge-generating material, in addition to the materials above, to help improve conductivity. The charge-generating material may be homogenously or unhomogenously dispersed in the hole transport region.

The charge-generating material may be, e.g., a p-dopant. The p-dopant may include one of a quinone derivative, a metal oxide, and a cyano group-containing compound, but the p-dopant is not limited thereto. Examples of the p-dopant may include a quinone derivative, such as a tetracyanoquinonedimethane (TCNQ) and 2,3,5,6-tetrafluoro-tetracyano-1,4-benzoquinondimethane (F4-TCNQ); a metal oxide, such as a tungsten oxide or a molybden oxide; and Compound HT-D1 below, but the examples are not limited thereto:

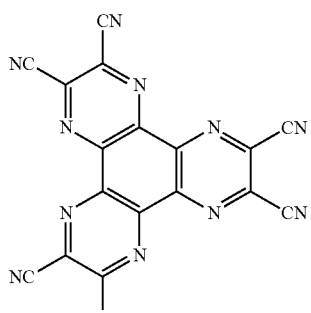

<Compound HT-D1>

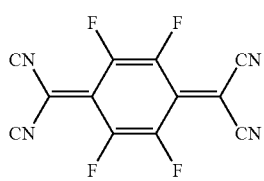

<F4-TCNQ>

The hole transport region may further include at least one of a buffer layer or an EBL in addition to the HIL and the HTL. The buffer layer may help increase light-emitting efficiency by compensating an optical resonance distance according the wavelength of light emitted from the EML 13. The buffer layer may include a material that may be included in the hole transport region. The EBL may block injection of electrons from the electron transport region.

The EML may be formed on the first electrode 110 or on the hole transport region by using various methods such as vacuum deposition, spin coating, casting, LB deposition, inkjet printing, laser printing, or LITI. When the EML is formed by vacuum deposition and spin coating, the deposition conditions and the coating conditions of the EML may be referred to the deposition conditions and the coating conditions of the HIL.

When the organic light-emitting device 10 is a full-color organic light-emitting device, the EML may be patterned according to individual sub-pixels, such as a red EML, a green EML, and a blue EML. In an implementation, the EML may have a stacked structure of the red EML, the green EML, and the blue EML or a single layer structure including a red light-emitting material, a green light-emitting material, and a blue light-emitting material formed as a single layer and thus may emit white light.

The EML may include a host and a dopant.

Examples of the host may include at least one of TPBi, TBADN, ADN (also referred to as "DNA"), CBP, CDBP, and TCP:

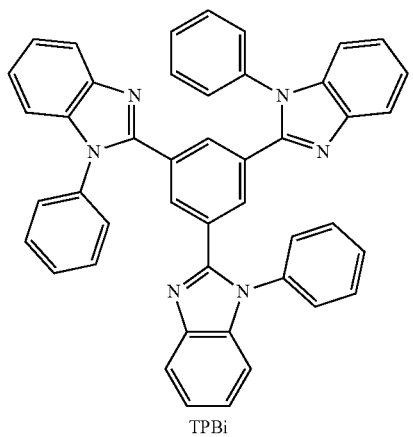

TPBi

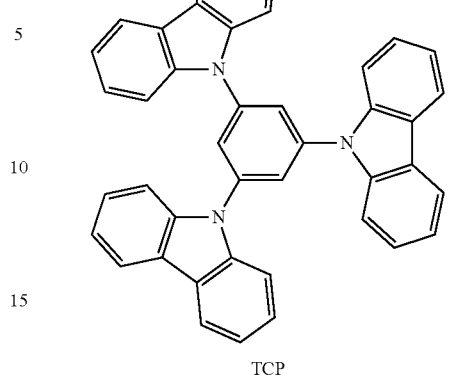

TCP

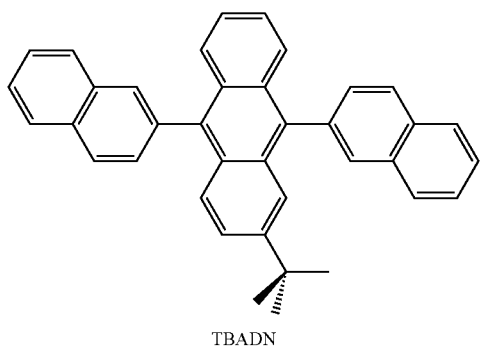

TBADN

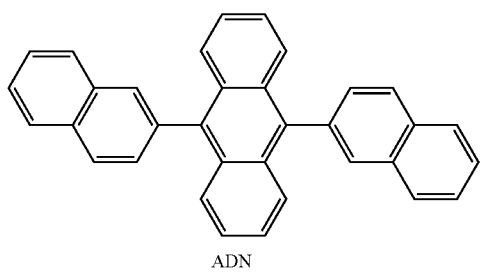

ADN

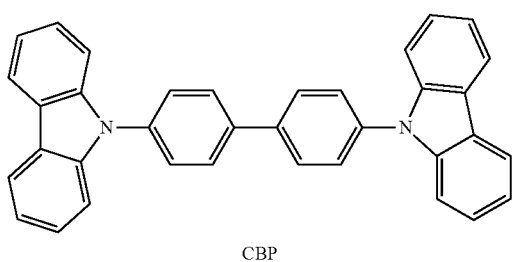

CBP

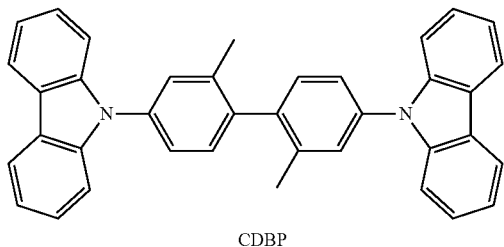

CDBP

In an implementation, the host may include a compound represented by Formula 301:

$$Ar_{301}-[(L_{301})_{xb1}-R_{301}]_{xb2} \qquad \text{<Formula 301>}$$

In Formula 301, $Ar_{301}$ may be selected from, a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, and —Si($Q_{301}$)($Q_{302}$)($Q_{303}$) (here, $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

description of $L_{301}$ may be referred to the description of $L_{201}$ of the present specification;

$R_{301}$ may be selected from, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be an integer selected from 0, 1, 2, and 3; and xb2 may be an integer selected from 1, 2, 3, and 4.

For example, in Formula 301, $L_{301}$ may be selected from, a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but $R_{301}$ is not limited thereto.

For example, the host may include a compound represented by Formula 301A:

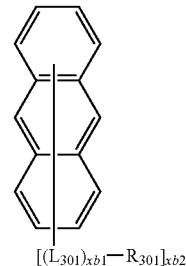

<Formula 301A>

$[(L_{301})_{xb1}$—$R_{301}]_{xb2}$

In Formula 301A, descriptions of the substituents may be referred to the descriptions in the present specification.

The compound represented by Formula 301A may include at least one of Compounds H1 to H42, but the compound is not limited thereto:

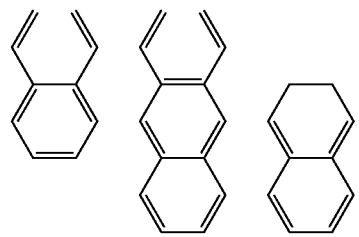

H1

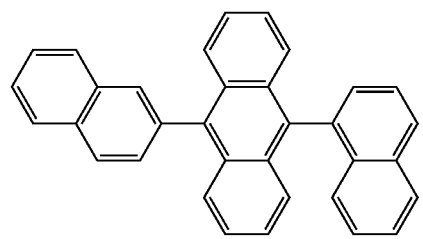

H2

H3
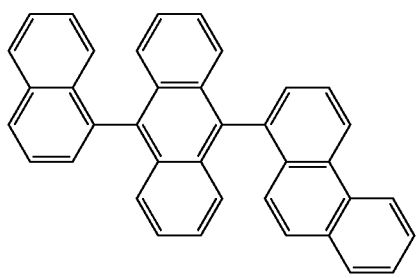
H4
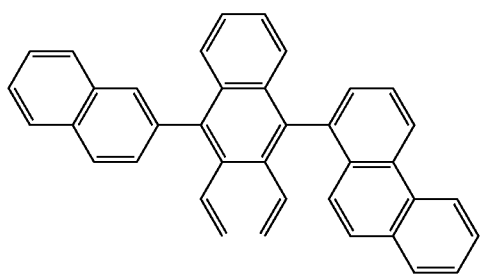
H5
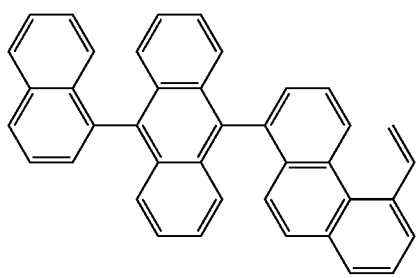
H6
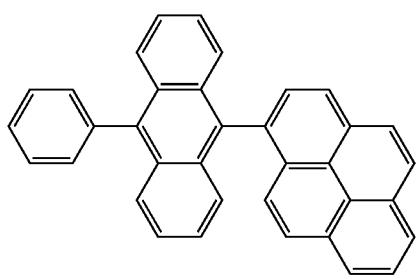
H7
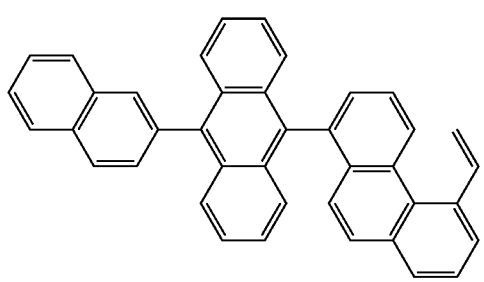
H8
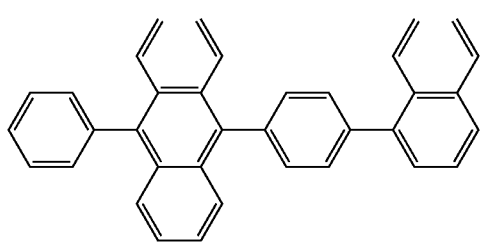
H9
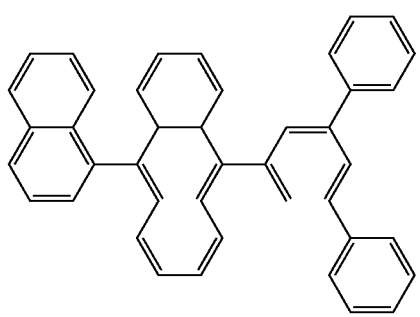
H10
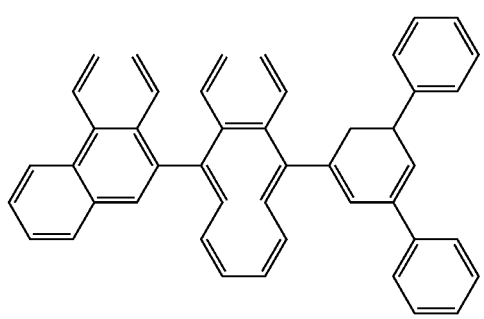
H11
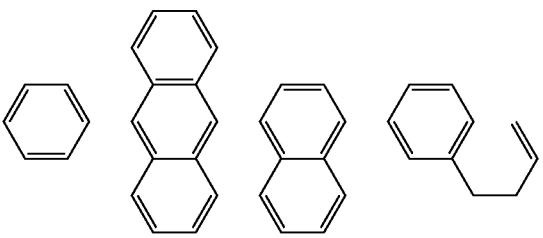
H12
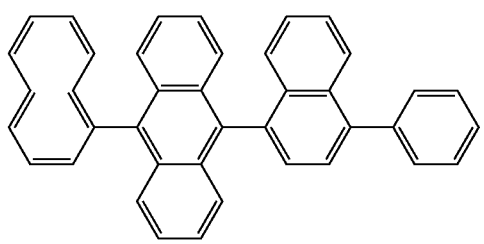
H13
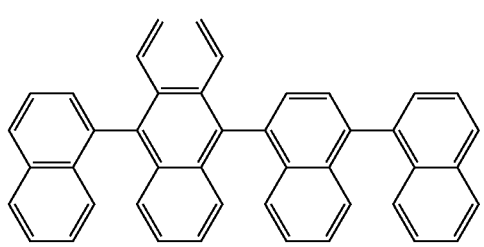

-continued
H14
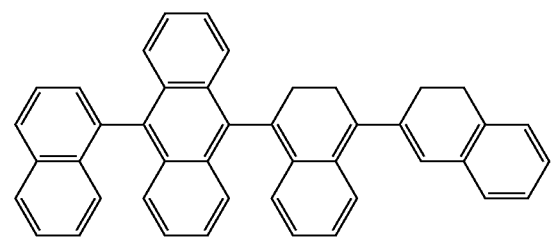
H15
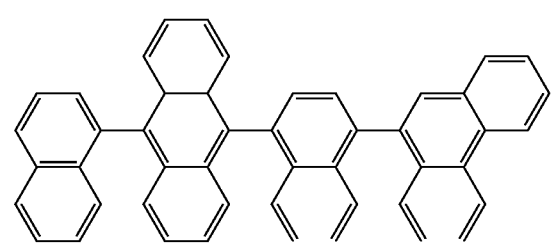
H16
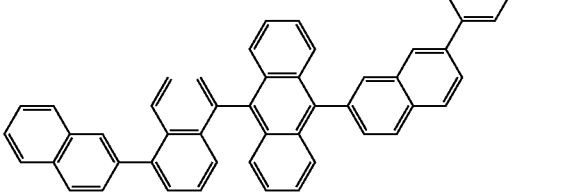
H17
H18
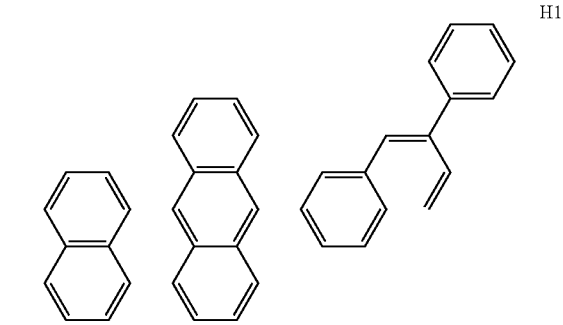
-continued
H19
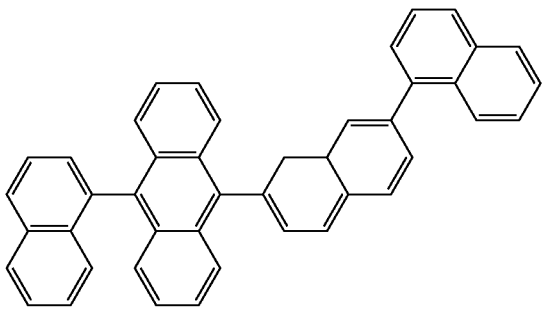
H20
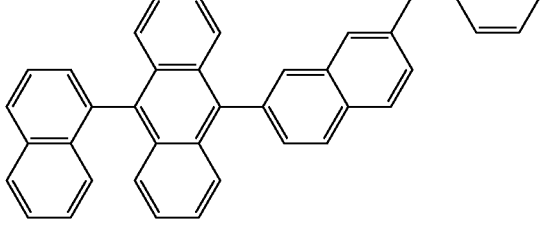
H21
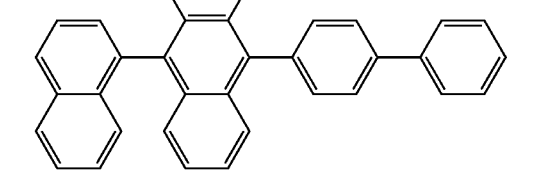
H22
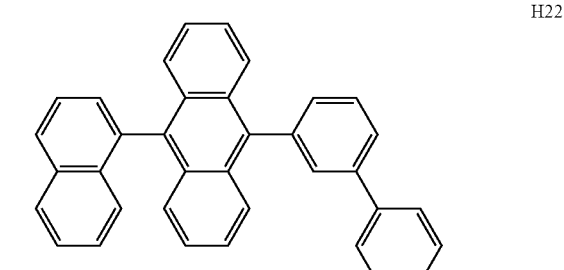
H23

H24
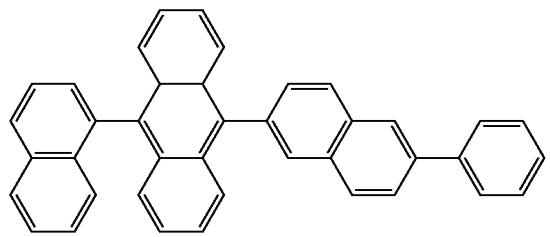
H25
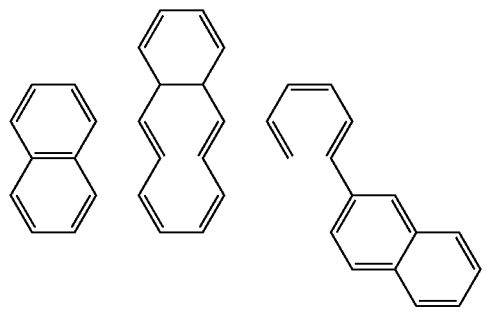
H26
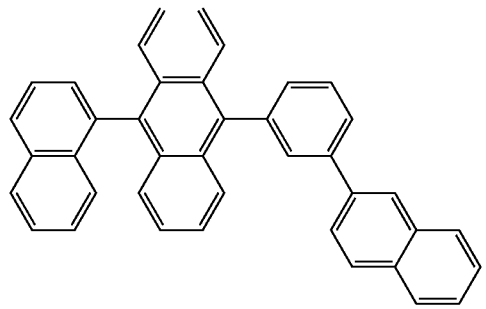
H27
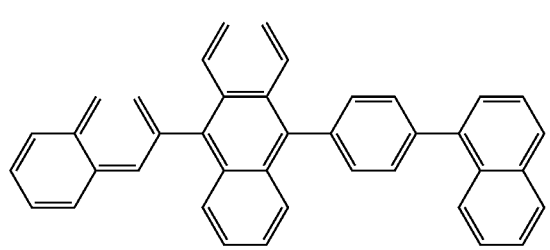
H28
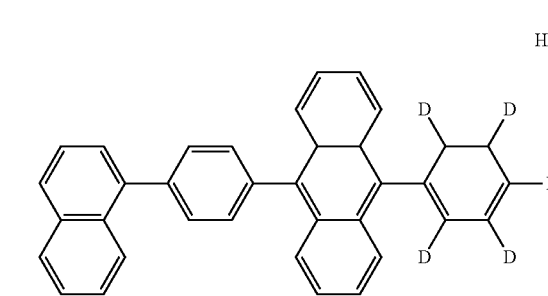
H29
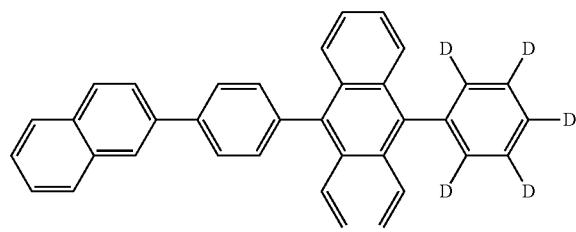
H30
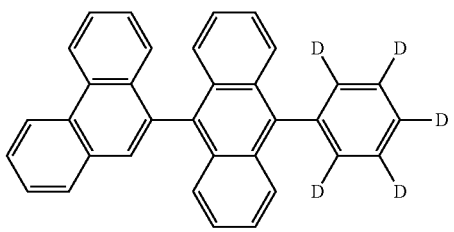
H31
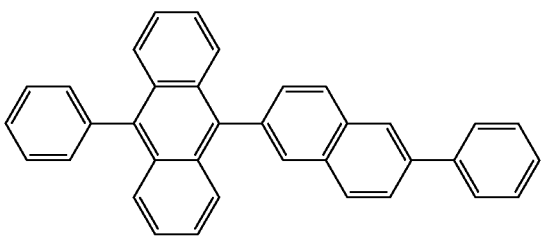
H32
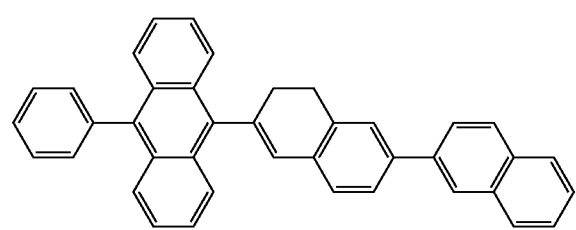
H33
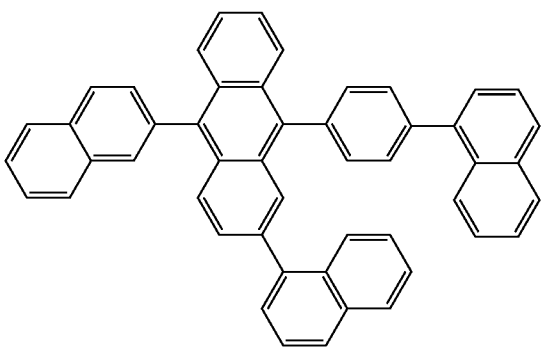

H34
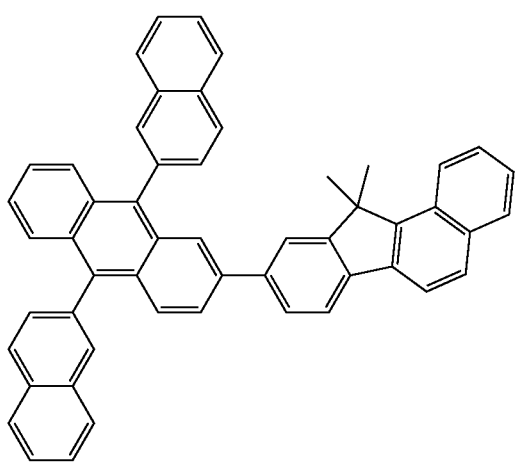
H35
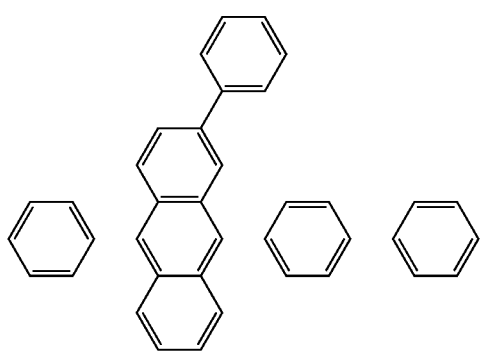
H36
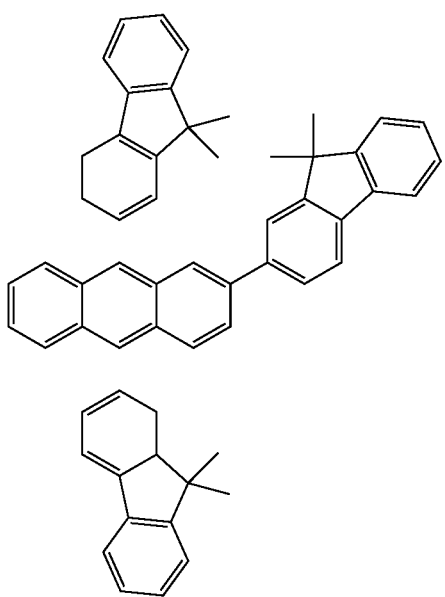
H37
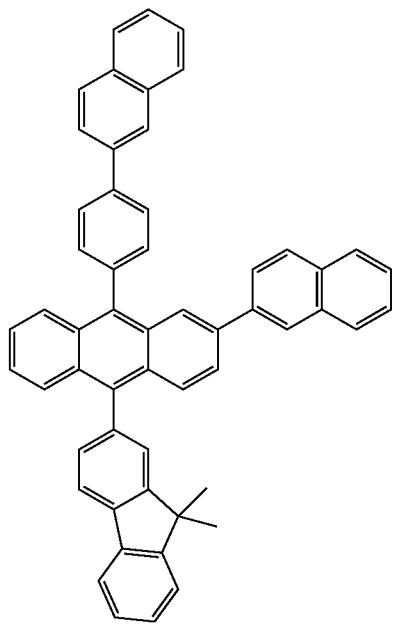
H38
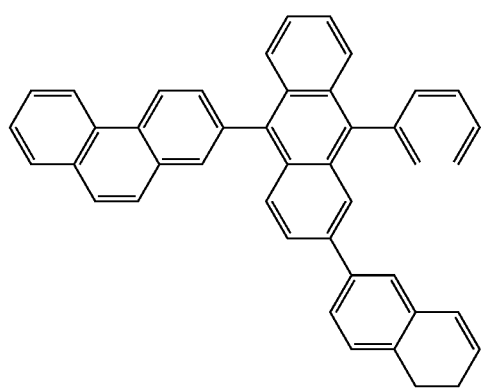
H39
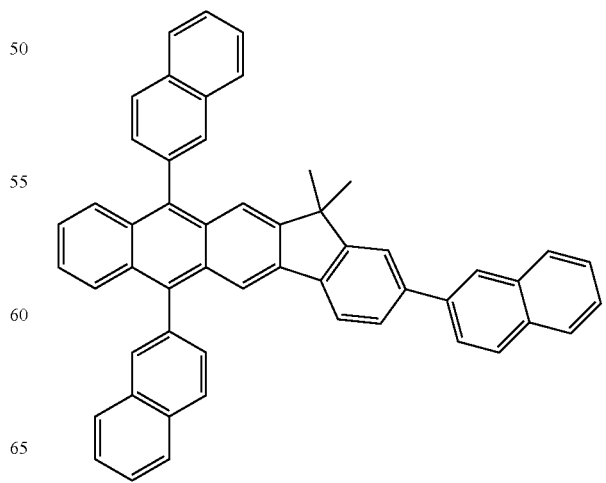

H40
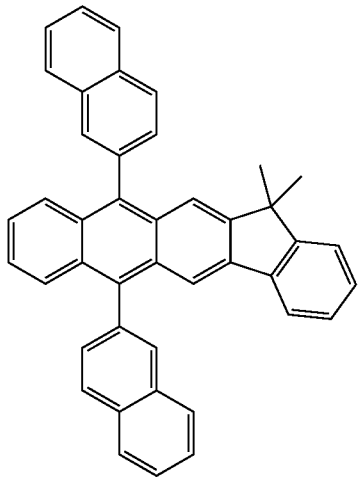
H41
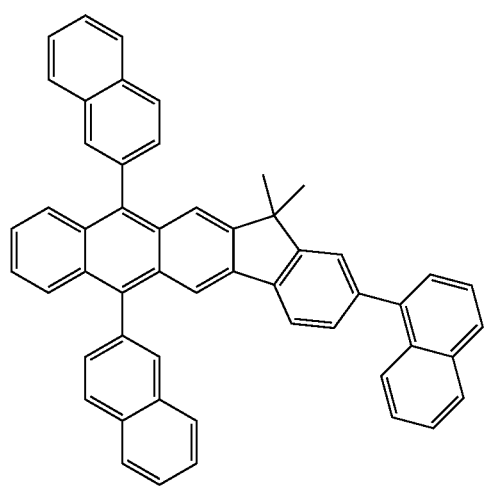
H42
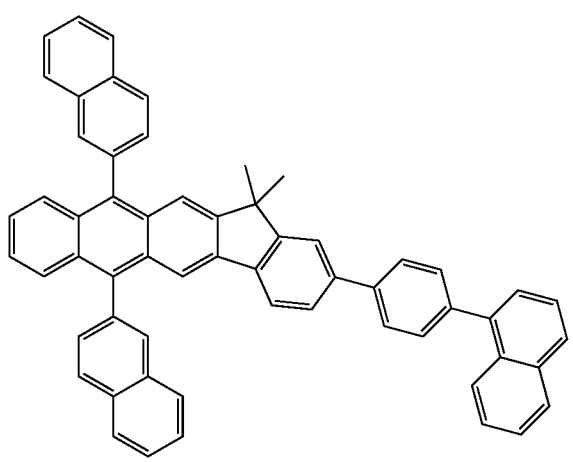
H43
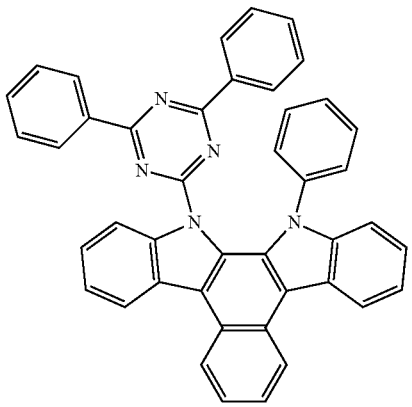
H44
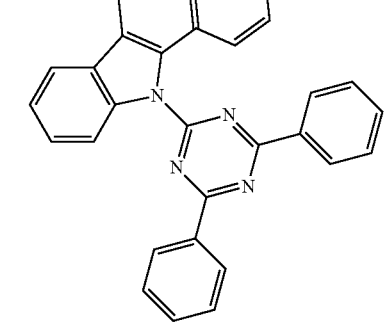
H45
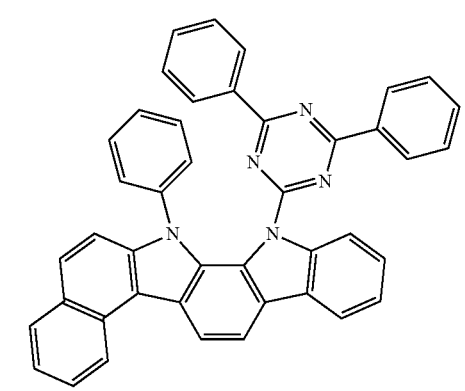
In an implementation, the host may include at least one of Compounds H43 to H49, but the host is not limited thereto:

-continued

H46
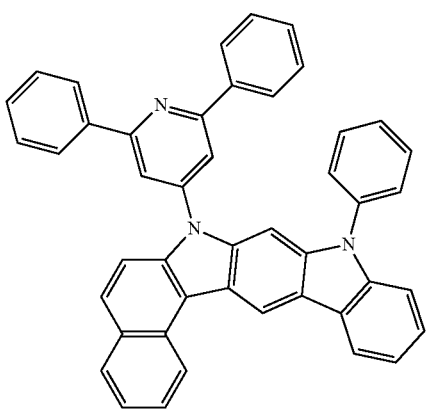

H47
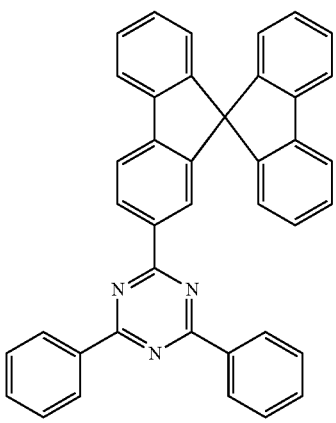

H48
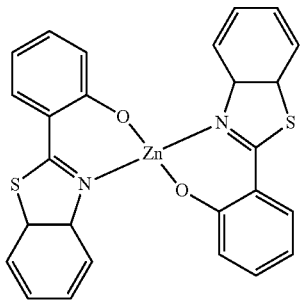

H49
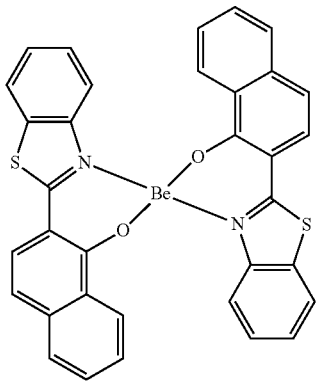

The dopant may include a compound represented by Formula 1. In an implementation, the dopant may further include at least one of a fluorescent dopant and a phosphorescent dopant, in addition to the compound represented by Formula 1.

The phosphorescent dopant may include an organic metal complex represented by Formula 401:

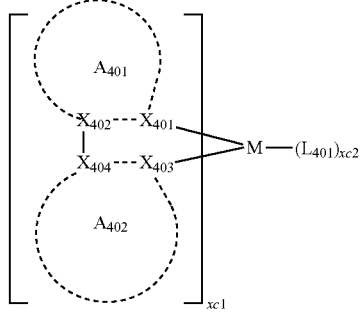

<Formula 401>

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently a nitrogen atom or a carbon atom;

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isooxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzooxazole, substituted isobenzooxazole, substituted triazole, substituted oxadiazole, substituted triazine, substituted dibenzofuran, and substituted dibenzothiophene may be selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a non-aromatic condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic heterocondensed polycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be an integer selected from 1, 2, and 3; and xc2 may be an integer selected from 0, 1, 2, and 3.

$L_{401}$ may be a monovalent, divalent, or trivalent organic ligand. For example, $L_{401}$ may be selected from a halogen ligand (e.g., Cl or F), a diketone ligand (e.g., acetylacetonate, 1,3-diphenyl-1,3-propanedionate, 2,2,6,6-tetramethyl-3,5-heptanedionate, or hexafluoroacetonate), a carboxylic acid ligand (e.g., picolinate, dimethyl-3-pyrazolecarboxylate, or benzoate), a carbon monoxide ligand, an isonitrile ligand, a cyano ligand, and a phosphorus ligand (e.g., phosphine or phosphite), but is not limited thereto.

In Formula 401, when $A_{401}$ has at least two substituents, the at least two substituents of $A_{401}$ may link to each other and form a saturated or unsaturated ring.

In Formula 401, when $A_{402}$ has at least two substituents, the at least two substituents of $A_{402}$ may link to each other and form a saturated or unsaturated ring.

In Formula 401, when xc1 is 2 or greater, a plurality of ligands,

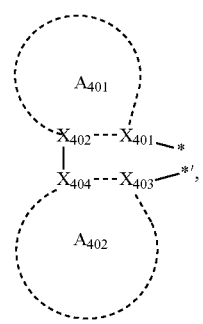

may be identical to or different from each other. In Formula 401, when xc1 is 2 or greater, $A_{401}$ and $A_{402}$ may be linked to each other by directly linking to another neighboring ligand of $A_{401}$ and $A_{402}$ or with a connection group (e.g., a $C_1$-$C_5$ alkylene group, —N(R')— (here, R' is $C_1$-$C_{10}$ alkyl group or a $C_6$-$C_{20}$ aryl group), or —C(=O)—) therebetween.

In an exemplary embodiment, the phosphorescent dopant may be selected from Compounds PD1 to PD74 below, but is not limited thereto:

PD1

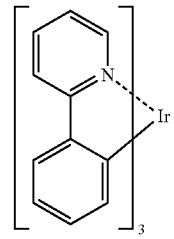

PD2

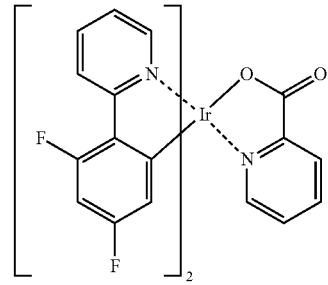

PD3

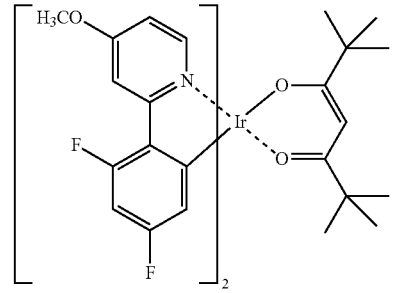

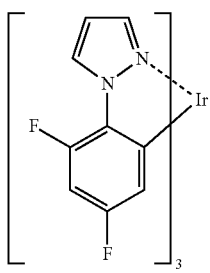
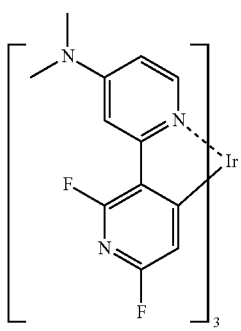
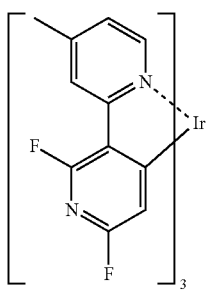
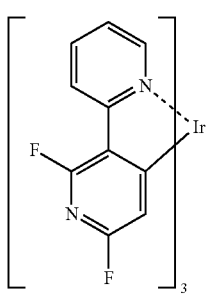
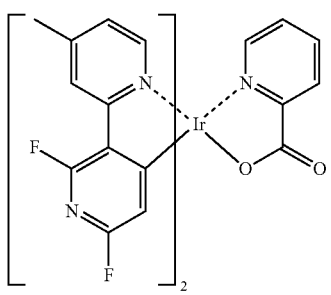
PD4 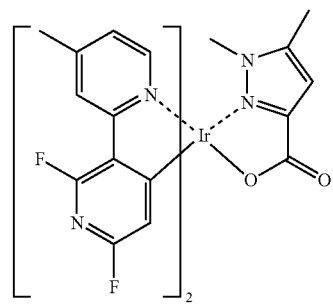
PD5 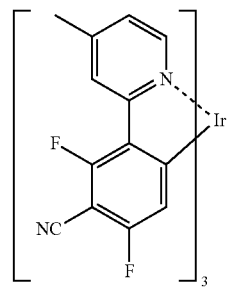
PD6 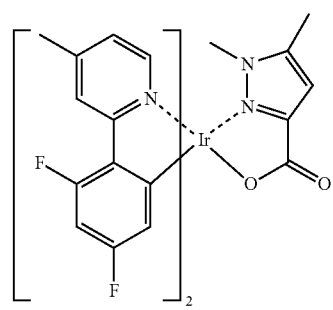
PD7 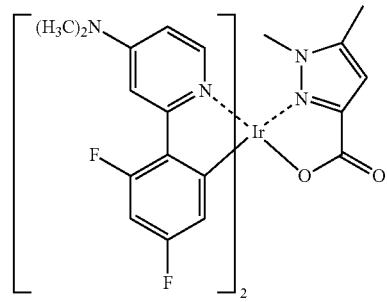
PD8 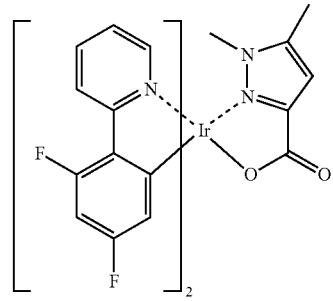
PD9
PD10
PD11
PD12
PD13

PD14 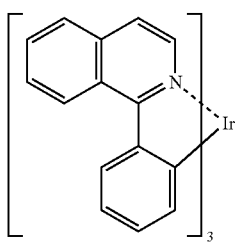
PD15 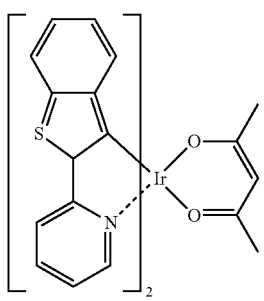
PD16 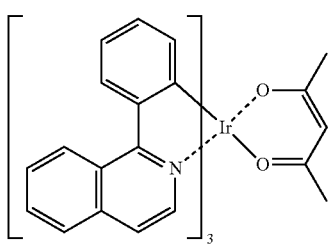
PD17 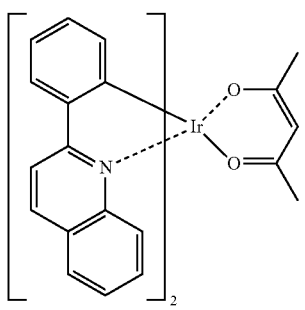
PD18 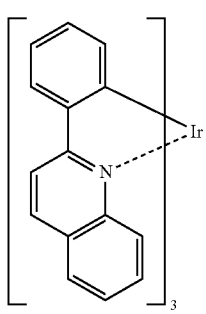
PD19 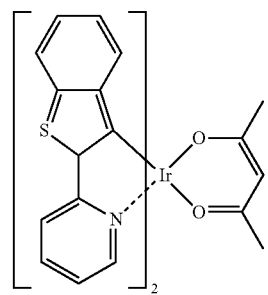
PD20 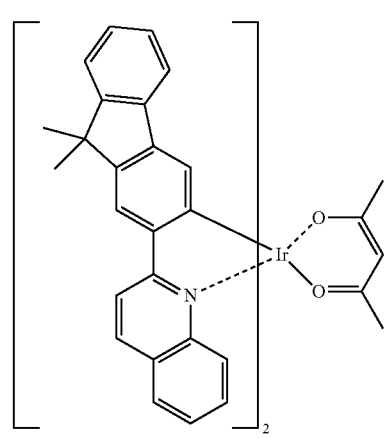
PD21 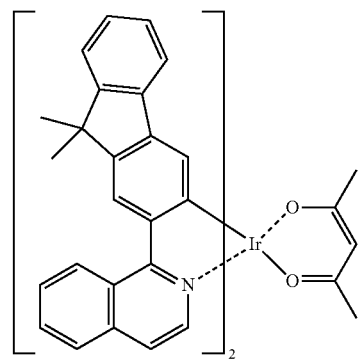
PD22 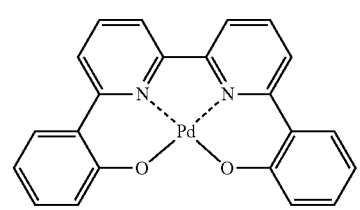
PD23 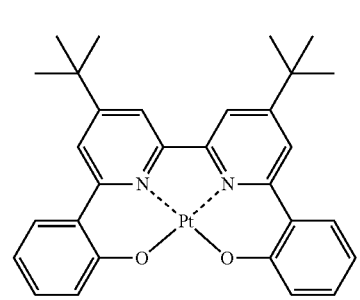

PD24 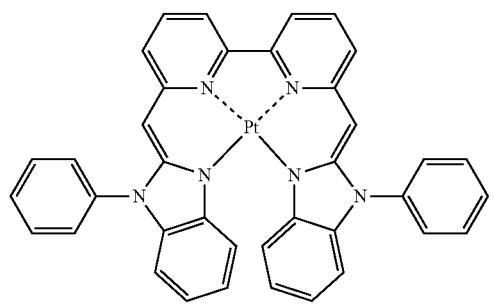
PD25 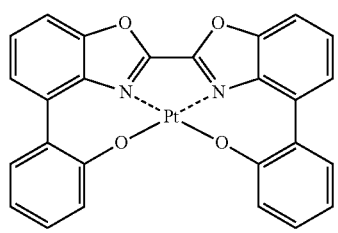
PD26 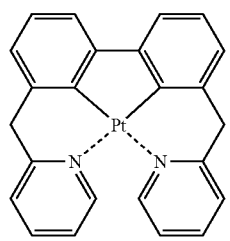
PD27 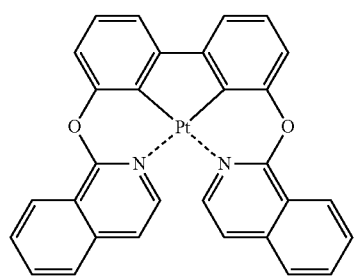
PD28 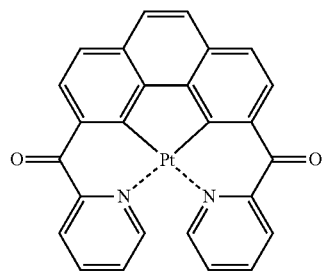
PD29 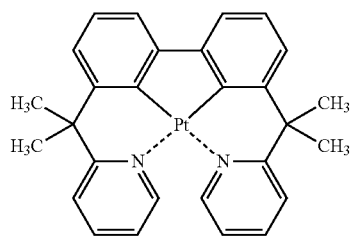
PD30 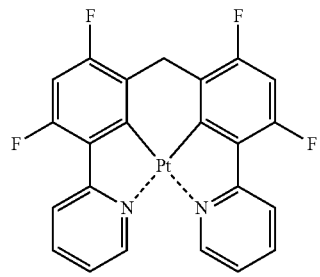
PD31 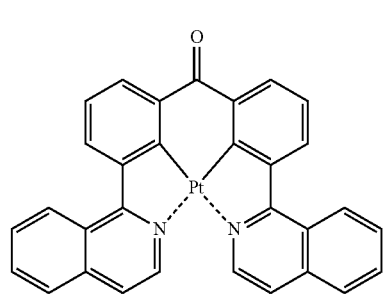
PD32 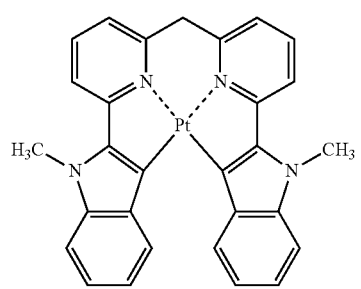
PD33 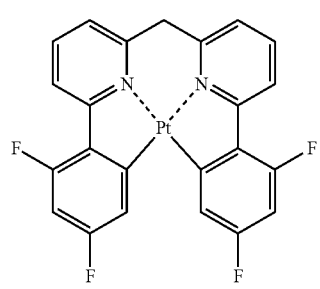
PD34 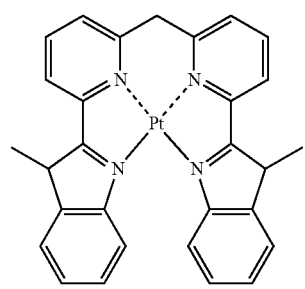

-continued
PD35 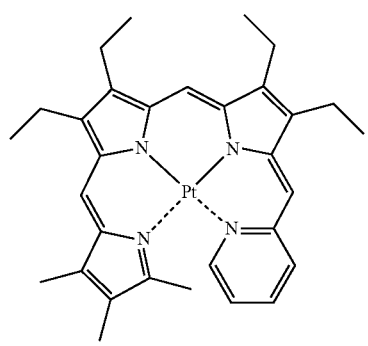
PD36 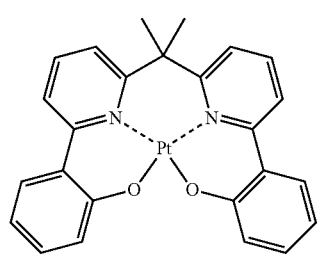
PD37 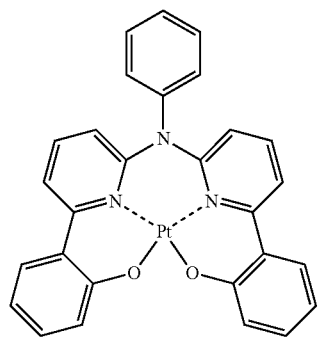
PD38 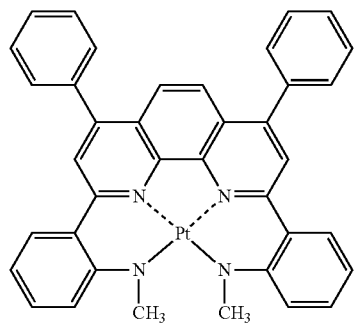
PD39 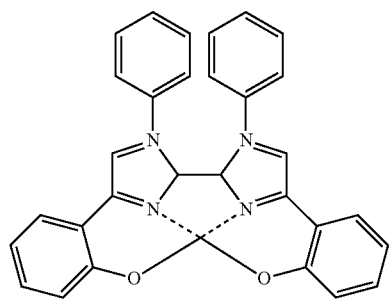
-continued
PD40 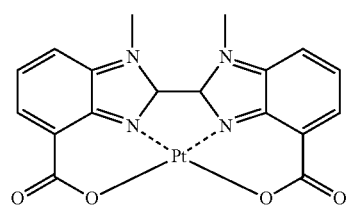
PD41 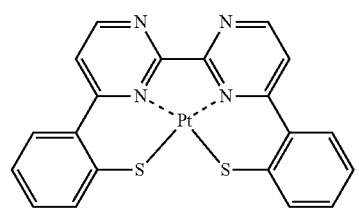
PD42 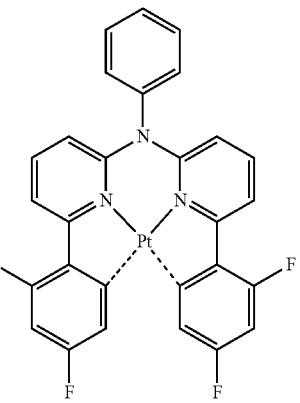
PD43 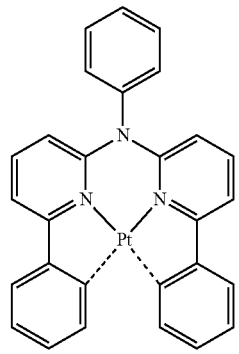
PD44 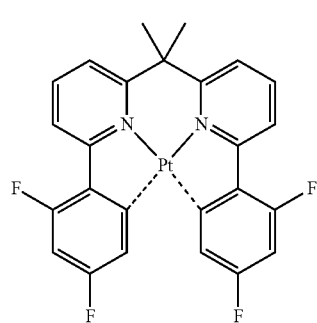

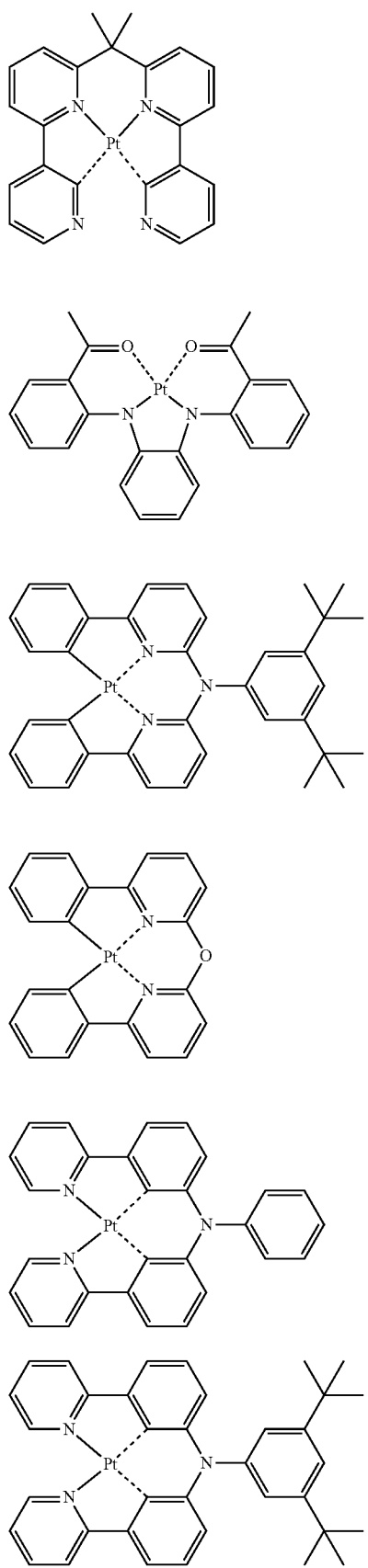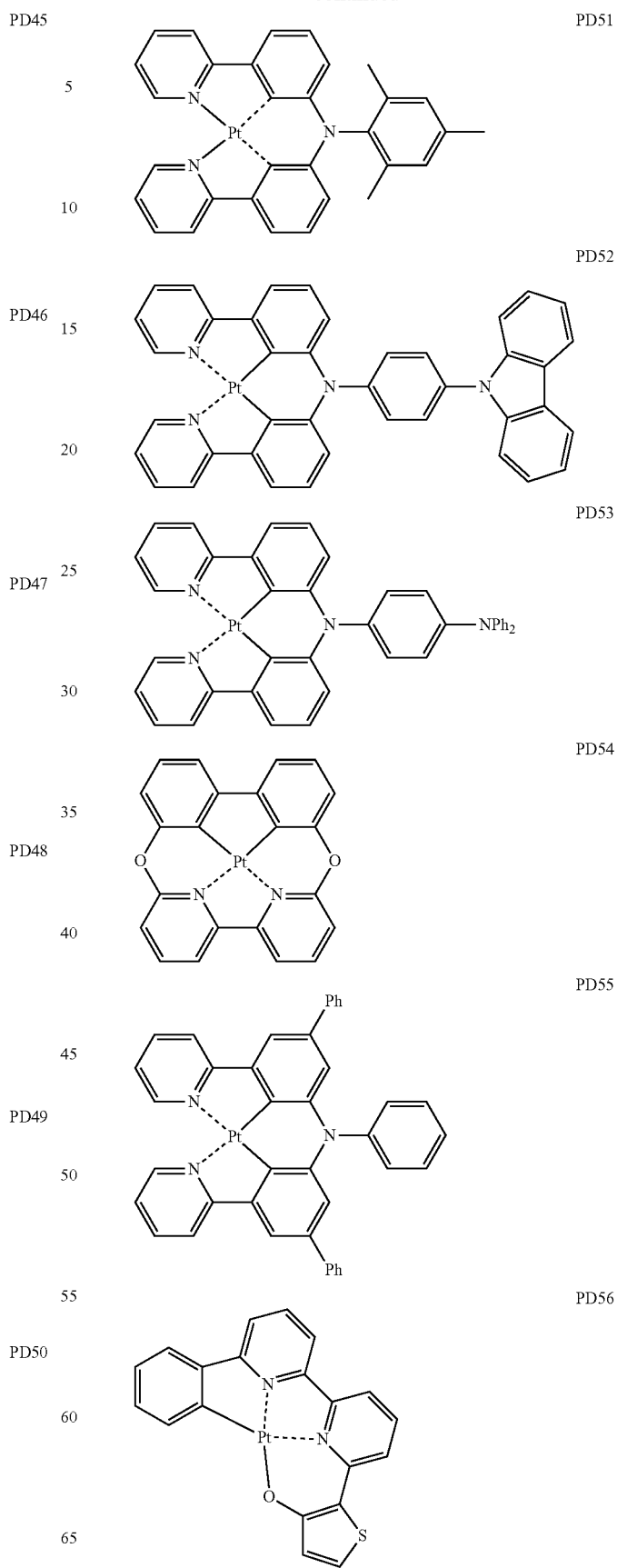

PD57
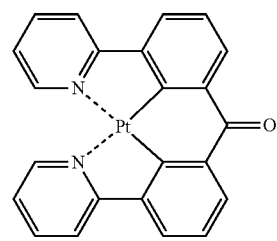
PD58
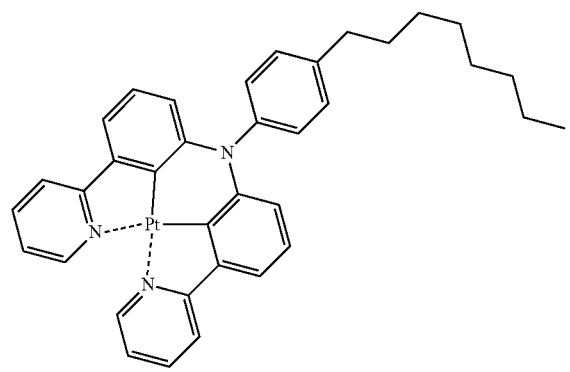
PD59
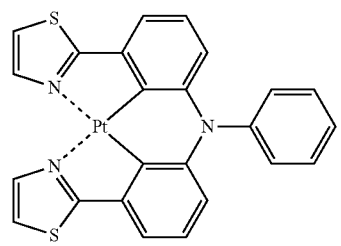
PD60
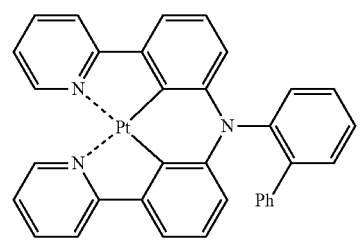
PD61
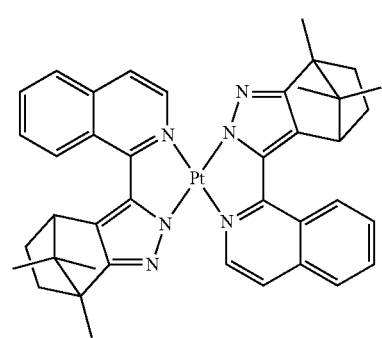
PD62
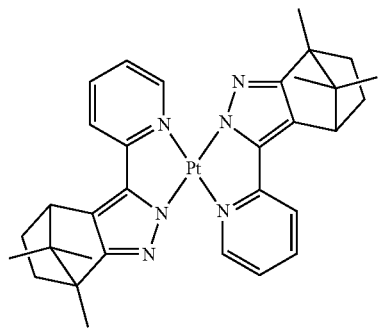
PD63
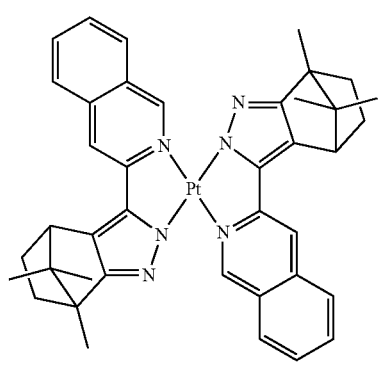
PD64
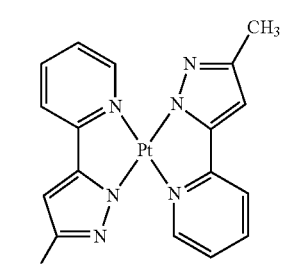
PD65
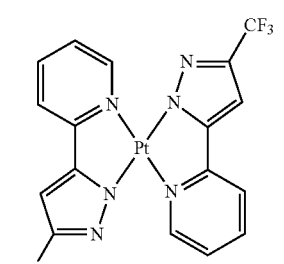
PD66
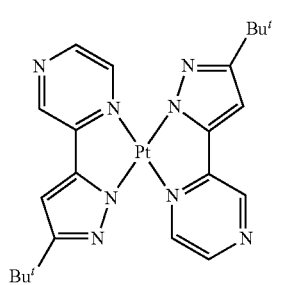

PD67 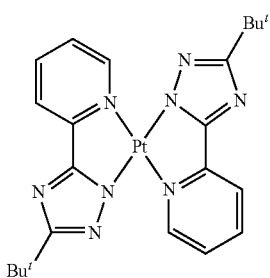
PD68 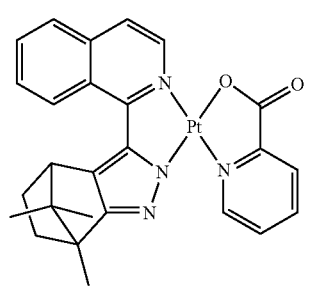
PD69
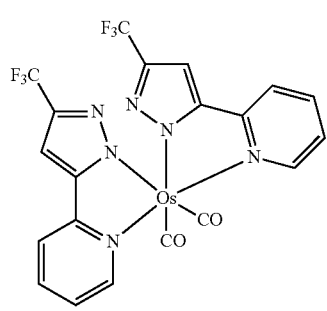
PD70
PD71
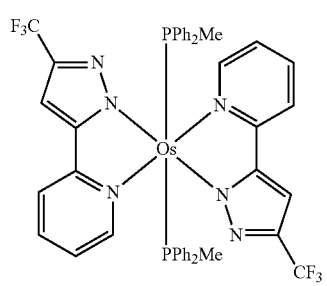
PD72 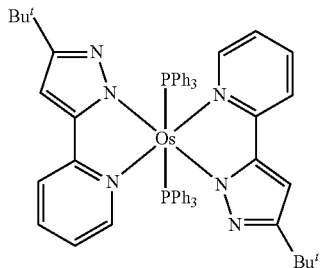
PD73 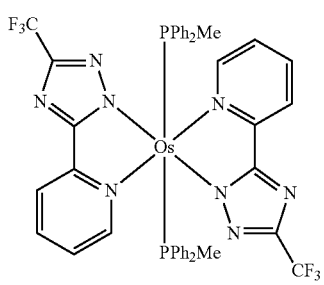
PD74 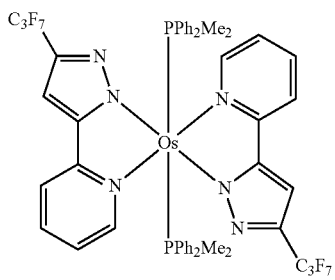
In an implementation, the phosphorescent dopant may include PtOEP below:
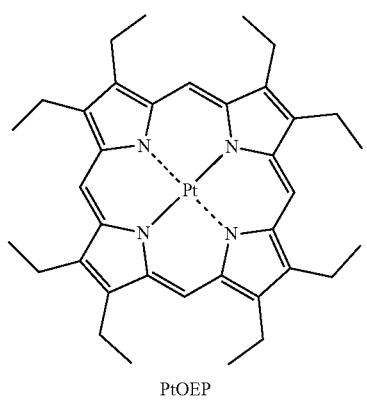
PtOEP
The fluorescent dopant may include at least one of DPAVBi, BDAVBi, TBPe, DCM, DCJTB, Coumarin 6, and C545T below:

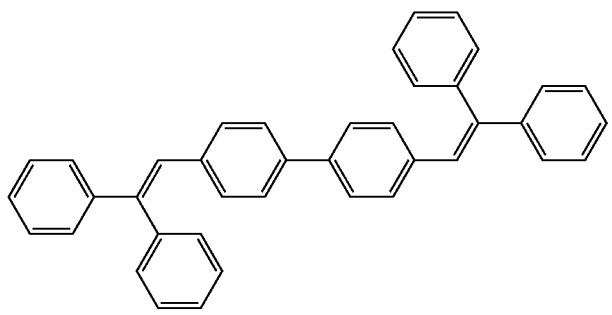

DPVBi

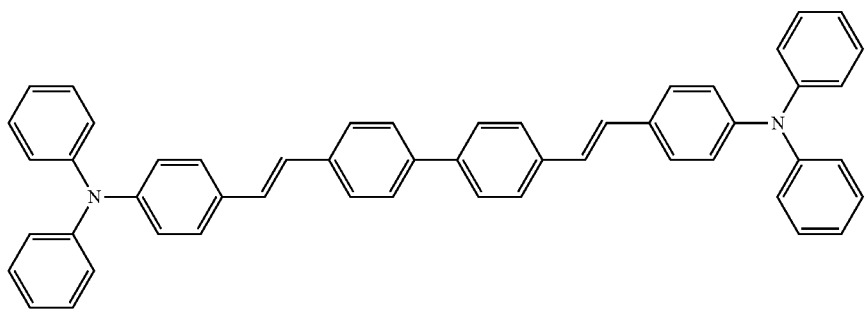

DPAVBi

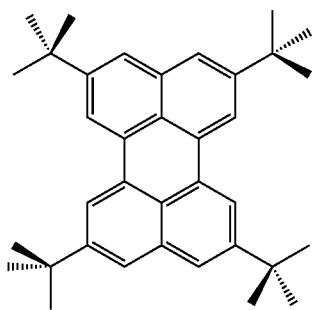

TBPe

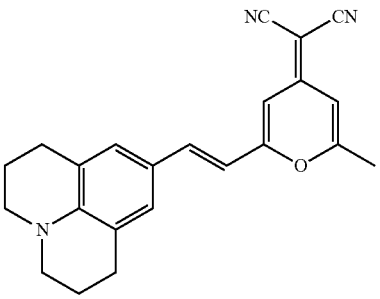

DCM

DCJTB

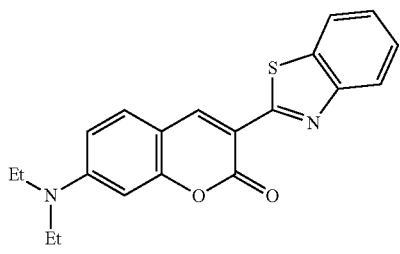

Coumarin

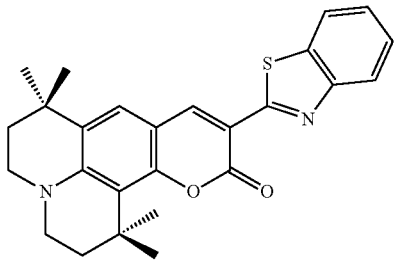

C545T

In an implementation, the fluorescent dopant may include a compound represented by Formula 501 below:

<Formula 501>

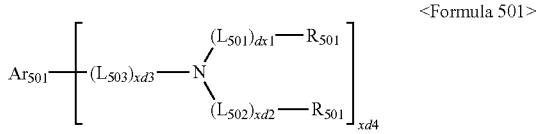

In Formula 501, $Ar_{501}$ may be selected from, a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene group, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, and —Si($Q_{501}$)($Q_{502}$)($Q_{503}$) (here, $Q_{501}$ to $Q_{503}$ are each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

descriptions of $L_{501}$ to $L_{503}$ may be each independently referred to the description of $L_{201}$;

$R_{501}$ and $R_{502}$ may be each independently selected from, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, and a phenyl group;

xd1 to xd3 may be each independently an integer selected from 0, 1, 2, and 3;

xb4 may be an integer selected from 1, 2, 3, and 4.

The fluorescent host may include at least one of Compounds FD1 to FD8:

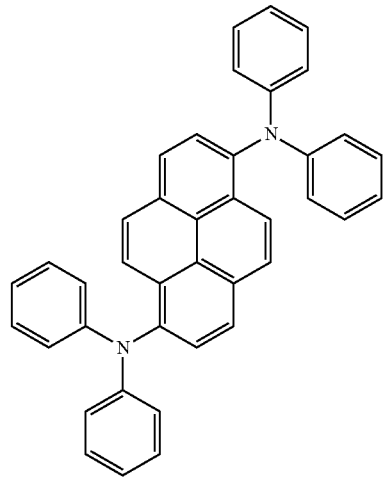

FD1

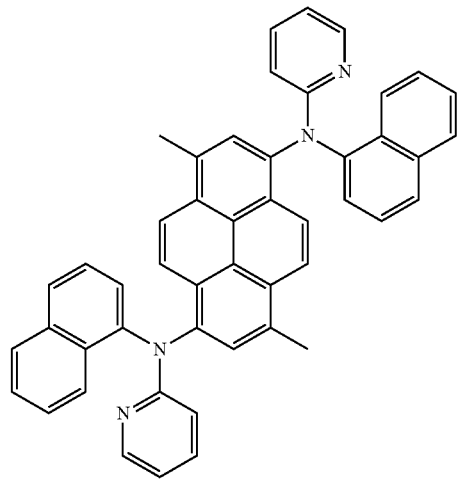

FD2

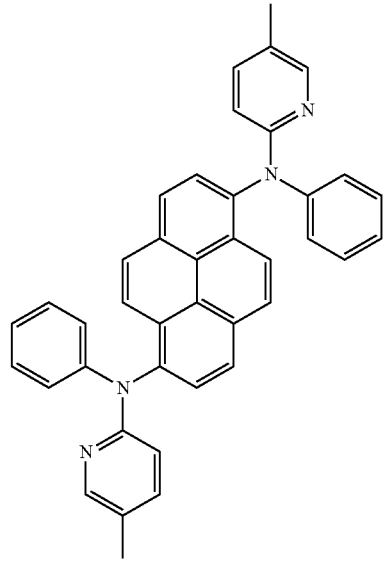

FD3

FD4

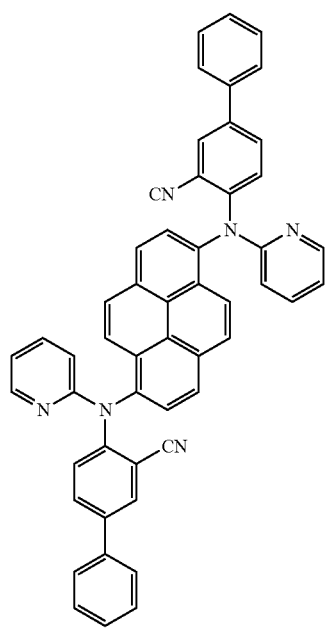

FD7

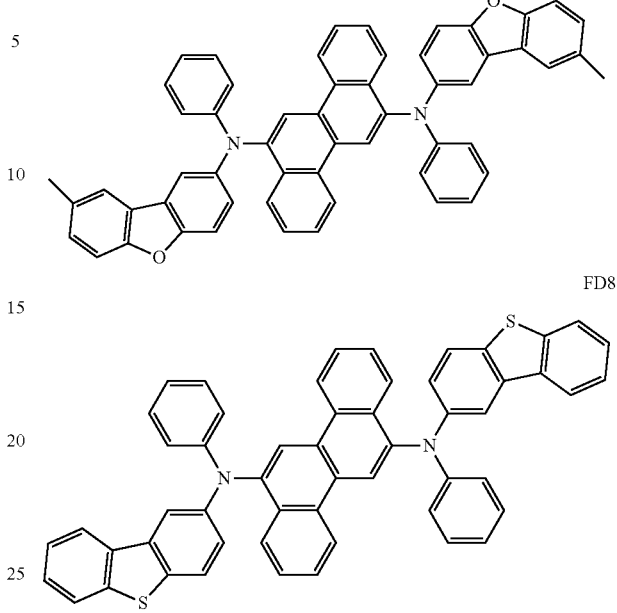

FD8

FD5

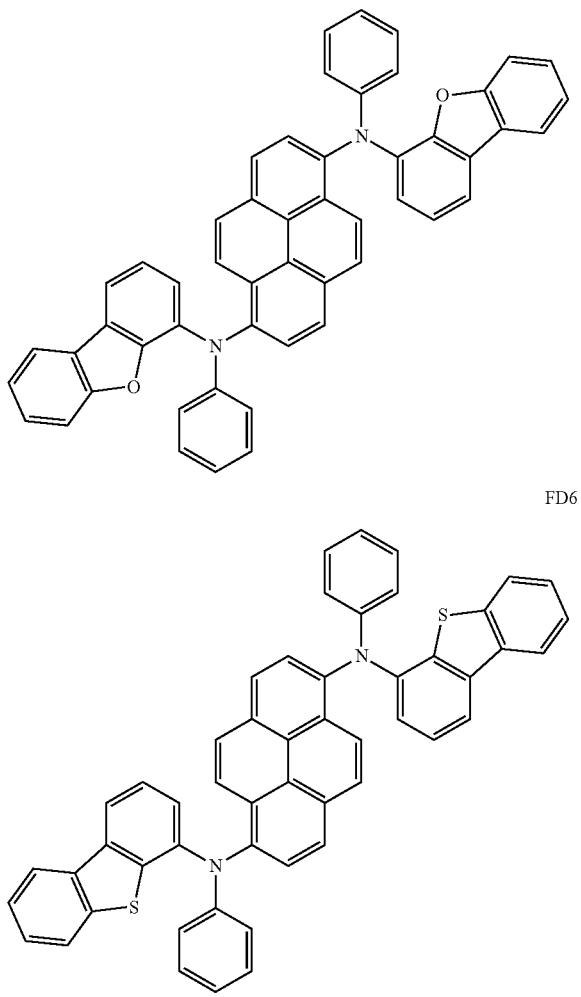

FD6

An amount of the dopant in the EML may be generally within a range of about 0.01 part to about 15 parts by weight, based on 100 parts by weight of a host, but the amount is not limited thereto.

A thickness of the EML may be in a range of about 100 Å to about 1,000 Å, e.g., about 200 Å to about 600 Å. When a thickness of the EML is within this range, light-emitting properties of the organic light-emitting device may be excellent without substantial increase in driving voltage.

Next, an electron transport region may be disposed on the EML.

The electron transport region may include at least one selected from an HBL, an ETL, and an EIL, but is not limited thereto.

For example, the electron transport region may have a structure of ETL/EIL or EBL/ETL/EIL sequentially stacked on the EML, but the structure is not limited thereto.

In an exemplary embodiment, the organic layer 150 of the organic light-emitting device 10 may include an electron transport region disposed between the EML and the second electrode 190.

The electron transport region may include the HBL. When the EML includes a phosphorescent dopant, the HBL may be formed to help prevent triplet excitons or holes from being diffused to the ETL.

When the electron transport region includes the HBL, the HBL may be formed on the EML by using various methods such as vacuum deposition, spin coating, casting, LB deposition, inkjet printing, laser printing, or LITI. When the HBL is formed by methods such as vacuum deposition and spin coating, the deposition conditions and the coating conditions of the HBL may be referred to the de deposition conditions and the coating conditions of the HIL.

The HBL may include, e.g., at least one of BCP and Bphen below, but is not limited thereto:

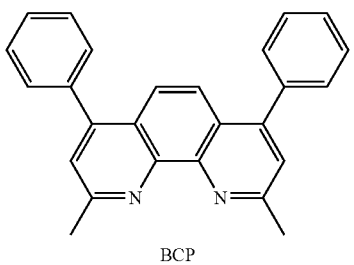

BCP

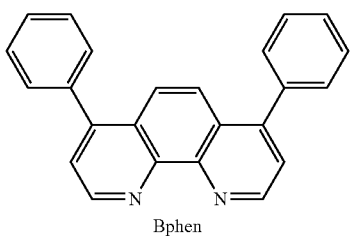

Bphen

A thickness of the HBL may be in a range of about 20 Å to about 1,000 Å, e.g., about 30 Å to about 300 Å. When a thickness of the HBL is within this range, hole blocking properties of the organic light-emitting device may be excellent without substantial increase in driving voltage.

The electron transport region may include the ETL. The ETL may be formed on the EML or the HBL by using various methods such as vacuum deposition, spin coating, casting, LB deposition, inkjet printing, laser printing, or LITI. When the ETL is formed by methods such as vacuum deposition and spin coating, the deposition conditions and the coating conditions of the ETL may be referred to the deposition conditions and the coating conditions of the HIL.

In an exemplary embodiment, the organic layer 150 of the organic light-emitting device 10 may include an electron transport region between the EML and the second electrode 190. The electron transport region may include the ETL.

The ETL may include at least one selected from BCP and Bphen above and $Alq_a$, Balq, TAZ, and NTAZ below:

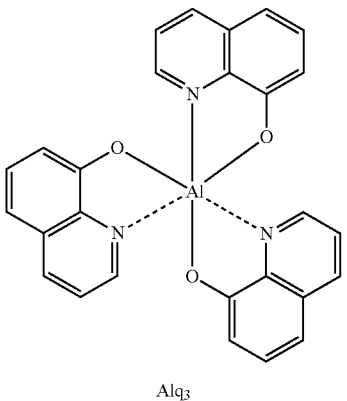

Alq$_3$

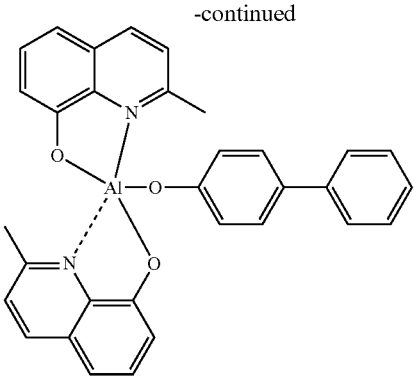

BAlq

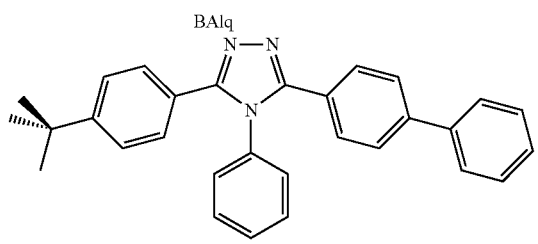

TAZ

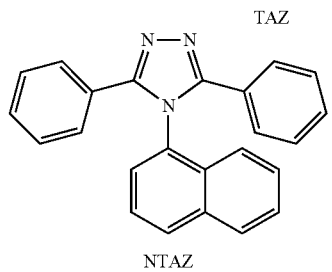

NTAZ

A thickness of the ETL may be in a range of about 100 Å to about 1,000 Å, e.g., about 150 Å to about 500 Å. When a thickness of the ETL is within this range, electron transporting properties of the organic light-emitting device may be excellent without substantial increase in driving voltage.

The ETL may further include a metal-containing material in addition to the materials above.

The metal-containing material may include a Li-complex. The Li-complex may include, for example, compound ET-D1 (lithium quinolate (LiQ)) or ET-D2:

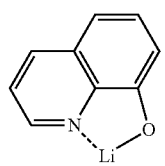

ET-D1

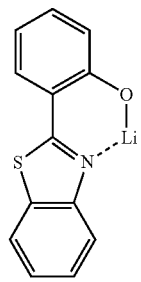

ET-D2

The electron transport region may include the EIL that facilitates injection of electrons from the second electrode 190.

The EIL may be formed on the ETL by using various methods such as vacuum deposition, spin coating, casting, LB deposition, inkjet printing, laser printing, or LITI. When the EIL is formed by vacuum deposition and spin coating, the deposition conditions and the coating conditions of the EIL may be referred to the de deposition conditions and the coating conditions of the HIL.

The EIL may include at least one selected from LiF, NaCl, CsF, $Li_2O$, BaO, and LiQ.

A thickness of the EIL may be in a range of about 1 Å to about 100 Å, e.g., about 3 Å to about 90 Å. When a thickness of the EIL is within this range, electron injecting properties of the organic light-emitting device may be excellent without substantial increase in driving voltage.

The second electrode 190 may be disposed on the organic layer 150. The second electrode 190 may be a cathode, which is an electron injection electrode. In this regard, a material for forming the second electrode 190 may include a metal, an alloy, an electric conducting compound, and a mixture thereof having a low work function. For example, the second electrode 190 may be a thin film formed of lithium (Li), magnesium (Mg), aluminum (Al), aluminum-lithium (Al—Li), calcium (Ca), magnesium-indium (Mg—In), or magnesium-silver (Mg—Ag). Also, ITO or IZO may be used as a material for forming the second electrode 190. The second electrode 190 may be a reflective electrode, a semitransparent electrode, or a transparent electrode.

In an implementation, an organic layer of an organic light-emitting device according to an embodiment may be formed by using a deposition method using a compound according to an embodiment or by using a wet method, in which the organic light-emitting device is coated with the compound that is prepared as a solution.

An organic light-emitting device according to an embodiment may be included in various types of flat panel displays, e.g., a passive matrix organic light-emitting display apparatus and an active matrix organic light-emitting display apparatus. For example, when the organic light-emitting device is included in an active matrix organic light-emitting display apparatus, a first electrode located on a side of a substrate is a pixel electrode which may be electrically connected to a source electrode or a drain electrode of a thin film transistor. In an implementation, the organic light-emitting device may be included in a flat panel display that may display images on both surfaces.

The organic light-emitting device has been described with reference to the FIGURE, but an organic light-emitting device is not limited thereto.

Hereinafter, representative substituents among the substituents in the present specification are defined as follows (the number of carbons defining a substituent is not limited and does not particularly limit characteristics of the substituent, and definition of a substituent not defined in the present specification follows general definition thereof).

As used herein, a $C_1$-$C_{60}$ alkyl group denotes a monovalent linear or branched aliphatic hydrocarbon group, and examples of the $C_1$-$C_{60}$ alkyl group include a methyl group, an ethyl group, a propyl group, an isobutyl group, a sec-butyl group, a tert-butyl group, a pentyl group, an iso-amyl group, and a hexyl group. As used herein, examples of a $C_1$-$C_{60}$ alkylene group include a divalent group that has the same structure as the $C_1$-$C_{60}$ alkyl group.

As used herein, a $C_1$-$C_{60}$ alkoxy group denotes a monovalent group having a formula of $—OA_{101}$ (here, $A_{101}$ is the $C_1$-$C_{60}$ alkyl group), and examples of the $C_1$-$C_{60}$ alkoxy group include a methoxy group, an ethoxy group, and an isopropyloxy group.

As used herein, a $C_2$-$C_{60}$ alkenyl group has a structure including at least one carbon-carbon double bond in the middle or at an end of the $C_2$-$C_{60}$ alkyl group, and examples of the $C_2$-$C_{60}$ alkenyl group include an ethenyl group, a propenyl group, and a butenyl group. As used herein, a $C_2$-$C_{60}$ alkenylene group denotes a divalent group that has the same structure as the $C_2$-$C_{60}$ alkenyl group.

As used herein, a $C_2$-$C_{60}$ alkynyl group has a structure including at least one carbon-carbon triple bond in the middle or at an end of the $C_2$-$C_{60}$ alkyl group, and examples of the $C_2$-$C_{60}$ alkynyl group include an ethynyl group and a propynyl group. As used herein, a $C_2$-$C_{60}$ alkynylene group denotes a divalent group that has the same structure as the $C_2$-$C_{60}$ alkynyl group.

As used herein, a $C_3$-$C_{10}$ cycloalkyl group denotes a $C_3$-$C_{10}$ monovalent saturated hydrocarbon monocyclic group, and examples of the $C_3$-$C_{10}$ cycloalkyl group include a cyclopropyl group, a cyclobutyl group, a cyclopentyl group, a cyclohexyl group, and a cycloheptyl group. As used herein, a $C_3$-$C_{10}$ cycloalkylene group denotes a divalent group that has the same structure as the $C_3$-$C_{10}$ cycloalkyl group.

As used herein, the $C_2$-$C_{10}$ heterocycloalkyl group denotes a $C_2$-$C_{10}$ monovalent monocyclic group including at least one hetero atom selected from N, O, P, and S as a ring-forming atom, and examples of the $C_2$-$C_{10}$ heterocycloalkyl group include a tetrahydrofuranyl group and a tetrahydrothiophenyl group. As used herein, a $C_2$-$C_{10}$ heterocycloalkylene group denotes a divalent group that has the same structure as the $C_2$-$C_{10}$ heterocycloalkyl group.

As used herein, a $C_3$-$C_{10}$ cycloalkenyl group denotes a $C_3$-$C_{10}$ monovalent monocyclic group having at least one double bond in the ring while not losing its aromacity, and examples of the $C_3$-$C_{10}$ cycloalkenyl group include a cyclopentyl group, a cyclohexenyl group, and a cycloheptenyl group. As used herein, the $C_3$-$C_{10}$ cycloalkenylene group denotes a divalent group that has the same structure as the $C_3$-$C_{10}$ cycloalkenyl group.

As used herein, a $C_2$-$C_{10}$ heterocycloalkenyl group denotes a $C_2$-$C_{10}$ monovalent monocyclic group including at least one hetero atom selected from N, O, P, and S as a ring-forming atom and at least one double bond in the ring, and examples of the $C_2$-$C_{10}$ heterocycloalkenyl group include a 2,3-hydrofuranyl group and a 2,3-hydrothiophenyl group. As used herein, a $C_2$-$C_{10}$ heterocycloalkenylene group denotes a divalent group that has the same structure as the $C_2$-$C_{10}$ heterocycloalkenyl group.

As used herein, a $C_6$-$C_{60}$ aryl group denotes a monovalent group having a $C_6$-$C_{60}$ carbocyclic aromatic system, and a $C_6$-$C_{60}$ arylene group denotes a divalent group that has a $C_6$-$C_{60}$ carbocyclic aromatic system. Examples of the $C_6$-$C_{60}$ aryl group include a phenyl group, a naphthyl group, an anthracenyl group, a phenanthrenyl group, a pyrenyl group, and a chrysenyl group. As used herein, when the $C_6$-$C_{60}$ aryl group and the $C_6$-$C_{60}$ arylene group include at least two rings, the rings may be fused to each other.

As used herein, a $C_2$-$C_{60}$ heteroaryl group denotes a monovalent group including at least one heteroatom selected from N, O, P, and S as a ring-forming atom and having a $C_2$-$C_{60}$ carbocyclic aromatic system, and a $C_1$-$C_{60}$ heteroarylene group denotes a divalent group including at least one heteroatom selected from N, O, P, and S as a ring-forming atom and having a $C_2$-$C_{60}$ carbocyclic aromatic system. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and a $C_2$-$C_{60}$ heteroarylene group include at least two rings, the rings may be fused to each other.

As used herein, a $C_6$-$C_{60}$ aryloxy group denotes —$OA_{102}$ (here, $A_{102}$ is the $C_6$-$C_{60}$ aryl group), and a $C_6$-$C_{60}$ arylthio group denotes —$SA_{103}$ (here, $A_{103}$ is the $C_6$-$C_{60}$ aryl group).

As used herein, a monovalent non-aromatic condensed polycyclic group denotes a monovalent group having at least two rings that are condensed to each other, including only carbon as a ring-forming atom (e.g., the number of the included carbon atoms may be 8 to 60), and having non-aromaticity, as a whole molecule. Examples of the non-aromatic condensed polycyclic group include a fluorenyl group. As used herein, a divalent non-aromatic condensed polycyclic group denotes a divalent group that has the same structure as the monovalent non-aromatic condensed polycyclic group.

As used herein, a monovalent non-aromatic heterocondensed polycyclic group denotes a monovalent group having at least two rings that are condensed to each other, including a heteroatom selected from N, O, P, and S in addition to carbon as a ring-forming atom (e.g., the number of the included carbon atoms included may be 2 to 60), and having a non-aromacity as a whole molecule. Examples of the non-aromatic heterocondensed polycyclic group include a carbazolyl group. As used herein, a divalent non-aromatic heterocondensed polycyclic group denotes a divalent group that has the same structure as the monovalent non-aromatic heterocondensed polycyclic group.

As used herein, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic heterocondensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic heterocondensed polycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy, a $C_6$-$C_{60}$ arylthio, a $C_2$-$C_{60}$ heteroaryl group, a monovalent non-aromatic condensed polycyclic group, a monovalent non-aromatic heterocondensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy, a $C_6$-$C_{60}$ arylthio, a $C_2$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy, a $C_6$-$C_{60}$ arylthio, a $C_2$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy, a $C_6$-$C_{60}$ arylthio, a $C_2$-$C_{60}$ heteroaryl group, a monovalent non-aromatic condensed polycyclic group, a monovalent non-aromatic heterocondensed polycyclic group, $N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

$Q_1$ to $Q_7$, $Q_{11}$ to $Q_{17}$, $Q_{21}$ to $Q_{27}$, and $Q_{31}$ to $Q_{37}$ are, each independently, selected from a hydrogen, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic heterocondensed polycyclic group.

For example, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic heterocondensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic heterocondensed polycyclic group is selected from, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cycloheptenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cycloheptenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cycloheptenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

$Q_1$ to $Q_7$, $Q_{11}$ to $Q_{17}$, $Q_{21}$ to $Q_{27}$, and $Q_{31}$ to $Q_{37}$ are, each independently, selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cycloheptenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The term "Ph" used herein refers to a phenyl group, the term "Me" used herein refers to a methyl group, the term "Et" used herein refers to an ethyl group, and the term "ter-Bu" or "But" used herein refers to a tert-butyl group.

Hereinafter, an OLED according to an embodiment will now be described in more detail with reference to the following examples. In the examples, the expression "B was used instead of A" indicates that an amount per mol of A and an amount per mol of B are the same.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLE

Synthesis Example 1: Synthesis of Compound 23

Synthesis of Compound 23-1

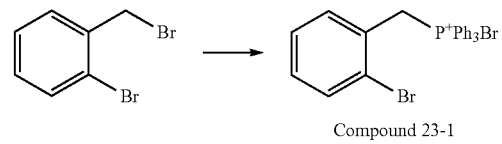

Compound 23-1

10 g of 2-bromobenzyl bromide (40 mmol) and 12.58 g of triphenylphosphine (48 mmol) were mixed with 500 ml of toluene, a solvent, to prepare a solution, and then the solution was heated and stirred for 3 hours. When the reaction was completed, the solution was cooled to room or ambient temperature, and then its precipitate was filtered by using hexane to obtain 19.6 g of Compound 23-1 ((2-bromobenzyl) triphenyl phosphonium bromide) as a white solid (yield: 96.1%).

1H NMR (300 MHz, CDCl3): δ (ppm) 7.8~37.21 (m, 16H), 7.38 (d, J=7.8 Hz, 1H), 7.17 (m, 2H), 5.74 (d, J=14.4 Hz, 2H)

Molecular weight: 431.0559 (theoretical value of C25H21BrP+)

LR-Mass (EI+): 431.0, HR-Mass (FAB+): 431.0564

Synthesis of Compound 23-2

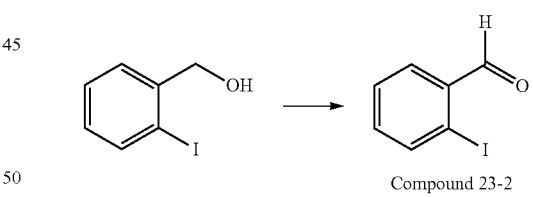

Compound 23-2

10 g of 2-iodobenzylalcohol (42.73 mmol) was mixed with 200 mL of dichloromethane to prepare a solution, 10.13 g of pyridium chlorochromate (47 mmol) was added thereto, and the solution was stirred at ambient temperature. When the reaction was completed, the solvent was removed, and the resultant was purified by using a column chromatography (eluent, ethyl acetate:hexane=1:8) to obtain 9.1 g of Compound 23-2 (2-iodobenzaldehyde) as a yellow liquid (yield: 92%).

1H NMR (300 MHz, CDCl3): δ (ppm) 10.09 (s, 1H), 7.94 (dd, J=15.0, 7.2 Hz, 2H), 7.48 (s, 1H), 7.30 (s, 1H)

Molecular weight: 231.9385 (theoretical value of C7H5IO)

LR-Mass (EI+): 232.0, HR-Mass (EI+): 231.9393

Synthesis of Compound 23-3

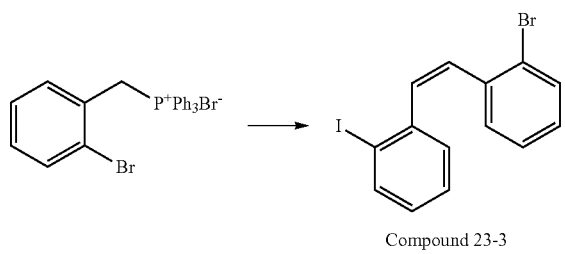

Compound 23-3

33 g of Compound 23-1 (2-bromobenzyl)triphenylphosphonium bromide) (64.425 mmol) and 350 mL of tetrahydrofuran were stirred under a nitrogen atmosphere at a temperature of 0° C. Then, a mixture prepared by mixing 8.434 g of potassium tert-butoxide (75.163 mmol) and 50 mL of tetrahydrofuran was added thereto, a mixture of 12.457 g of Compound 23-2 (2-iodobenzaldehyde) (53.688 mmol) and 100 mL of tetrahydrofuran was dropwisely added thereto, a temperature of the solution was slowly changed to ambient temperature, and the solution was stirred for 24 hours. When the reaction was completed, 100 mL of $H_2O$ was added, stirred, and then an organic layer was separated therefrom by using a large amount of diethyl ether and $H_2O$. Then, the resultant was washed with a saturated sodium chloride solution, and sodium sulfate was used to remove water therefrom. The solvent was removed from the resultant thus obtained, and column chromatography was performed under a hexane condition to obtain 18.7 g of Compound 23-3 ((Z)-1-bromo-2-(2-iodostyryl)benzene) as a white solid (yield: 90.5%).

1H NMR (300 MHz, CDCl3): δ (ppm) 7.87 (dd, J=7.9, 1.1 Hz, 1H), 7.57 (dd, J=7.3, 1.8 Hz, 1H), 7.11-6.93 (m, 5H), 6.89 (td, J=7.7, 1.9 Hz, 1H), 6.76 (d, J=11.8 Hz, 1H), 6.68 (d, J=11.8 Hz, 1H)

13C NMR (75 MHz, CDCl3): δ (ppm) 140.9, 139.2, 137.0, 135.4, 132.8, 131.1, 130.8, 130.6, 129.0, 128.9, 128.0, 127.1, 124.3, 100.0

Molecular weight: 383.9011 (theoretical value of C14H10BrI)

LR-Mass (EI+): 384.1, HR-Mass (EI+): 383.9018

Synthesis of Compound 23-4

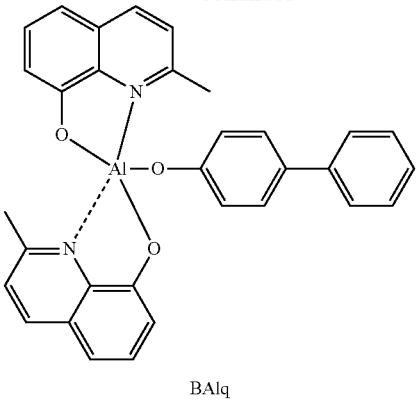

BAlq 15.1 g of Compound 23-3 (39.217 mmol), 13.697 g of tributyltin hydride (47.060 mmol), and 1.288 g of azobisisobutyronitrile (AIBN) (7.843 mmol) were added to 200 mL of toluene, and the mixture was heated and stirred under a nitrogen atmosphere. After 12 hours, the mixture was slowly cooled to ambient temperature, and then 2.283 g of tributyltin hydride (7.843 mmol) and 0.258 g of AIBN (1.569 mmol) were added thereto, and the solution was heated and stirred. When the reaction was completed, toluene was removed from the resultant, and an organic layer was separated by using a large amount of dichloromethane and $H_2O$, a tin salt was removed by using potassium fluoride and Celite, washed with a saturated sodium chloride solution, and sodium sulfate was used to remove water therefrom. The solvent was removed from the resultant thus obtained, and column chromatography was performed under a hexane condition to obtain 8.4 g of Compound 23-4 (1-bromophenanthrene) as a white solid (yield: 83.3%).

1H NMR (300 MHz, CDCl3): δ (ppm) 8.68 (d, J=8.2 Hz, 2H), 8.23 (d, J=9.2 Hz, 1H), 7.95~6.89 (m, 2H), 7.86 (d, J=9.2 Hz, 1H), 7.73~7.62 (m, 2H), 7.50 (dd, J=8.2, 7.9 Hz, 1H)

13C NMR (75 MHz, CDCl3): δ (ppm) 132.2, 132.1, 130.9, 130.8, 130.1, 128.9, 128.7, 127.4, 127.3, 127.0, 125.5, 123.9, 123.1, 122.5

Molecular weight: 255.9888 (theoretical value of C14H9Br)

LR-Mass (EI+): 256.0, HR-Mass (EI+): 255.9886

Synthesis of Compound 23-5

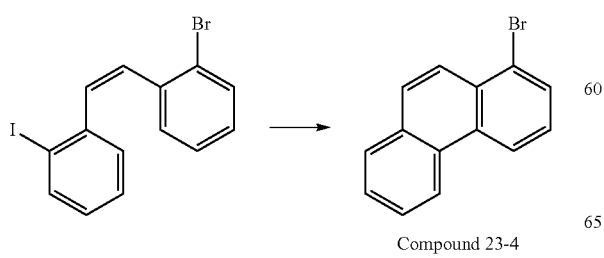

Compound 23-4

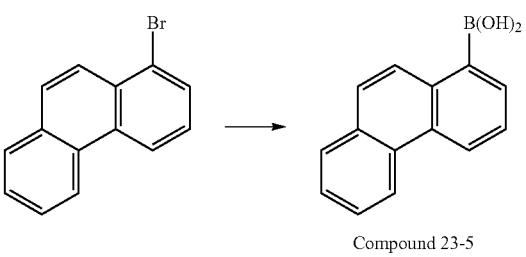 [SMILES: Brc1cccc2c1ccc1ccccc12 ; OB(O)c1cccc2c1ccc1ccccc12]

Compound 23-5

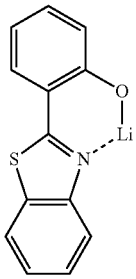

ET-D2

3 g of Intermediate 23-4 (11.667 mmol) was added to a 2-neck round bottom flask, sealed, and dried at a low pressure. 100 mL of purified tetrahydrofuran was added thereto, and a temperature was maintained at −78° C. by using dry ice and acetone. 11.667 mL of n-butyl lithium solution (2.5 mol/L in hexane) (29.168 mmol) was slowly injected thereto and stirred for 1 hour while the temperature was maintained, 6.539 mL of trimethylborate (58.336 mmol) was added, and then the solution was stirred while its temperature was slowly changed to ambient temperature. After 5 hours, a large amount (20 mL) of 1N HCl was added thereto, and the solution was stirred for 2 hours. When the reaction was completed, an organic layer was separated by using a large amount (e.g., excess) of dichloromethane and H$_2$O, and sodium sulfate was used to remove water therefrom. The solvent was removed from the resultant thus obtained, and column chromatography (eluent, dichloromethane:methanol=9:1) was performed to obtain 1.8 g of Compound 23-5 (phenanthren-1-ylboronic acid) as a white solid (yield: 69.5%).

1H NMR (300 MHz, acetone-d6): δ (ppm) 8.88 (dd, J=8.4, 5.4 Hz, 2H), 8.51 (d, J=9.0 Hz, 1H), 7.97 (d, J=7.2 Hz, 2H), 7.82 (d, J=9.0 Hz, 1H), 7.71~7.60 (m, 3H)

13C NMR (75 MHz, acetone-d6): δ (ppm) 135.0, 132.8, 131.8, 130.6, 128.3, 127.7, 126.5, 126.4, 126.3, 125.7, 124.0, 122.7

Molecular weight: 222.0852 (theoretical value of C14H11BO2)

LR-Mass (EI+): 222.0, HR-Mass (EI+): 222.0848

Synthesis of Compound 23-6

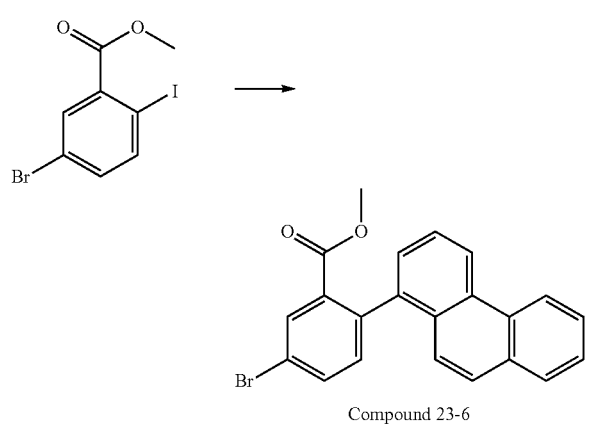

Compound 23-6

3.849 g of methyl 5-bromo-2-iodobenzoate (11.259 mmol), 3 g of Compound 23-5 (phenanthren-1-ylboronic acid) (13.510 mmol), 2 mol/L potassium carbonate (in H$_2$O, 30 mL), and 0.651 g of tetrakis(triphenylphosphine)palladium (0.563 mmol) were mixed with 100 mL of tetrahydrofuran and 30 mL of methanol under a nitrogen atmosphere, and the solution was heated and stirred. After 24 hours, completion of the reaction was confirmed by TLC, and the solvent was removed therefrom, filtered by using Celite. Then, an organic layer was separated, washed with a saturated sodium chloride solution, and sodium sulfate was used to remove water therefrom. The solvent was removed from the resultant thus obtained, and column chromatography (eluent, MC:hexane=1:4) was performed to obtain 3.5 g of Compound 23-6 (1-bromophenanthrene) as a white solid (yield: 79%).

1H NMR (300 MHz, CDCl3): δ (ppm) 8.80 (d, J=12.6 Hz, 2H), 8.22 (s, 1H), 7.88 (d, J=7.8 Hz, 1H), 7.77 (dd, J=5.1, 1.8 Hz, 1H), 7.73~7.60 (m, 4H), 7.40 (dd, J=7.8, 1.5 Hz, 2H), 7.32 (d, J=8.1 Hz, 1H), 3.41 (s, 3H)

13C NMR (75 MHz, CDCl3): δ (ppm) 166.4, 140.7, 139.0, 134.6, 133.5, 133.1, 131.7, 130.3, 130.2, 130.0, 128.5, 127.2, 126.8, 126.7, 125.7, 123.9, 122.9, 122.4, 121.5, 52.1

Molecular weight: 390.0255 (theoretical value of C22H15BrO2)

LR-Mass (EI+): 392.2, HR-Mass (EI+): 392.0257

Synthesis of Compound 23-7

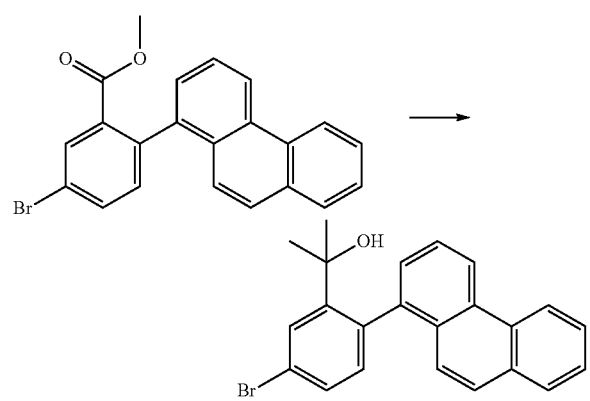

Compound 23-7

3.45 g of Compound 23-6 (methyl 5-bromo-2-(phenanthren-1-yl)benzoate) (8.818 mmol) was added to a 2-neck round bottom flask, sealed, and then dried at a low pressure. 120 mL of purified tetrahydrofuran was added thereto, 14.85 mL of methyl magnesium bromide solution (1.4 mol/L, 21.162 mmol) was slowly injected, and the solution was heated and stirred for 4 hours. Then, the solvent was removed, an organic layer was separated by using a large amount of dichloromethane and H$_2$O, washed with a saturated sodium chloride solution, and sodium sulfate was used to remove water therefrom. The solvent was removed from the resultant thus obtained, and column chromatography (eluent, MC:hexane=1:9) was performed to obtain 2.7 g of Compound 23-7 (2-(5-bromo-2-(phenanthren-1-yl)phenyl)propan-2-ol) as a white solid (yield: 75%).

1H NMR (300 MHz, CDCl3): δ (ppm) 8.77 (d, J=5.1 Hz, 2H), 8.03 (d, J=1.8 Hz, 1H), 7.89 (d, J=4.5 Hz, 1H), 7.88~7.62 (m, 4H), 7.52~7.47 (m, 2H), 7.33 (d, J=9.3 Hz, 2H), 7.03 (d, J=8.1 Hz, 1H), 1.39 (s, 3H), 1.22 (s, 3H)

13C NMR (75 MHz, CDCl3): δ (ppm) 149.5, 140.4, 1367, 134.2, 131.7, 131.0, 130.5, 130.2, 129.6, 129.4, 128.6, 128.0, 127.2, 126.9, 125.4, 125.0, 122.9, 122.5, 122.1, 73.7, 32.3, 31.7

Molecular weight: 390.0619 (theoretical value of C23H19BrO)

LR-Mass (EI+): 390.0, HR-Mass (EI+): 390.0622

Synthesis of Compound 23-8

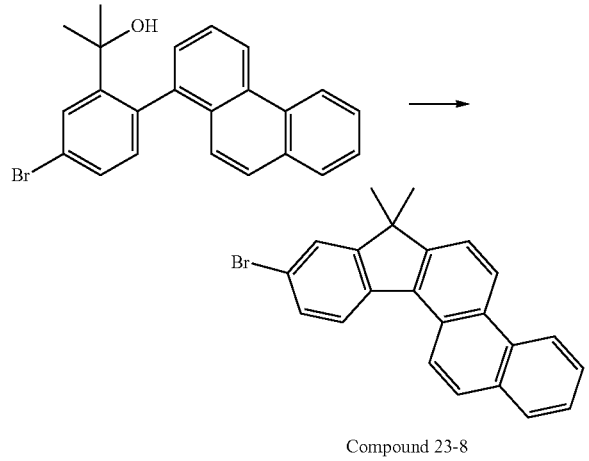

Compound 23-8

4.5 mL of sulfuric acid was added to 2.7 g of Compound 23-7 (2-(5-bromo-2-(phenanthren-1-yl)phenyl)propan-2-ol) (6.918 mmol) in 130 mL of acetic acid, a solvent, and the solution was heated and stirred for 3 hours. After the reaction was completed, a temperature of the solution was slowly changed to ambient temperature, 50 mL of H₂O was added thereto, and stirred. An organic layer was separated by using dichloromethane and H₂O, washed with a saturated sodium chloride solution, and sodium sulfate was used to remove water therefrom. The solvent was removed from the resultant thus obtained, and column chromatography was performed under a hexane condition to obtain 2.7 g of Compound 23-8 (9-bromo-7,7-dimethyl-7H-indeno[1,2-a]phenanthrene) as a white solid (yield: 75%).

1H NMR (300 MHz, CDCl3): δ (ppm) 8.76 (t, J=5.4 Hz, 2H), 8.63 (d, J=9.3 Hz, 1H), 8.24 (d, J=8.4 Hz, 1H), 7.74 (d, J=8.7 Hz, 1H), 7.9~77.91 (m, 2H), 7.7~7.59 (m, 4H), 1.59 (s, 6H)

13C NMR (75 MHz, CDCl3): δ (ppm) 157.0, 152.7, 130.2, 128.6, 127.9, 126.9, 126.7, 126.5, 126.2, 124.7, 123.0, 122.3, 120.9, 120.7, 46.6, 26.9

Molecular weight: 372.0514 (theoretical value of C23H17Br)

LR-Mass (EI+): 372.0, HR-Mass (EI+): 372.0514

Synthesis of Compound 23-9

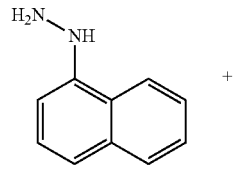 +

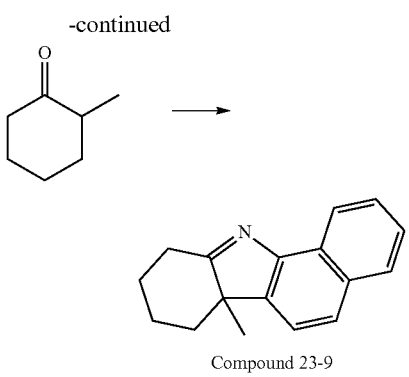

Compound 23-9

50 g of 1-naphthylhydrazine (316.30 mmol) and 170 ml of acetic acid were added to a 500 ml round bottom flask and heated, so that a temperature of the solution was 60° C. 35.45 g of 2-methylcyclohexanone (316.30 mmol) was dropwisely added to the heated solution in the flask. When the addition was completed, the solution was refluxed for 8 hours. After completing the reaction, 100 ml of water was added thereto, and the solution was basified by using sodium hydroxide. An organic layer was extracted with water and ethyl acetate, water was removed with magnesium sulfate, concentrated at a low pressure, and purified by using column chromatography by using hexane and ethyl acetate as an eluent to obtain 62.47 g of Compound 23-9 (265.69 mmol) (yield: 84%).

Synthesis of Compound 23-10

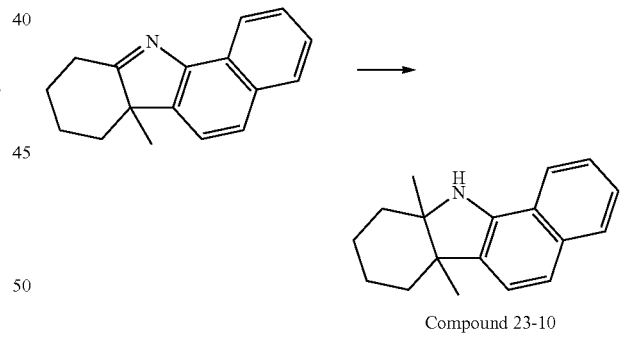

Compound 23-10

50 g of Compound 23-9 (212.64 mmol) was dissolved in 570 mL of toluene in a 2-neck round bottom flask in a nitrogen atmosphere, and a temperature of the solution was decreased to −10° C. 202 ml of 1.6 M methyllithium (318.96 mmol) was slowly and dropwisely added to the solution in the flask, and allowed to react for 3 hours at −10° C. When the reaction was completed, water was slowly added until reactivity was undetecable. An organic layer was extracted with water and ethyl acetate, water was removed with magnesium sulfate, and concentrated at a low pressure. The resultant was then purified by using column chromatography by using hexane and ethylacetate as an eluent to obtain 40.59 g of Compound 23-10 (161.61 mmol) (yield: 76%).

Synthesis of Compound 23

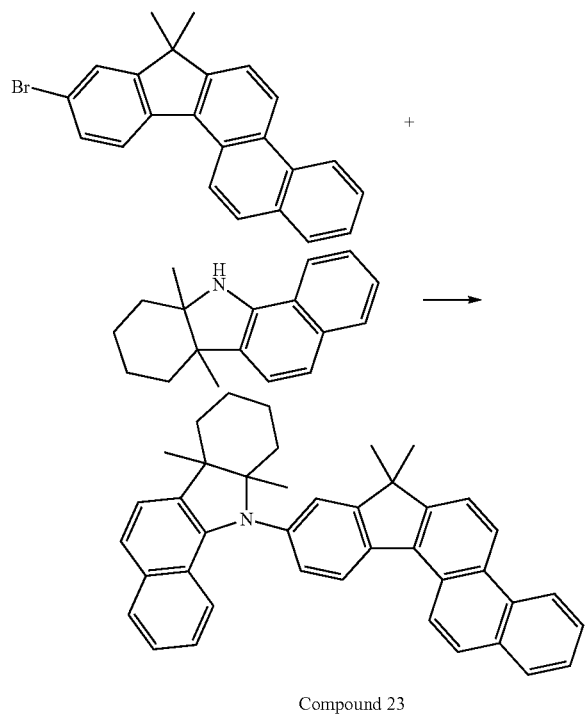

Compound 23

10 g of Compound 23-8 (26.88 mmol), 8.77 g of Compound 23-10 (34.95 mmol), 0.15 g of palladium acetate (Pd(OAc)$_2$) (0.54 mmol), 5.22 g of sodium tert-butoxide (53.76 mmol), 0.11 g of tritert-butyl phosphine (0.54 mmol), and 100 ml of toluene were added to a round bottom flask and reacted at a reaction temperature of 100° C. for 2 hours. When the reaction was completed, the solution was filtered, the filtered solution was concentrated, and then purified by using a column chromatography. The produced solid was recrystallized with toluene and methanol, filtered, and dried to obtain 9.49 g of Compound 23 (17.47 mmol, yield: 65%).

MS: m/z 543 [M]+

Synthesis Example 2: Synthesis of Compound 25

<Compound 25>

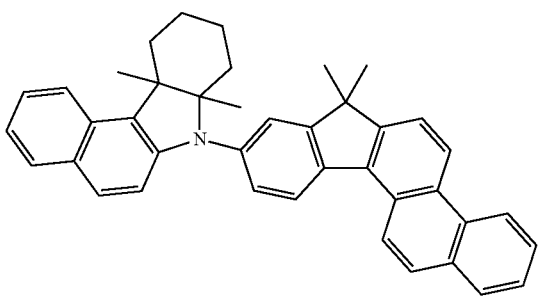

9.93 g (18.28 mmol) of Compound 25 (yield: 68%) was obtained in the same manner as in the synthesis of Compound 23 of Synthesis Example 1, except that 2-naphthylhydrazine was used instead of 1-naphthylhydrazine.

MS: m/z 543 [M]+

Synthesis Example 3: Synthesis of Compound 33

Synthesis of Compound 33-1

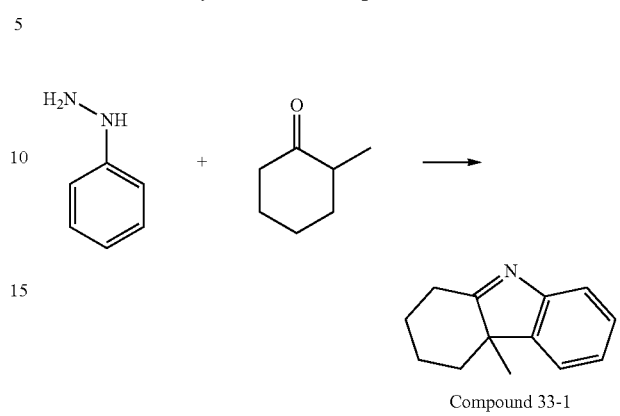

Compound 33-1

50 g of phenylhydrazine (462 mmol) and 170 ml of acetic acid were added to a 500 ml round bottom flask and heated, so that a temperature of the solution was 60° C. 51.9 g of 2-methylcyclohexanone (462 mmol) was dropwisely added to the heated solution in the flask. When the addition was completed, the solution was refluxed for 8 hours. After completing the reaction, 100 ml of water was added thereto, and the solution was basified by using sodium hydroxide. An organic layer was extracted with water and ethylacetate, water was removed with magnesium sulfate, concentrated at a low pressure, and purified by using column chromatography by using hexane and ethyl acetate as an eluent to obtain 72 g of Compound 33-1 (388.08 mmol) (yield: 84%).

Synthesis of Compound 33-2

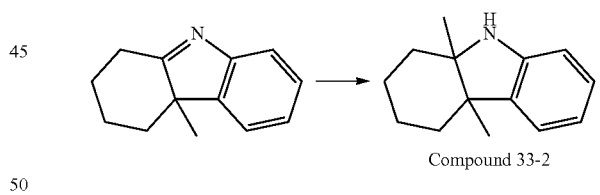

Compound 33-2

57 g of Compound 33-1 (308 mmol) was dissolved in 570 mL of toluene in a 2 L round bottom flask under a nitrogen atmosphere, and a temperature of the solution was decreased to −10° C. 300 ml of 1.6 M methyllithium (474 mmol) was slowly and dropwisely added to the solution in the flask, and allowed to react for 3 hours at −10° C. When the reaction was completed, water was slowly added until reactivity was undetecable. An organic layer was extracted with water and ethyl acetate, water was removed with magnesium sulfate, and concentrated at a low pressure. The resultant was then purified by using column chromatography by using hexane and ethyl acetate as an eluent to obtain 47 g of Compound 33-2 (234.08 mmol) (yield: 76%).

Synthesis of Compound 33-3

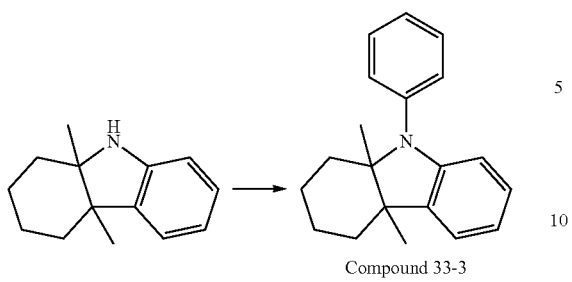

Compound 33-3

40 g of Compound 33-2 (199 mmol), 48.6 g of iodobenzene (238 mmol), 0.89 g of tris(dibenzylideneacetone)dipalladium(0) (4 mmol), 2.47 g of 2,2-bisdiphenylphosphino-1,1'-binaphthyl (4 mmol), and 38.19 g of sodium tert-butoxide (397 mmol) were added to 400 ml of toluene in a 1 L round bottom flask, and the solution was refluxed for 8 hours. After completing the reaction, the solution was filtered through Celite, concentrated at a low pressure, and purified by using column chromatography by using hexane as an eluent to obtain 44 g of Compound 33-3 (157.21 mmol) (yield: 79%).

Synthesis of Compound 33-4

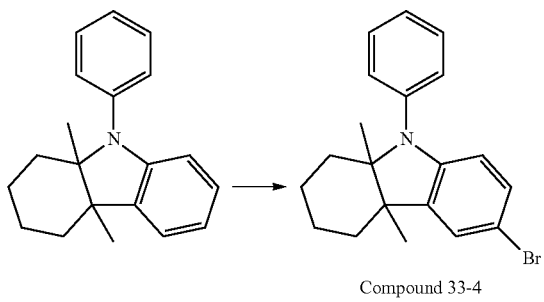 [SMILES: CC12CCCCC1(C)N(c1ccccc1)c1ccccc12 ; CC12CCCCC1(C)N(c1ccccc1)c1ccc(Br)cc12]

Compound 33-4

44 g of Compound 33-3 (158 mmol) and 130 ml of dimethylformamide were added to a 500 ml round bottom flask, and a temperature of the solution was decreased to 0° C. 25.2 g of N-bromosuccinimide (142 mmol) was dissolved in 220 ml of dimethylformamide and slowly and dropwisely added to the solution. When the addition was completed, a temperature of the solution was increased to ambient temperature, and then the solution was stirred for 2 hours. When the reaction was completed, an organic layer was extracted with water and dichloromethane, water was removed with magnesium sulfate, and concentrated at a low pressure. Hexane was added to the produced crystals, and the solution was filtered to obtain 45 g of Compound 33-4 (126.4 mmol) (yield: 80%).

Synthesis of Compound 33-5

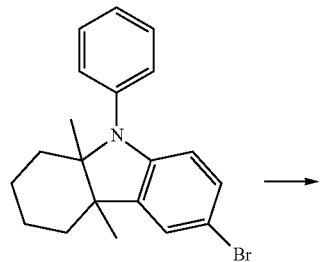

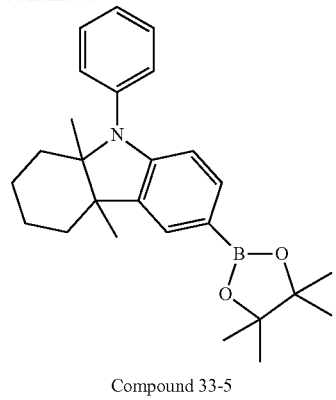

Compound 33-5

40 g of Compound 33-4 (112 mmol), 34 g of bis(pinacolato)diboron (134 mmol), 2.73 g of palladium(II) chloride-1-1'-bis(diphenylphosphino)ferrocene (3 mmol), 32.9 g of potassium acetate (335 mmol), and 480 ml of toluene were added to a 1 L round bottom flask, and the solution was refluxed for 8 hours. After completing the reaction, the solution was filtered through Celite, concentrated at a low pressure, and purified by using column chromatography by using hexane and ethyl acetate as an eluent to obtain 26 g of Compound 33-5 (64.96 mmol) (yield: 58%).

Synthesis of Compound 33

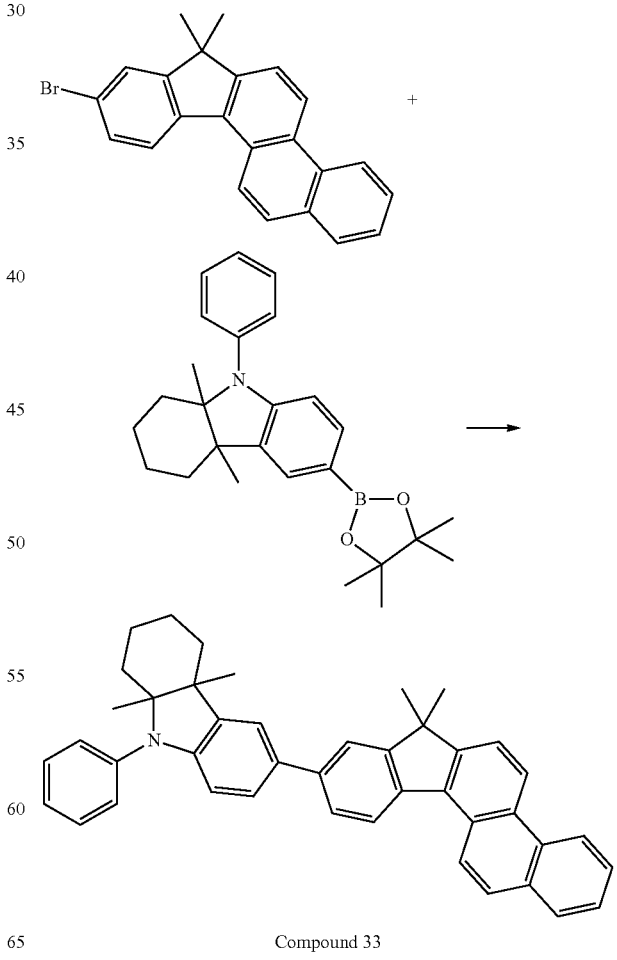

Compound 33

5.0 g of Compound 23-8 (13.44 mmol), 6.50 g of Compound 33-5 (16.13 mmol), 0.27 g of tetrakis(triphenylphosphine) palladium (0.20 mmol), 2.79 g of potassium carbonate (20.16 mmol), 25 ml of 1,4-dioxane, 25 ml of toluene, and 10 ml of water were added to a round bottom flask, and the solution was refluxed. When the reaction was completed, water and hexane was added thereto. The produced crystals were filtered. The crystals were re-crystallized to obtain 5.51 g of Compound 33 (9.68 mmol) (yield: 72%).

MS: m/z 569[M]+

Synthesis Example 4: Compound 35

Compound 35

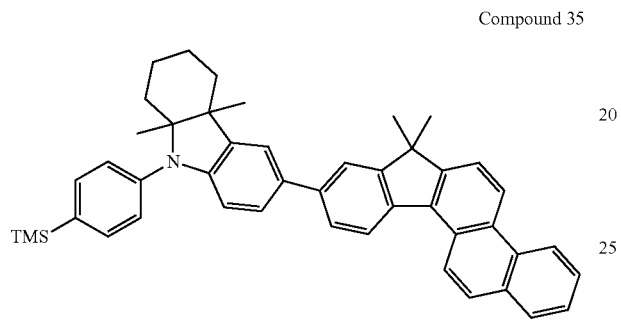

5.60 g of Compound 35 (8.74 mmol) (yield: 65%) was obtained in the same manner as in the synthesis of Compound 33 of Synthesis Example 3, except that (4-iodophenyl)trimethylsilane was used instead of iodobenzene.

MS: m/z 641 [M]+

Synthesis Example 5: Compound 37

Compound 37

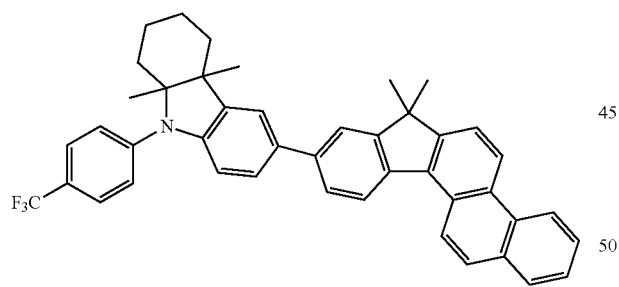

5.31 g of Compound 37 (8.33 mmol) (yield: 62%) was obtained in the same manner as in the synthesis of Compound 33 of Synthesis Example 3, except that trimethyl(4-(trifluoromethyl)phenyl)silane was used instead of iodobenzene.

MS: m/z 637 [M]+

Example 1

An ITO glass substrate (available from Corning Co.) including an ITO layer having a thickness of 15 Ω/cm² (1,200 Å), as a substrate and an anode, was cut to a size of 50 mm×50 mm×0.7 mm, washed with ultrasonic waves in isopropyl alcohol and pure water for 5 minutes each, and then cleaned with UV and ozone for 30 minutes. The ITO glass substrate was then mounted on a vacuum depositor.

4,4',4''-tris(N-(2-naphthyl)-N-phenylamino)triphenylamine (2T-NATA) was deposited on the ITO anode to form an HIL having a thickness of 600 Å, and 4,4'-bis[N-(1-naphthyl)-N-phenylamino]biphenyl (NPB) was deposited on the HIL to form an HTL having a thickness of 300 Å.

β-ADN (a host) and Compound 23 (a dopant) were co-deposited at a weight ratio of 95:5 on the HTL to form an EML having a thickness of 400 Å.

Then, Compound 201 was deposited on the EML to form an ETL having a thickness of 300 Å. LiF was deposited on the ETL to form an EIL having a thickness of 10 Å, and Al was deposited on the EIL to form a second electrode (a cathode) having a thickness of 1,100 Å, thereby completing manufacture of an OLED. An apparatus for deposition in the specification was Suicel plus 200 depositor available from Sunic System.

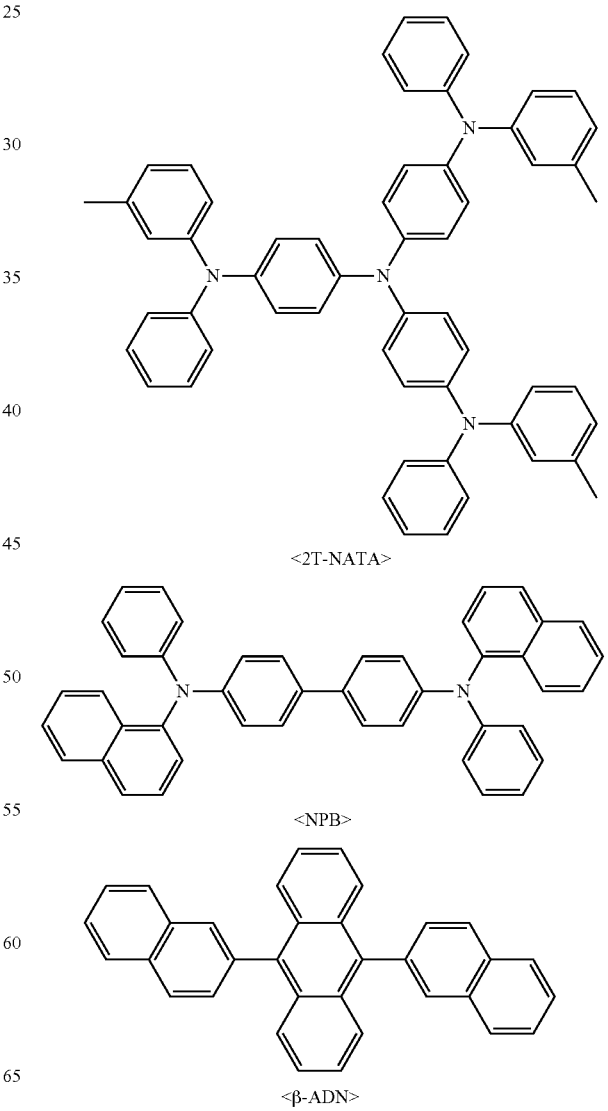

<Compound 201>

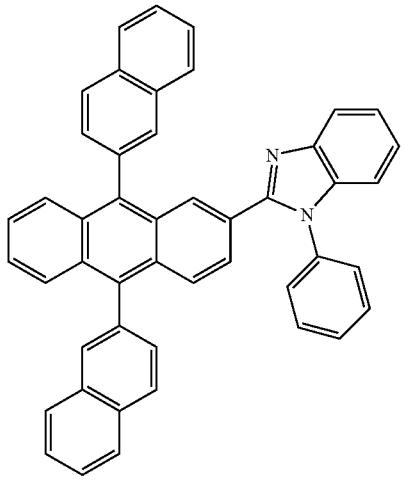

<Dopant A>

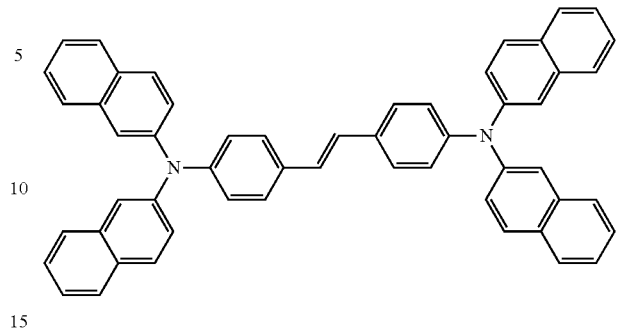

Example 2

An OLED was manufactured in the same manner as in Example 1, except that Compound 25 was used instead of Compound 23 in the formation of the EML.

Example 3

An OLED was manufactured in the same manner as in Example 1, except that Compound 33 was used instead of Compound 23 in the formation of the EML.

Example 4

An OLED was manufactured in the same manner as in Example 1, except that Compound 35 was used instead of Compound 23 in the formation of the EML.

Example 5

An OLED was manufactured in the same manner as in Example 1, except that Compound 37 was used instead of Compound 23 in the formation of the EML.

Comparative Example 1

An OLED was manufactured in the same manner as in Example 1, except that Dopant A was used instead of Compound 23 in the formation of the EML.

Comparative Example 2

An OLED was manufactured in the same manner as in Example 1, except that Dopant B was used instead of Compound 23 in the formation of the EML.

<Dopant B>

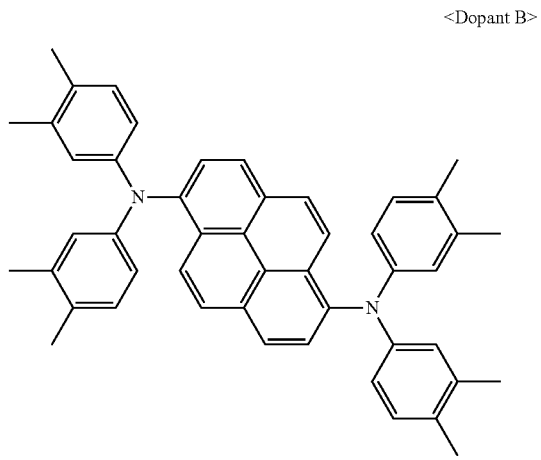

Evaluation

Driving voltages, current densities, efficiencies, and color purities of the OLEDs prepared in Examples 1 to 5 and Comparative Examples 1 and 2 were evaluated by using Kethley SMU 236 and PR650 Spectroscan Source Measurement Unit (PhotoResearch), and the results are shown in Table 1 (T95 life was time consumed for an OLED to have 95% reduced brightness after driving the device under a condition of a current density of 10 mA/cm$^2$ compared to its initial brightness). Results are shown in Table 1, below.

TABLE 1

| | Host | Dopant | Driving voltage [V] | Efficiency [cd/A] | Color coordination CIEx | CIEy | T95 Life [hr] |
|---|---|---|---|---|---|---|---|
| Example 1 | β-ADN | Compound 23 | 3.5 | 5.5 | 0.150 | 0.118 | 220 |
| Example 2 | β-ADN | Compound 25 | 3.5 | 5.4 | 0.150 | 0.124 | 200 |
| Example 3 | β-ADN | Compound 33 | 3.5 | 5.5 | 0.149 | 0.120 | 240 |
| Example 4 | β-ADN | Compound 35 | 3.4 | 5.6 | 0.150 | 0.126 | 180 |
| Example 5 | β-ADN | Compound 37 | 3.2 | 4.8 | 0.148 | 0.130 | 160 |
| Comparative Example 1 | β-ADN | Dopant A | 4.5 | 4.2 | 0.152 | 0.162 | 70 |
| Comparative Example 2 | β-ADN | Dopant B | 4.4 | 5.4 | 0.151 | 0.154 | 120 |

Referring to Table 1, when an OLED included a compound having a structure represented by Formula 1 as a dopant of a blue emission layer, the OLED exhibited better efficiencies and lifespan than those of another OLED including a different compound as the dopant.

By way of summation and review, some blue organic light-emitting devices including an anthracene derivative may have room for improvement in terms of its color purity, efficiency, and lifespan. According to an embodiment, an organic light-emitting device may have a high color purity, a high efficiency, and a long lifespan by including a non-arylamine compound of a fluorene-based derivative as a blue organic light-emitting material.

As described above, an OLED including the compound according to the one or more of the above embodiments may have improved color purity, a high efficiency, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Formula 1, below:

<Formula 1>

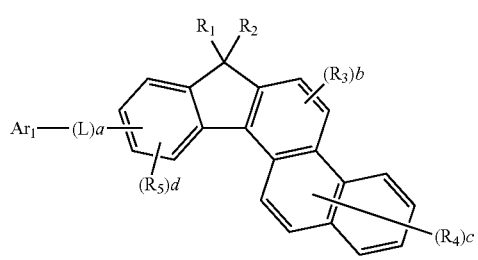

wherein, in Formula 1,

L is selected from a single bond, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;

$R_1$ to $R_5$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

$Ar_1$ is selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_3$)($Q_4$)($Q_5$), and —B($Q_6$)($Q_7$), provided that $Ar_1$ does not include a —N($Q_1$)($Q_2$) moiety;

a, b, c, and d are each independently an integer selected from 0 to 6;

at least one substituent selected from the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, $C_1$-$C_{60}$ alkyl group, $C_2$-$C_{60}$ alkenyl group, $C_2$-$C_{60}$ alkynyl group, $C_1$-$C_{60}$ alkoxy group, $C_3$-$C_{10}$ cycloalkyl group, $C_2$-$C_{10}$ heterocycloalkyl group, $C_3$-$C_{10}$ cycloalkenyl group, $C_2$-$C_{10}$ heterocycloalkenyl group, $C_6$-$C_{60}$ aryl group, $C_6$-$C_{60}$ aryloxy group, $C_6$-$C_{60}$ arylthio group, $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group[1], a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group.

2. The compound as claimed in claim 1, wherein, in Formula 1, $R_1$ and $R_2$ are each independently selected from a substituted or unsubstituted $C_1$-$C_{60}$ alkyl group and a substituted or unsubstituted $C_6$-$C_{60}$ aryl group.

3. The compound as claimed in claim 1, wherein, in Formula 1, $R_1$ and $R_2$ are each independently a methyl group or a phenyl group.

4. The compound as claimed in claim 1, wherein, in Formula 1, $R_3$ to $R_5$ are each independently a hydrogen or a deuterium.

5. The compound as claimed in claim 1, wherein, in Formula 1, $Ar_1$ is selected from a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group.

6. The compound as claimed in claim 1, wherein, in Formula 1, $Ar_1$ is a group represented by one of Formulae 7a to 7f, below:

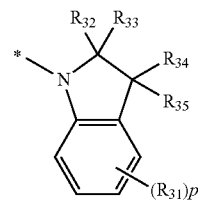

7a

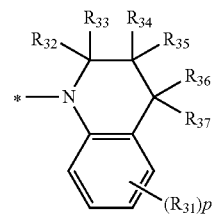

7b

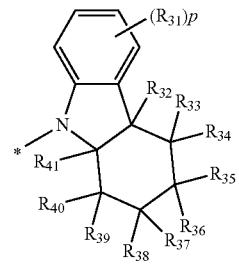

7c

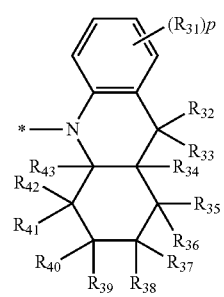

7d

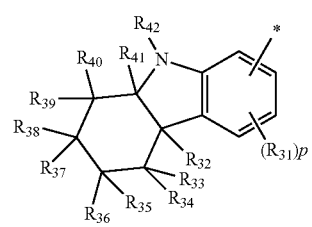

7e

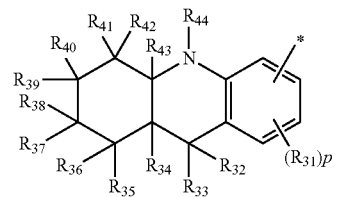

7f wherein, in Formulae 7a to 7f, $R_{31}$ to $R_{44}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

p is an integer selected from 1 to 4; when p is 2 or greater, each $R_{31}$ is identical to or different from each other; and

* is a binding site to a neighboring atom.

7. The compound as claimed in claim 6, wherein, in Formula 1, adjacent ones of the plurality of $R_{31}$ link to each other and form a ring.

8. The compound as claimed in claim 1, wherein, in Formula 1, a and d are each independently an integer selected from 0 to 4, and a sum of a and d is 4.

9. The compound as claimed in claim 1, wherein, in Formula 1, b is 1 or 2.

10. The compound as claimed in claim 1, wherein, in Formula 1, c is an integer selected from 0 to 6.

11. The compound as claimed in claim 1, wherein the compound represented by Formula 1 is represented by Formula 2, below:

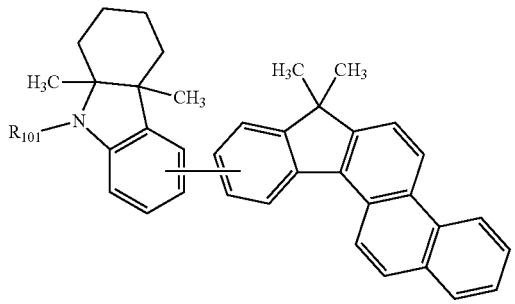

<Formula 2> wherein, in Formula 2, $R_{101}$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

12. The compound as claimed in claim 1, wherein the compound represented by Formula 1 is represented by Formula 3, below:

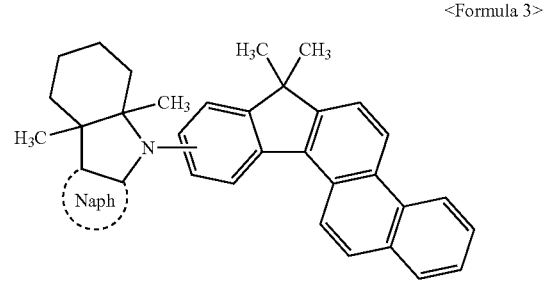

<Formula 3> wherein, in Formula 3, Naph denotes a naphthyl group.

13. The compound as claimed in claim 12, wherein a

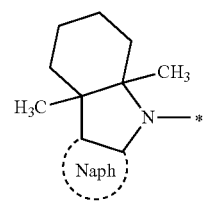

moiety of Formula 3 is or

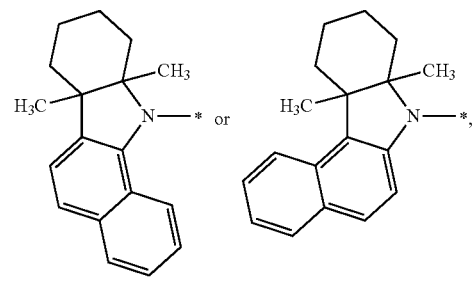

in which * denotes a binding site to a neighboring atom.

14. The compound as claimed in claim 1, wherein the compound represented by Formula 1 is one of Compounds 1 to 88, below:

[1]

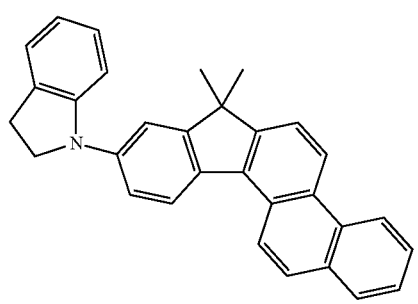

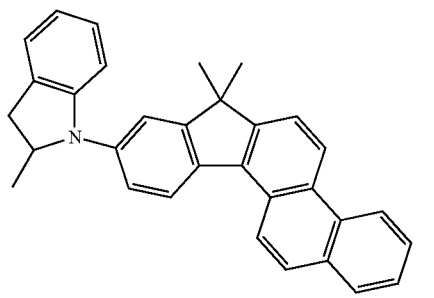 [2]
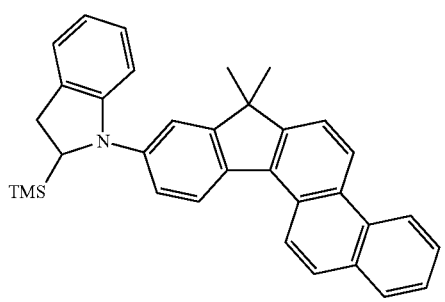 [3]
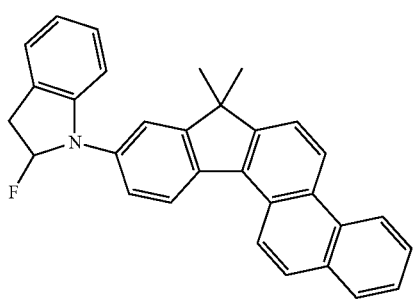 [4]
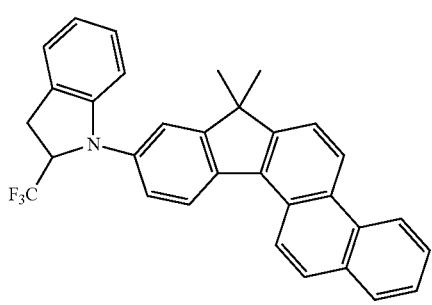 [5]
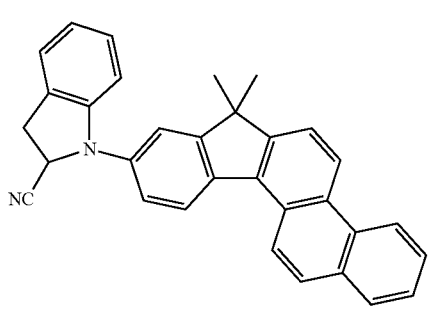 [6]
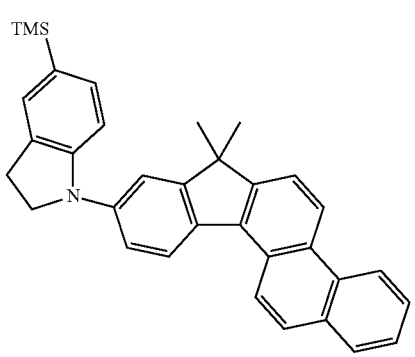 [7]
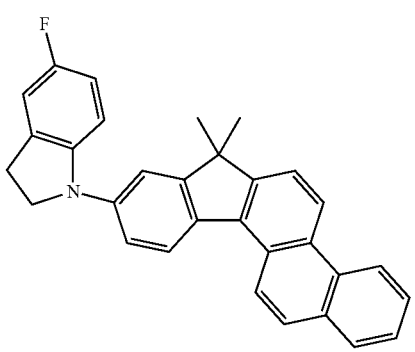 [8]
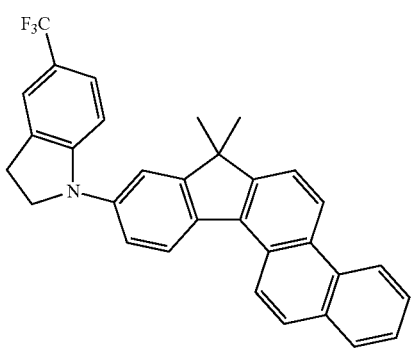 [9]
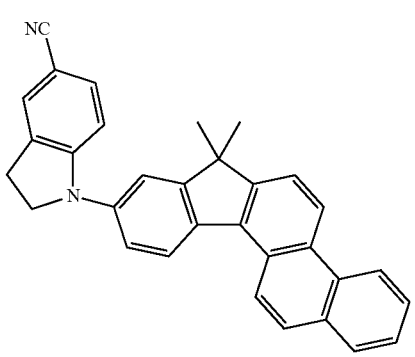 [10]

115
-continued
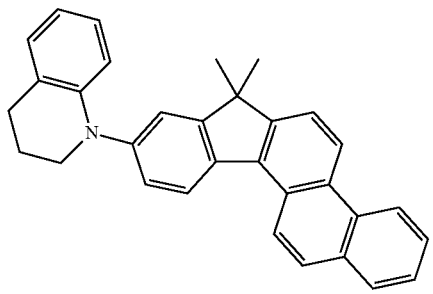
[11]
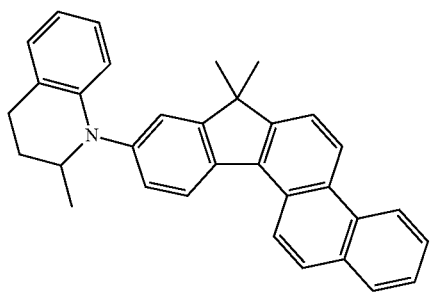
[12]
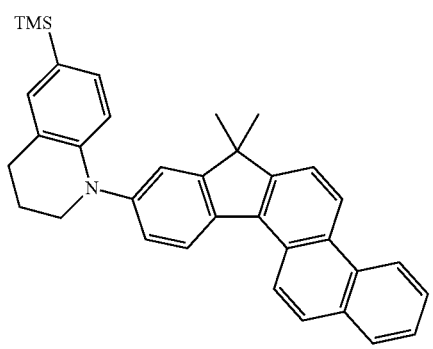
[13]
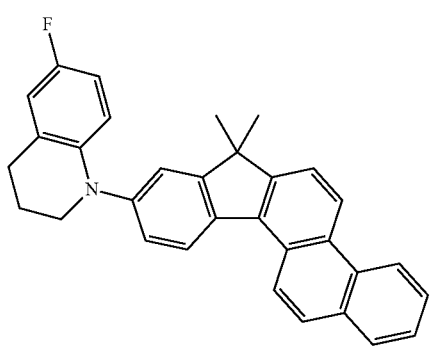
[14]
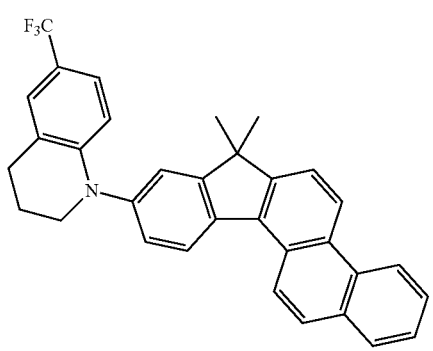
[15]
116
-continued
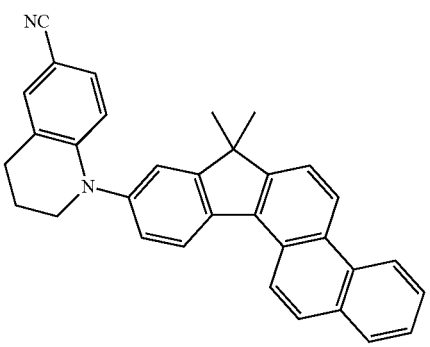
[16]
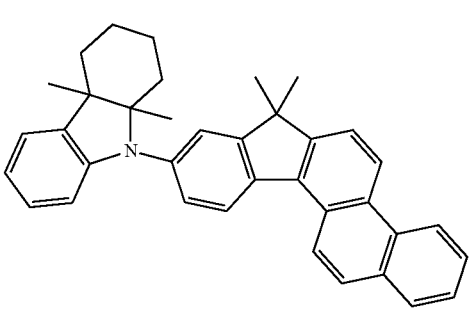
[17]
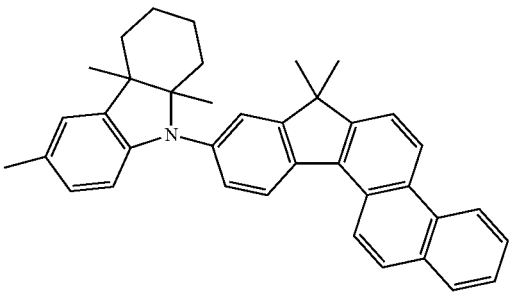
[18]
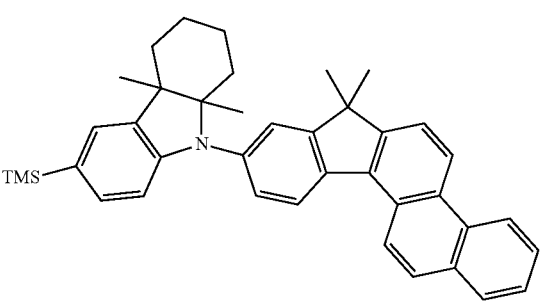
[19]
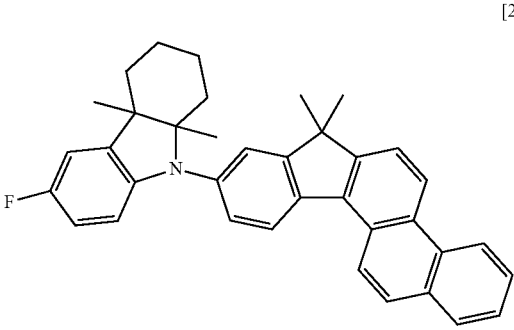
[20]

117
-continued
[21]
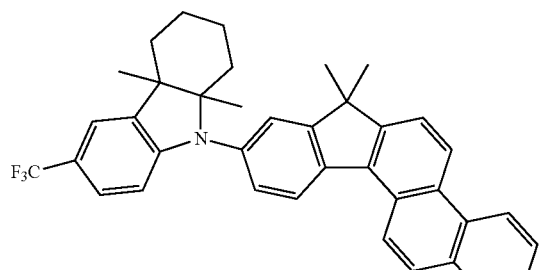
[22]
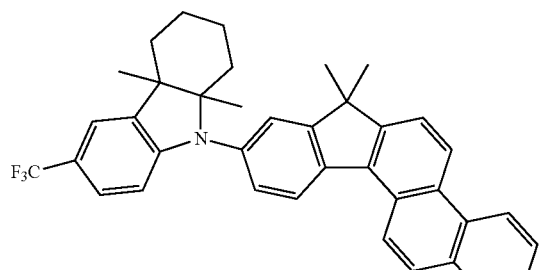
[23]
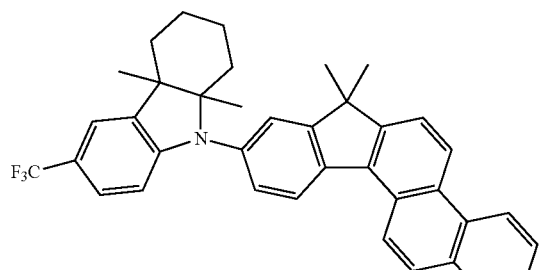
[24]
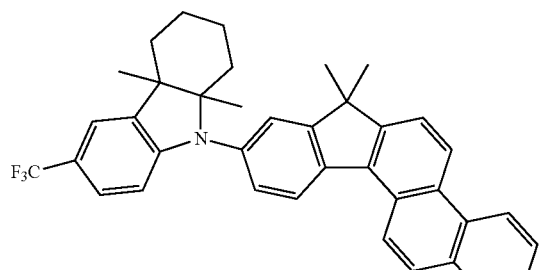
[25]
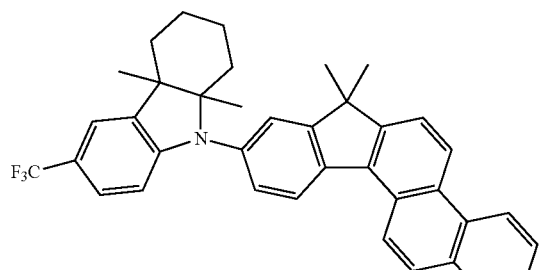
118
-continued
[26]
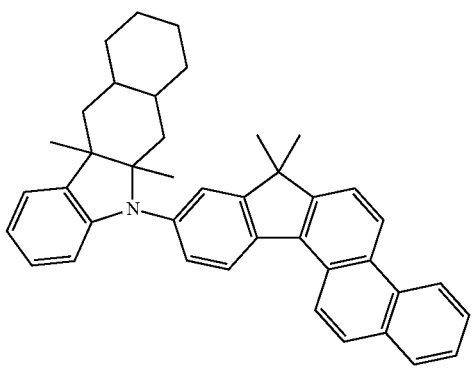
[27]
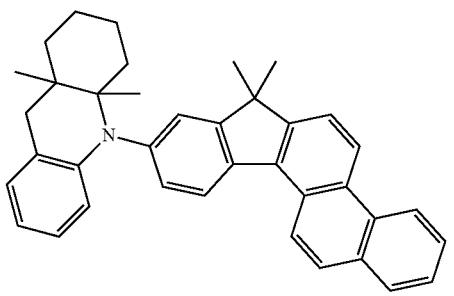
[28]
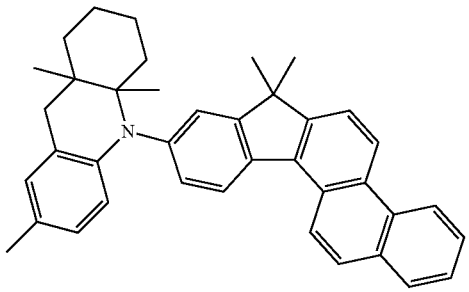
[29]
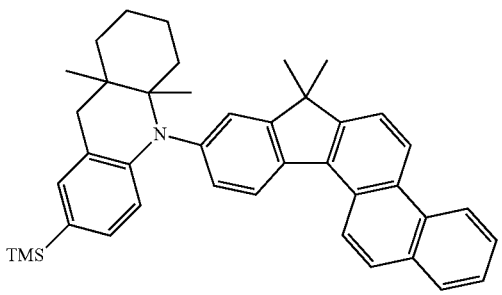
[30]
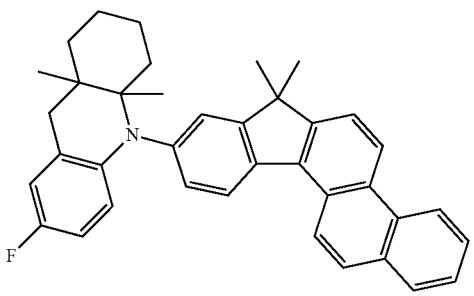

119
-continued
[31]
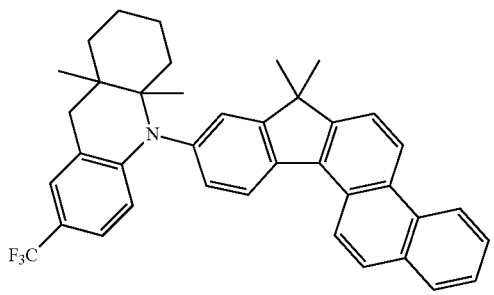
[32]
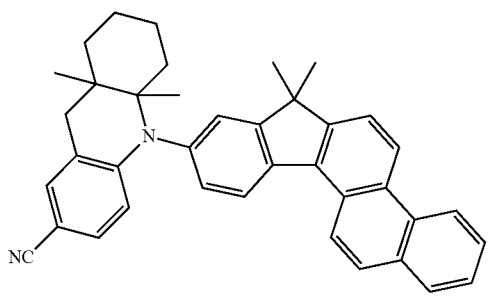
[33]
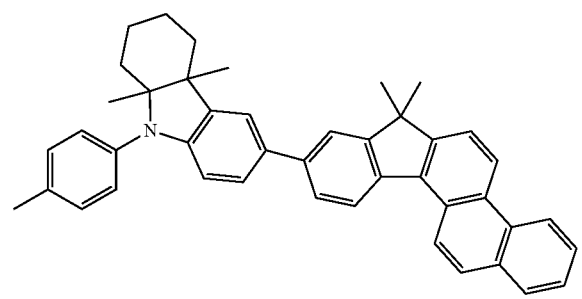
[34]
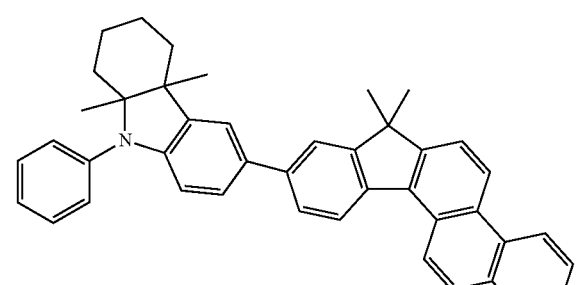
[35]
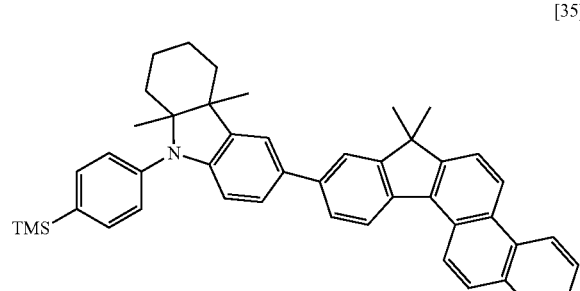
120
-continued
[36]
[37]
[38]
[39]
[40]

121
-continued
[41]
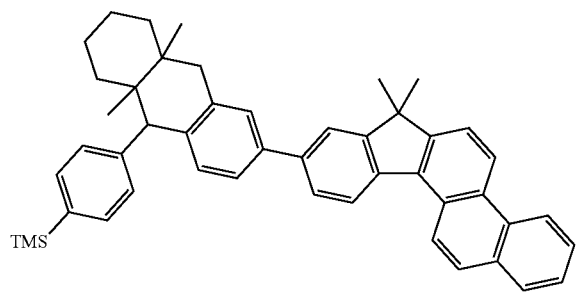
[42]
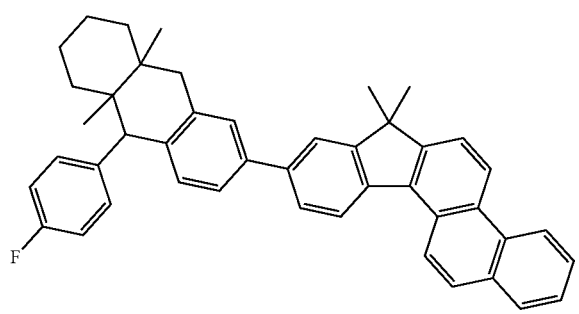
[43]
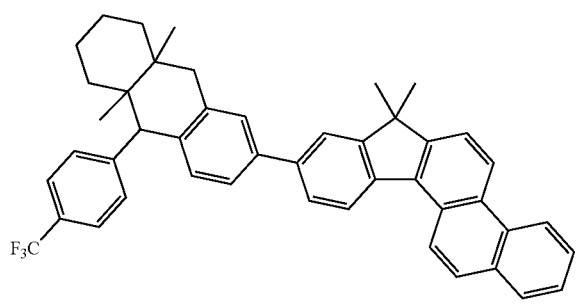
[44]
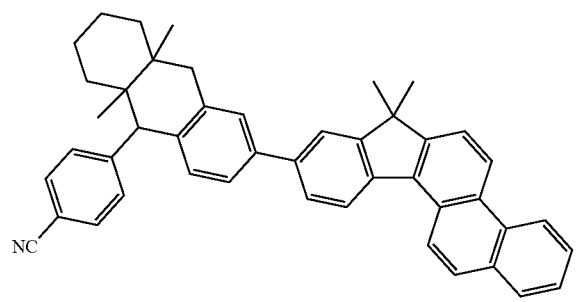
[45]
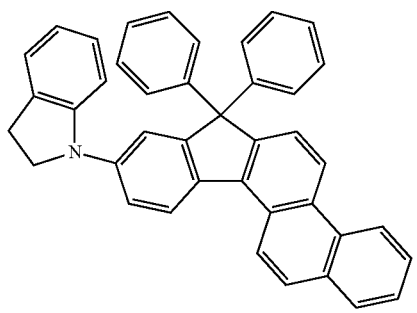
122
-continued
[46]
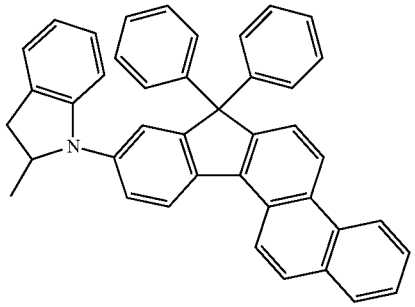
[47]
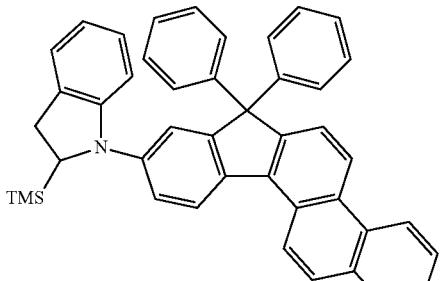
[48]
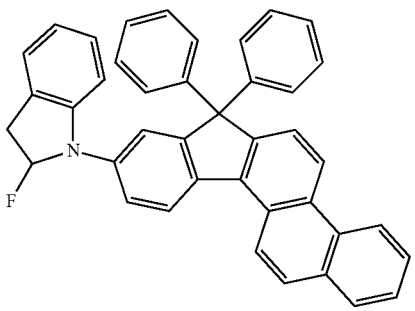
[49]
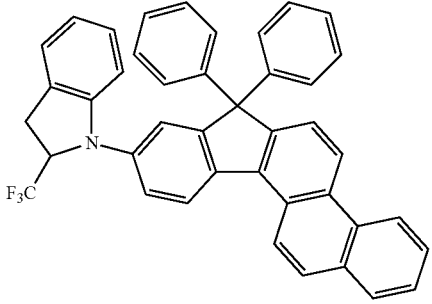
[50]
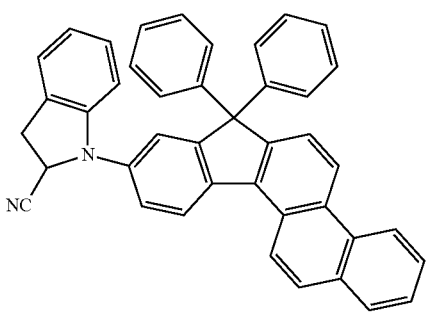

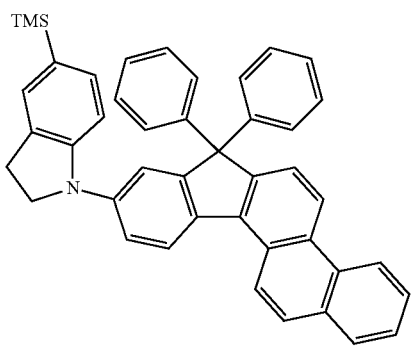
[51]
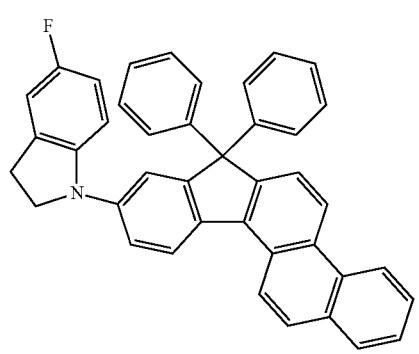
[52]
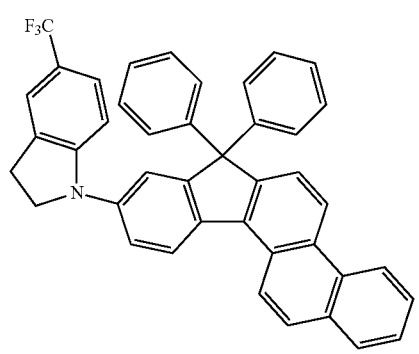
[53]
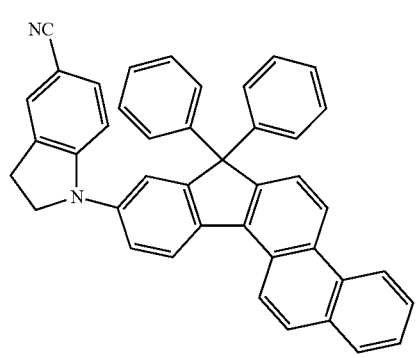
[54]
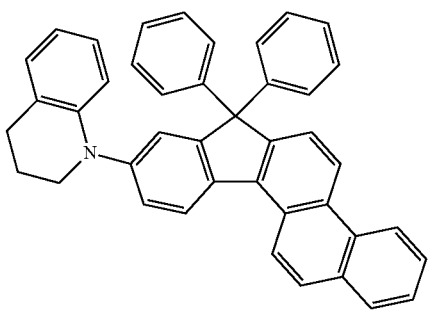
[55]
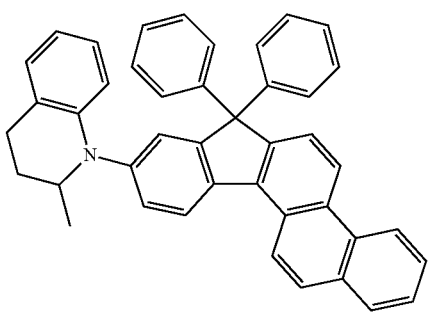
[56]
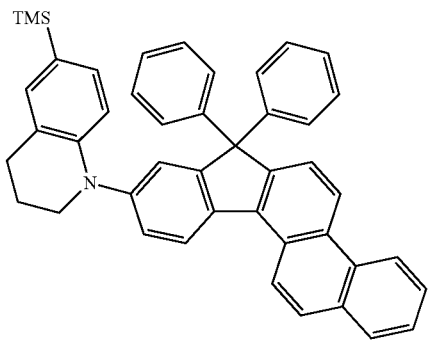
[57]
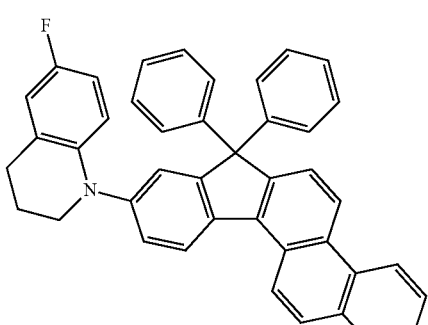
[58]
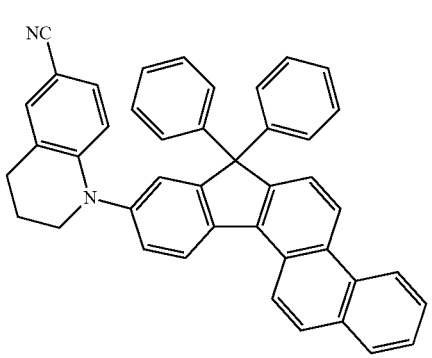
[59]

-continued
[60]
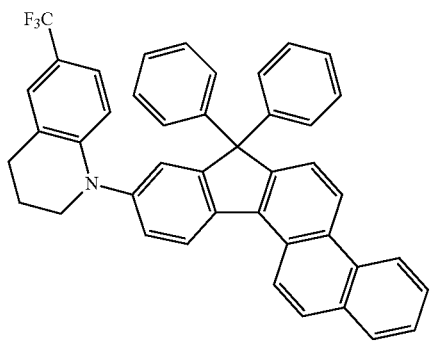
[61]
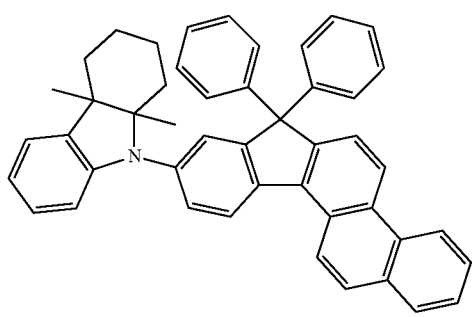
[62]
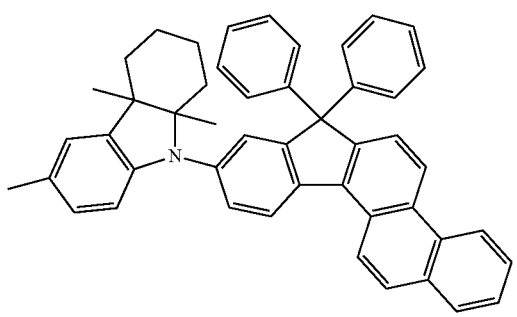
[63]
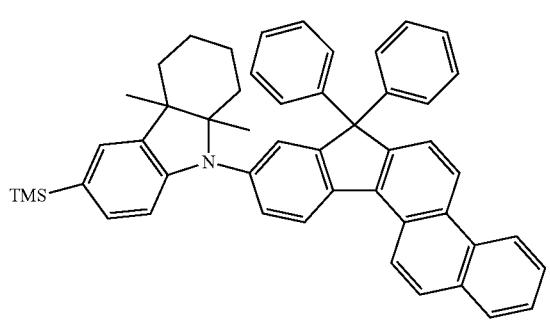
[64]
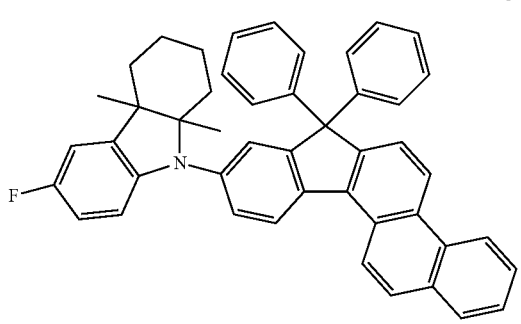
-continued
[65]
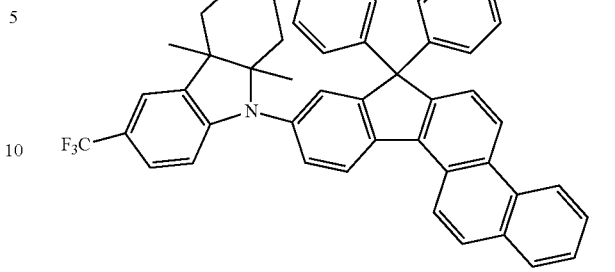
[66]
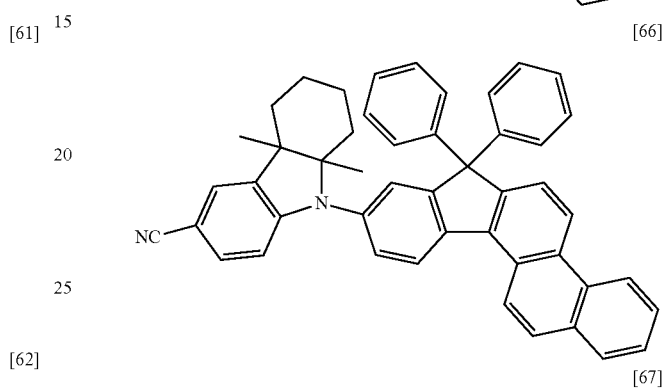
[67]
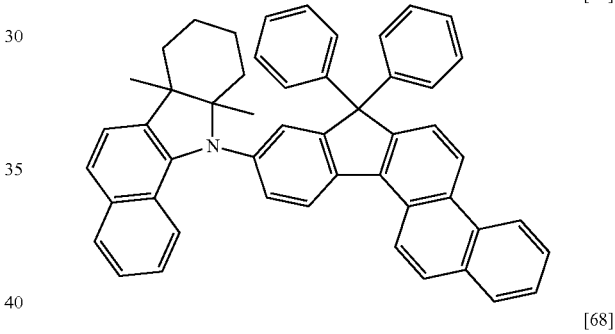
[68]
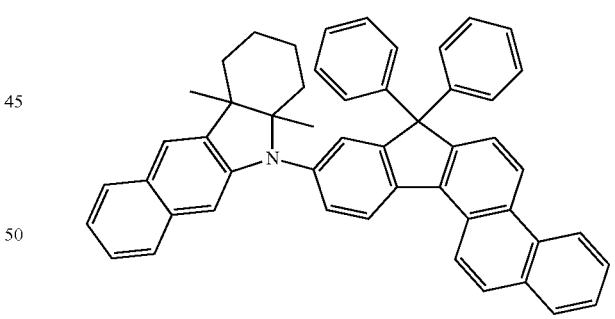
[69]
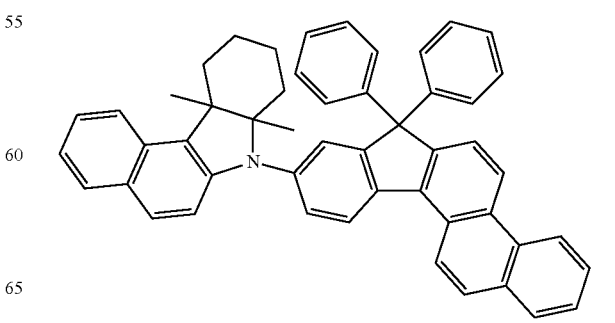

[70]
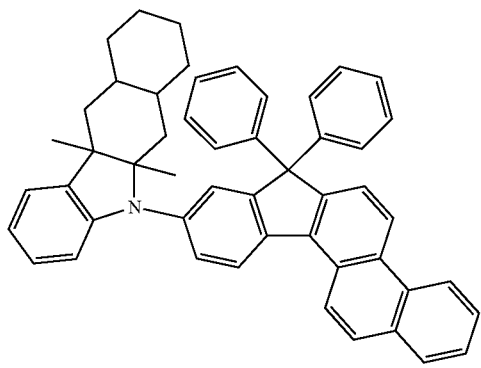
[71]
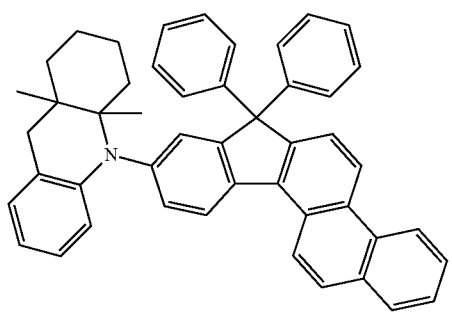
[72]
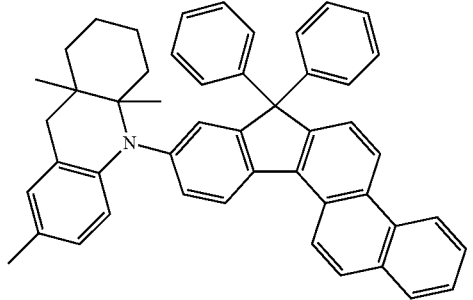
[73]
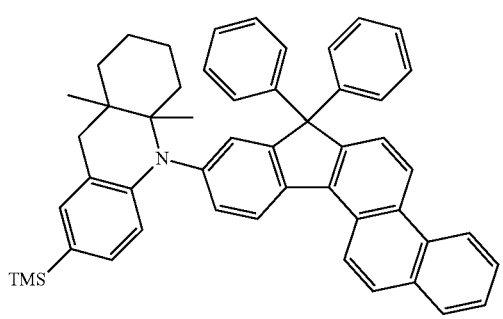
[74]
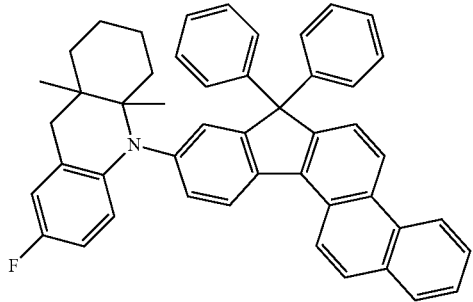
[75]
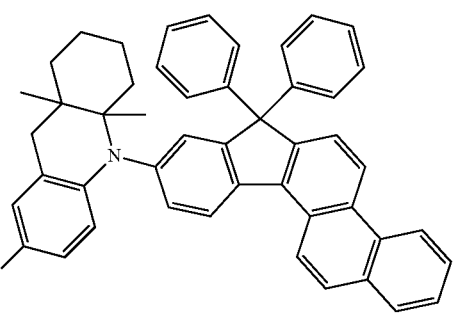
[76]
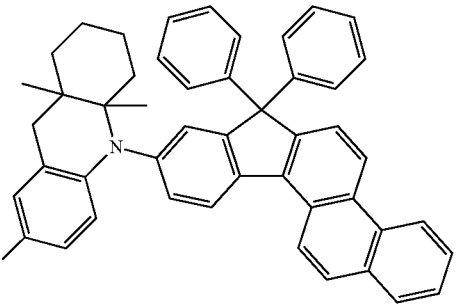
[77]
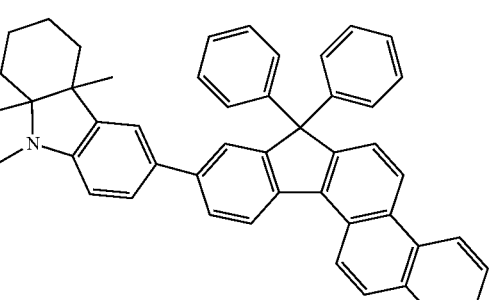
[78]
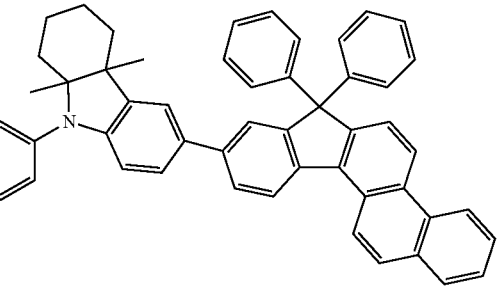
[79]
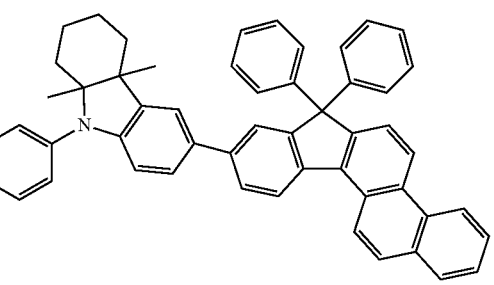

-continued

[80]
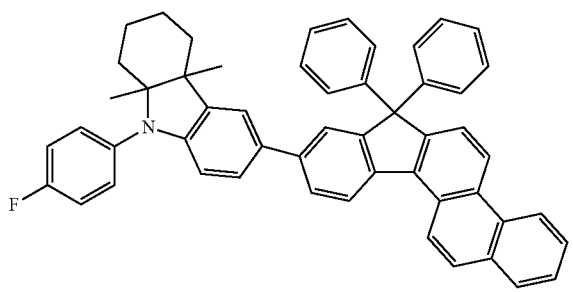

[81]
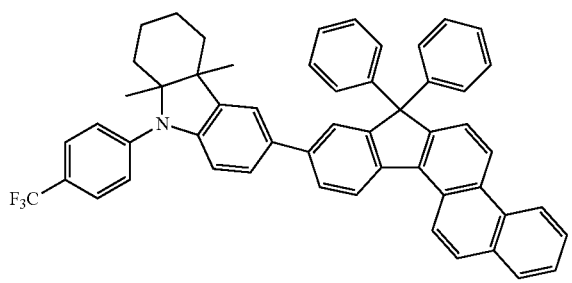

[82]
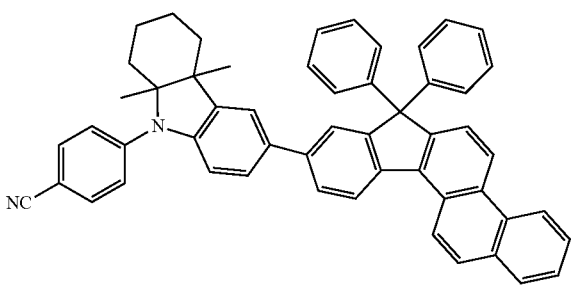

[83]
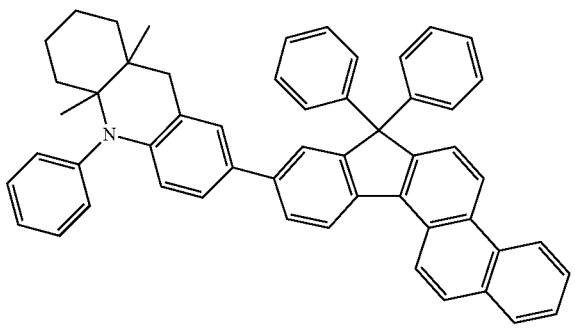

[84]
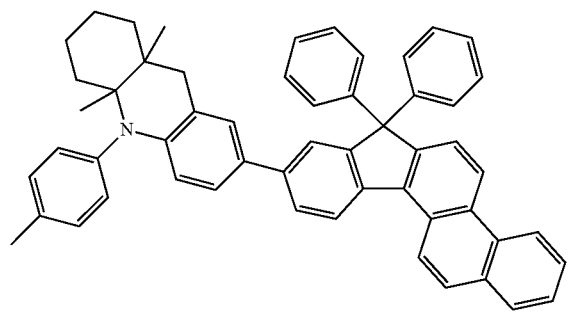

-continued

[85]
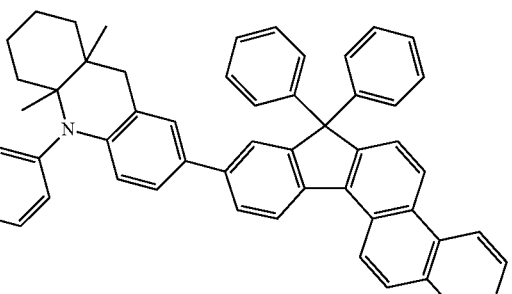

[86]
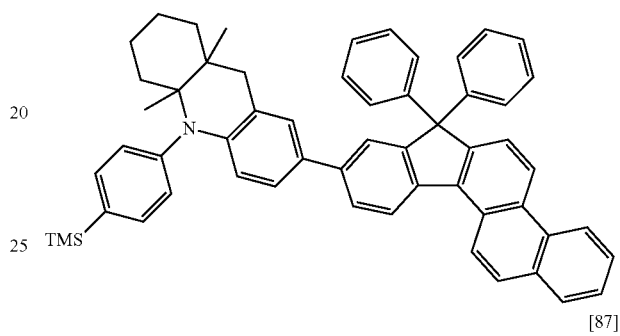

[87]

[88]
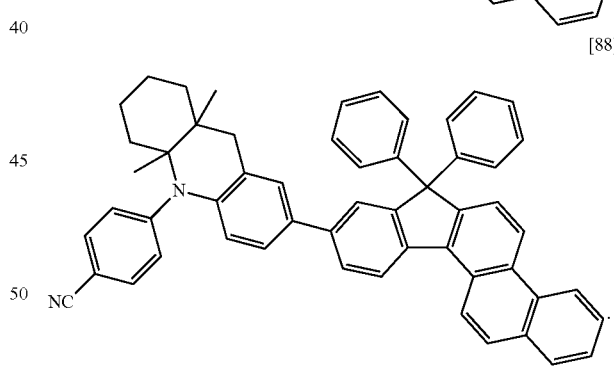

15. An organic light-emitting device, comprising:
a first electrode;
a second electrode facing the first electrode; and
an organic layer that between the first electrode and the second electrode, the organic layer including an emission layer,
wherein the organic layer includes the compound as claimed in claim 1.

16. The organic light-emitting device as claimed in claim 15, wherein the organic layer is formed by using a wet process.

17. The organic light-emitting device as claimed in claim 15, wherein:

the first electrode is an anode,
the second electrode is a cathode, and
the organic layer includes:
a hole transport region between the first electrode and the emission layer, the hole transport region including at least of a hole injection layer, a hole transport layer, a buffer layer, and an electron blocking layer, and
an electron transport region between the emission layer and the second electrode, the electron transport region including at least one of a hole blocking layer, an electron transport layer, and an electron injection layer.

18. The organic light-emitting device as claimed in claim 17, wherein the emission layer includes the compound.

19. The organic light-emitting device as claimed in claim 17, wherein the electron transport region includes a metal complex.

20. A flat display apparatus, comprising:
a thin film transistor, the thin film transistor including a source electrode and a drain electrode; and
the organic light-emitting device as claimed in claim 15, wherein the first electrode of the organic light-emitting device is electrically connected with the source electrode or the drain electrode of the thin film transistor.

21. A compound represented by Formula 1, below:

<Formula 1>

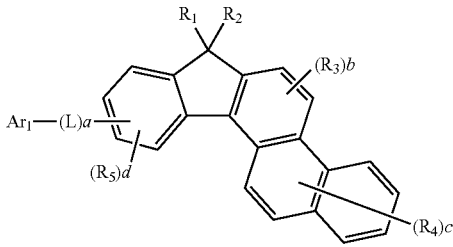

wherein, in Formula 1,
L is selected from a single bond, a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic condensed heteropolycyclic group;
$R_1$ to $R_5$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);
a, b, c, and d are each independently an integer selected from 0 to 6;
at least one substituent selected from the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic condensed heteropolycyclic group is selected from:
a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);
a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, carboxylic acid or a salt thereof, a sulfonic acid or a salt thereof, a phosphoric acid or a salt thereof, $C_1$-$C_{60}$ alkyl group, $C_2$-$C_{60}$ alkenyl group, $C_2$-$C_{60}$ alkynyl group, $C_1$-$C_{60}$ alkoxy group, $C_3$-$C_{10}$ cycloalkyl group, $C_2$-$C_{10}$ heterocycloalkyl group, $C_3$-$C_{10}$ cycloalkenyl group, $C_2$-$C_{10}$ heterocycloalkenyl group, $C_6$-$C_{60}$ aryl group, $C_6$-$C_{60}$ aryloxy group, $C_6$-$C_{60}$ arylthio group, $C_2$-$C_{60}$ heteroaryl group, a monovalent non-aromatic condensed polycyclic group, a monovalent non-aromatic condensed heteropolycyclic group, $-N(Q_{21})(Q_{22})$, $-Si(Q_{23})(Q_{24})(Q_{25})$, and $-B(Q_{26})(Q_{27})$; and
$-N(Q_{31})(Q_{32})$, $-Si(Q_{33})(Q_{34})(Q_{35})$, and $-B(Q_{36})(Q_{37})$;

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, and wherein $Ar_t$ is a group represented by one of Formulae 7a to 7f, below:

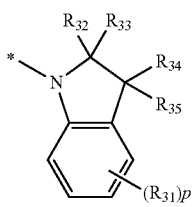

7a

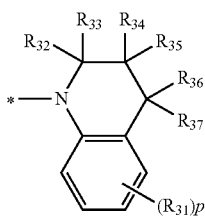

7b

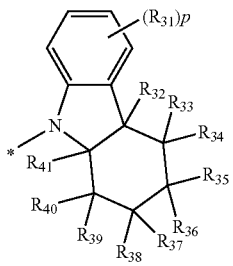

7c

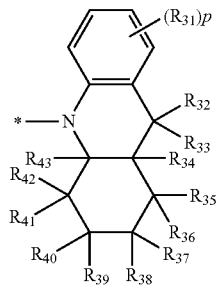

7d

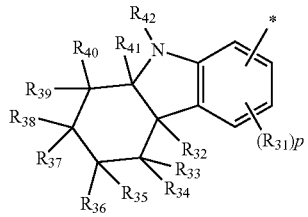

7e

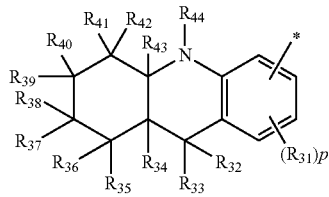

7f wherein, in Formulae 7a to 7f, $R_{31}$ to $R_{44}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group;

p is an integer selected from 1 to 4; when p is 2 or greater, each $R_{31}$ is identical to or different from each other; and

* is a binding site to a neighboring atom.

* * * * *